United States Patent
Aizawa et al.

(10) Patent No.: US 7,706,859 B2
(45) Date of Patent: Apr. 27, 2010

(54) DEVICE FOR DETECTING SHAPE OF ENDOSCOPE

(75) Inventors: Chieko Aizawa, Hachioji (JP); Fumiyuki Onoda, Tama (JP); Sumihiro Uchimura, Sagamihara (JP); Akira Taniguchi, Hachioji (JP)

(73) Assignee: Olympus Corporation, Tokyo (JP)

( * ) Notice: Subject to any disclaimer, the term of this patent is extended or adjusted under 35 U.S.C. 154(b) by 1085 days.

(21) Appl. No.: 10/544,557

(22) PCT Filed: Aug. 22, 2003

(86) PCT No.: PCT/JP03/10617

§ 371 (c)(1),
(2), (4) Date: Aug. 5, 2005

(87) PCT Pub. No.: WO2005/018439

PCT Pub. Date: Mar. 3, 2005

(65) Prior Publication Data

US 2006/0173289 A1  Aug. 3, 2006

(51) Int. Cl.
*A61B 5/05* (2006.01)

(52) U.S. Cl. ........................ 600/424; 600/117

(58) Field of Classification Search ......... 600/407–410, 600/117, 118, 424; 324/219, 246
See application file for complete search history.

(56) References Cited

U.S. PATENT DOCUMENTS

| | | | |
|---|---|---|---|
| 5,265,610 A | 11/1993 | Darrow et al. | |
| 5,361,029 A | 11/1994 | Rider et al. | |
| 5,840,024 A * | 11/1998 | Taniguchi et al. | 600/424 |
| 6,059,718 A * | 5/2000 | Taniguchi et al. | 600/117 |
| 6,511,417 B1 * | 1/2003 | Taniguchi et al. | 600/117 |
| 6,702,804 B1 * | 3/2004 | Ritter et al. | 606/1 |
| 6,755,816 B2 * | 6/2004 | Ritter et al. | 606/1 |
| 2003/0055317 A1 * | 3/2003 | Taniguchi et al. | 600/117 |
| 2006/0052664 A1 * | 3/2006 | Julian et al. | 600/146 |

FOREIGN PATENT DOCUMENTS

| | | |
|---|---|---|
| JP | 7-93083 | 4/1995 |
| JP | 7-111968 | 5/1995 |
| JP | 08-107875 | 4/1996 |
| JP | 09-028661 | 2/1997 |
| JP | 2000-93388 | 4/2000 |
| JP | 2000-189379 | 7/2000 |
| JP | 2000-342514 | 12/2000 |

(Continued)

*Primary Examiner*—Long V Le
*Assistant Examiner*—Sanjay Cattungal
(74) *Attorney, Agent, or Firm*—Scully, Scott, Murphy & Presser, P.C.

(57) ABSTRACT

Position detecting elements are disposed in an endoscope insertion portion at predetermined intervals. Even when the endoscope insertion portion is bent, position data representing the detected positions of the elements is used to infer or detect the shape of the insertion portion. A virtual element is disposed between adjoining elements so that a predetermined condition will be met. Position data of the virtual element is used together with the actually detected position data in order to interpolate data for the purpose of detecting the shape of the insertion portion. Consequently, as if a larger number of elements were disposed, the shape of the insertion portion can be detected highly precisely.

20 Claims, 30 Drawing Sheets

FOREIGN PATENT DOCUMENTS

| | | |
|---|---|---|
| JP | 2002-131009 | 5/2002 |
| JP | 2003-245242 | 9/2003 |
| JP | 2003-245243 | 9/2003 |
| WO | WO 99/56613 | 11/1999 |
| WO | WO 03/028547 A2 | 4/2003 |

* cited by examiner

○ : SENSE COIL ORIENTED IN X-AXIS DIRECTION
◯ : SENSE COIL ORIENTED IN Y-AXIS DIRECTION
◯ : SENSE COIL ORIENTED IN Z-AXIS DIRECTION

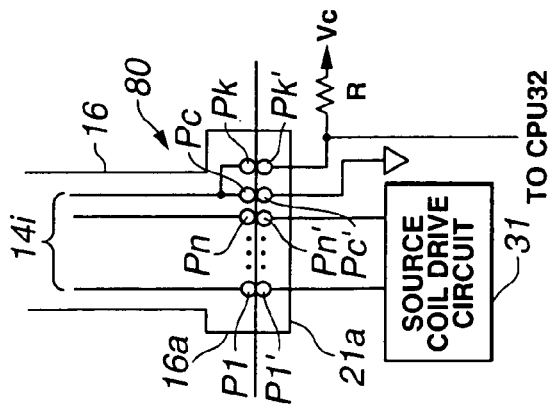
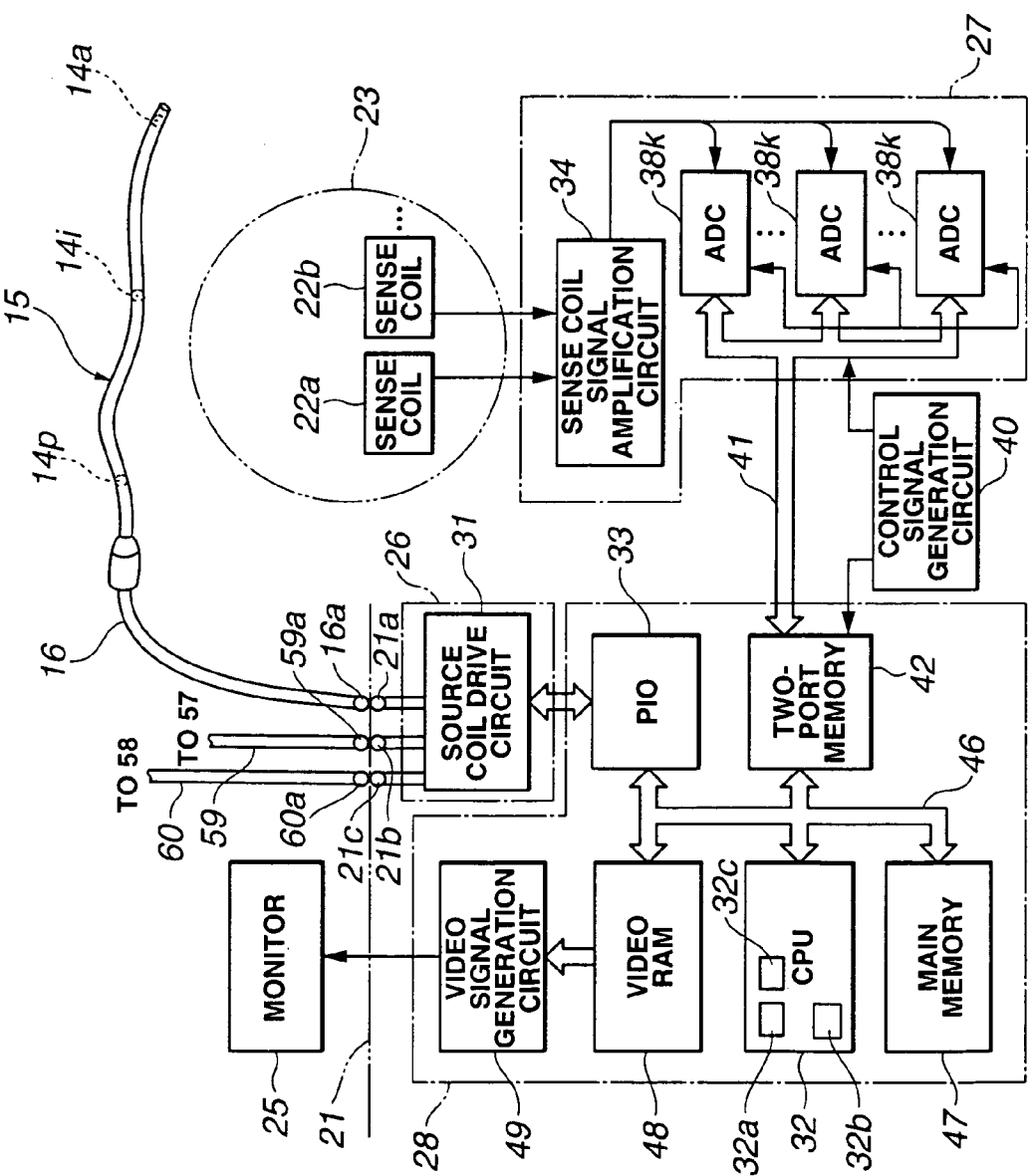

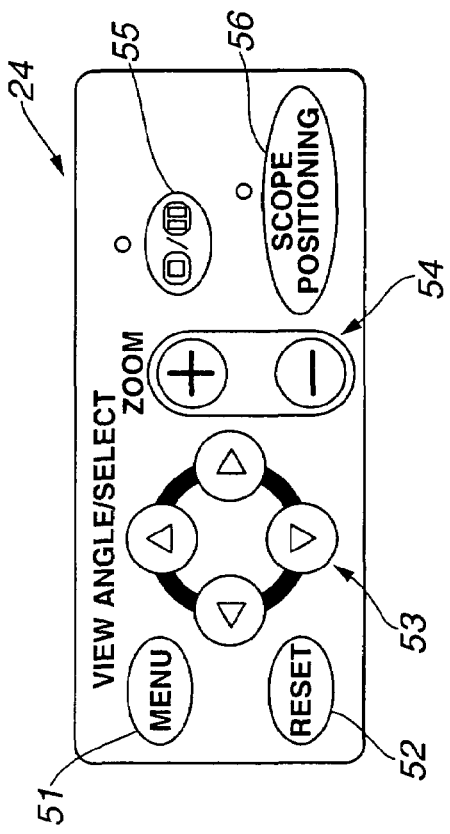
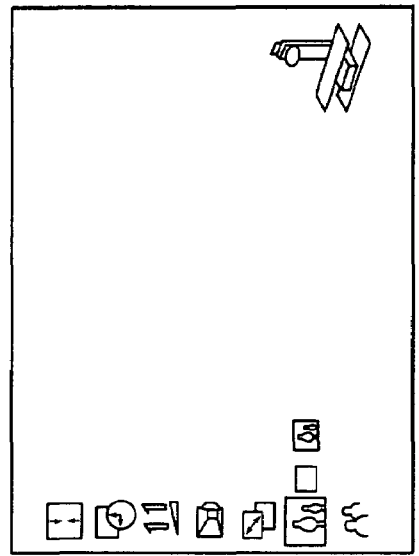
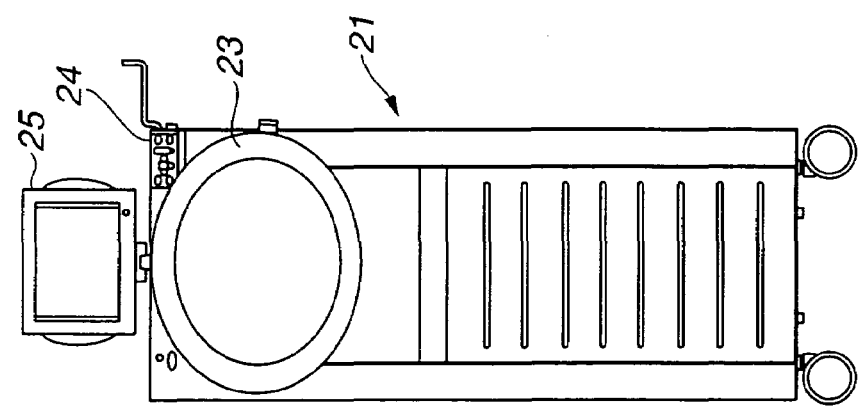

FIG.8A

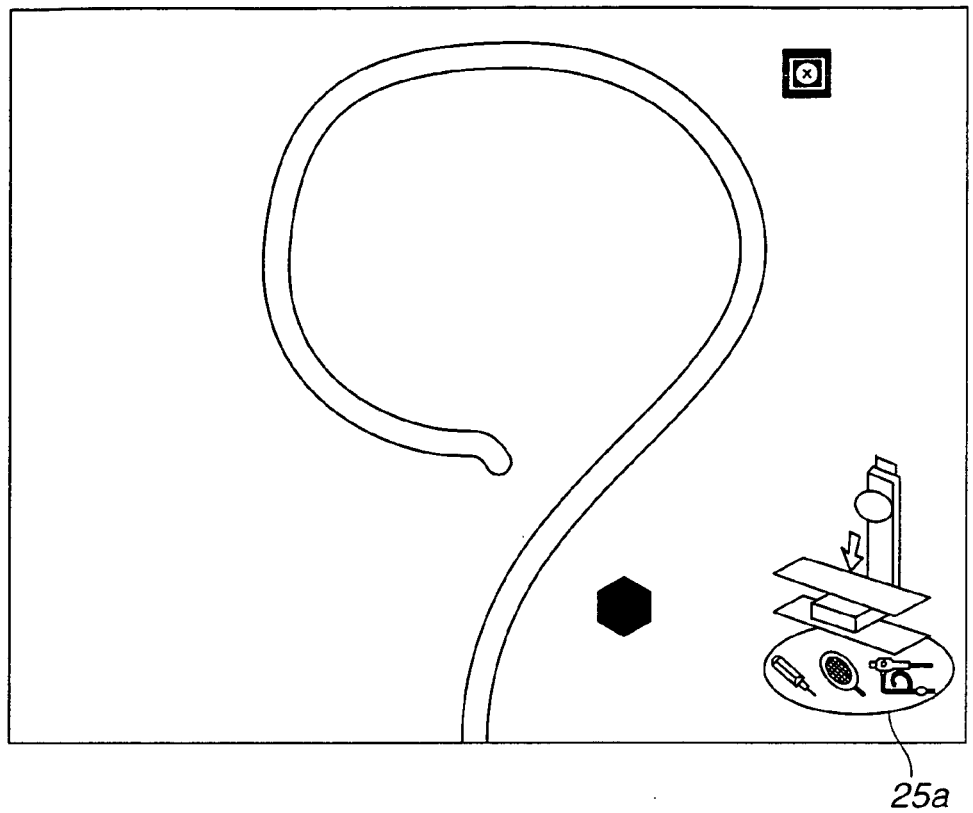

| ITEM | INDICATION | DESCRIPTION |
|---|---|---|
| SHAPE OF AN INDICATION OF A CONNECTED STATE | (screwdriver icon) | THE INDICATION IS DISPLAYED WHEN THE EXTERNAL MARKER IS CONNECTED. |
| | (racket icon) | THE INDICATION IS DISPLAYED WITH THE REFERENCE PLATE IS CONNECTED. |
| | (endoscope icon) | THE INDICATION IS DISPLAYED WHEN THE ENDOSCOPE IS CONNECTED. |
| COLOR OF AN INDICATION OF A CONNECTED STATE | GREEN | NORMAL |
| | YELLOW | PRECISION DEGRADED |
| | RED | ABNORMALITY OR FAILURE |

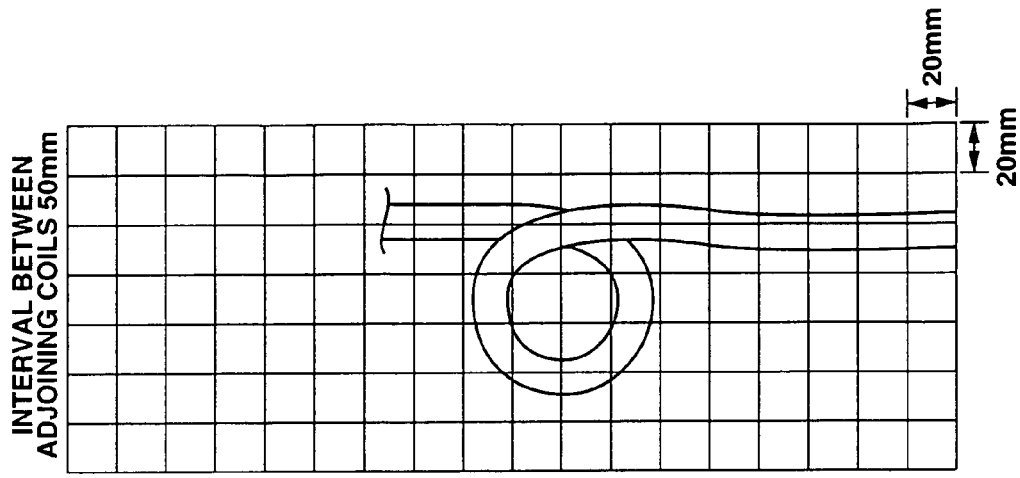
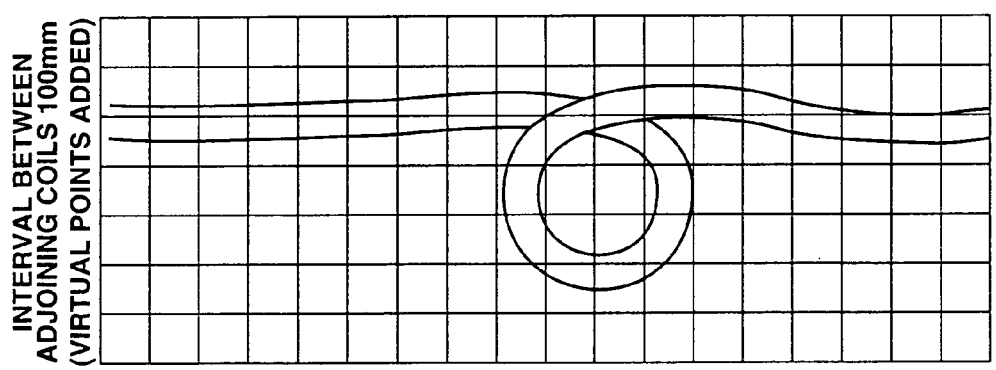
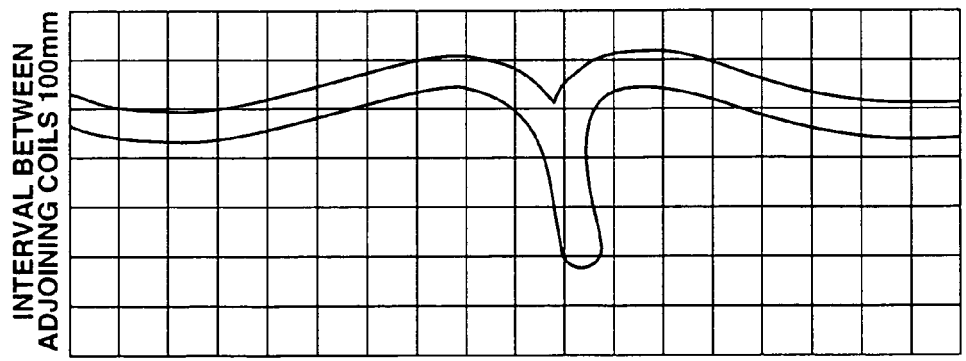

| SETTINGS | | JPN | US | GB | F | D |
|---|---|---|---|---|---|---|
| CONTENTS | | JAPAN | U.S.A 100 V REGION | BRITAIN 200 V REGION | FRANCE | GERMANY |
| | INDICATION OF DATE | YEAR /MONTH/ DAY | MONTH/ DAY/ YEAR | DAY/ MONTH/ YEAR | DAY/ MONTH/ YEAR | DAY/ MONTH/ YEAR |
| | FONT | JAPANESE | ENGLISH | ENGLISH | FRENCH | GERMAN |
| | SYMBOL | DOMESTIC | OVERSEAS | OVERSEAS | OVERSEAS | OVERSEAS |

| REFERENCE PLATE | | EXTERNAL MARKER | | SCOPE POSITIONING | |
|---|---|---|---|---|---|
| | | | | INACTIVATED | ACTIVATED |
| UNCONNECTED | | UNCONNECTED OR INVALID | | ①-1 | |
| | | CONNECTED | VALID | ①-1 | ①-2 |
| CONNECTED | INVALID | UNCONNECTED OR INVALID | | ②-1 | |
| | | CONNECTED | VALID | ②-1 | |
| | VALID | UNCONNECTED OR INVALID | | ②-1 | |
| | | CONNECTED | VALID | ②-1 | ②-2 |

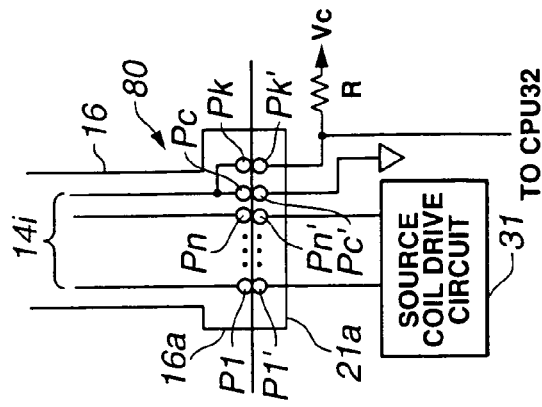
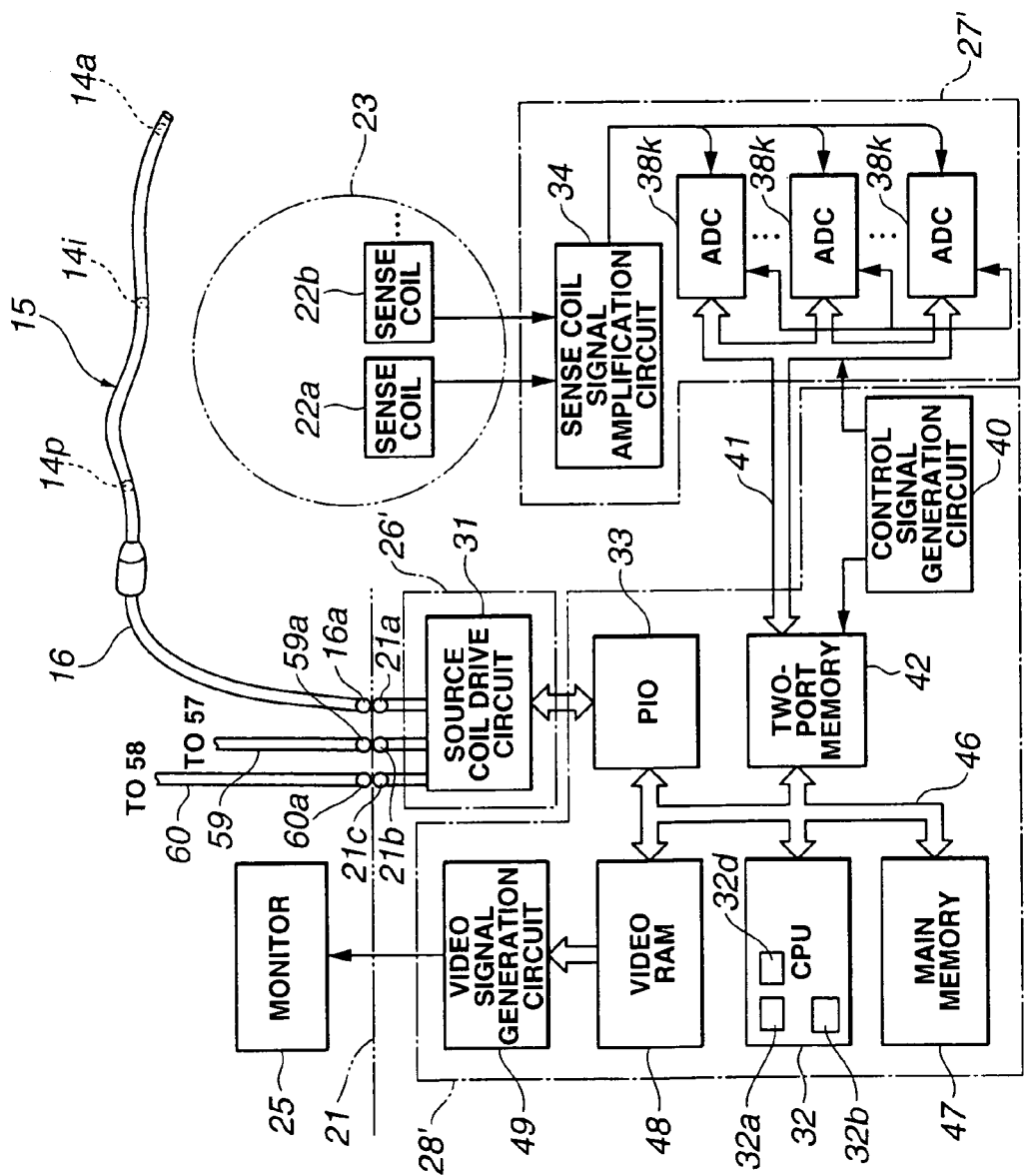
FIG.25B
FIG.25A

DEVICE FOR DETECTING SHAPE OF ENDOSCOPE

TECHNICAL FIELD

The present invention relates to a shape-of-endoscope detecting system that detects the shape of an insertion portion of an endoscope using magnetic-field generating elements and magnetic-field detecting elements and that displays the detected shape.

BACKGROUND ART

In recent years, a shape-of-endoscope detecting system has been adopted for detecting the shape of an endoscope inserted into a human body using magnetic-field generating elements and magnetic-field detecting elements, and displaying the detected shape on a display means.

For example, Japanese Unexamined Patent Application Publication No. 8-107875 has disclosed a system that detects the shape of an endoscope using magnetic fields and displaying the detected shape of the endoscope.

According to the patent publication, a plurality of magnetic-field generating elements disposed in the insertion portion of an endoscope, which is inserted into a human body, at predetermined intervals is driven in order to generate magnetic fields around the elements. Magnetic-field detecting elements disposed outside the human body are used to detect the three-dimensional positions of the respective magnetic-field generating elements. A curve continuously linking the positions of the magnetic-field generating elements is drawn, and a three-dimensional image representing a model of the insertion portion is displayed on a display means.

An operator or the like views the image to grasp the position of the distal section of the insertion portion inserted into a body or the inserted state of the insertion portion. This helps smoothly perform the work of inserting the insertion portion into a target region.

However, according to the related art, if the insertion portion is bent to form a loop having a small radius of curvature that is smaller than the interval between adjoining ones of the magnetic-field generating elements disposed in the insertion portion, the number of magnetic-field generating elements present in the looped portion of the insertion portion is so small that a streamlined shape similar to the actual shape of the looped insertion portion cannot be displayed.

An object of the present invention is to provide a shape-of-endoscope detecting system capable of highly precisely displaying the shape of an actual insertion portion despite a simple configuration.

DISCLOSURE OF INVENTION

A shape-of-endoscope detecting system has one of pluralities of magnetic-field generating elements and magnetic-field detecting elements disposed in an endoscope insertion portion that is inserted into a subject. The other of the pluralities of magnetic-field generating elements and magnetic-field detecting elements is disposed outside the subject. A detecting means detects the positions of one of the pluralities of elements disposed in the endoscope insertion portion using the position data of the other of the pluralities of elements. The shape of the endoscope insertion portion is inferred and displayed on a display means.

The shape-of-endoscope detecting system comprises a data interpolating means that based on the output of the detecting means, disposes virtual elements among one of the pluralities of elements whose positions are detected, and that interpolates data, which represents a position between adjoining ones of one of the pluralities of elements, using the position data of the virtual elements. Consequently, when the endoscope insertion portion is bent at a small curvature, as if the number of actually disposed elements were increased, the shape of the insertion portion can be displayed highly precisely.

BRIEF DESCRIPTION OF THE DRAWINGS

FIG. 1 to FIG. 22C are concerned with a first embodiment of the present invention;

FIG. 1 is a block diagram showing the configuration of an endoscopic system including the first embodiment of the present invention;

FIG. 2 shows an example of the layout of sense coils incorporated in a coil unit using a standard system of coordinates;

FIG. 3 is a block diagram showing the configuration of a shape-of-endoscope detecting system employed in the endoscopic system shown in FIG. 1;

FIG. 4A is a block diagram showing the configurations of a detection block and a host processor shown in FIG. 3;

FIG. 4B is a block diagram showing the configuration of a connection sensing mechanism;

FIG. 5 is a block diagram showing the configurations of the detection block and others;

FIG. 6 is a timing chart indicating the timings of actions of a two-port memory and others;

FIG. 7A, FIG. 7B, and FIG. 7C show a detecting apparatus, an operator panel, and a main menu respectively;

FIG. 8A and FIG. 8B show a connection display facility to be used when an endoscope or the like is connected to the detecting apparatus, and the shapes of an external marker connection icon and others;

FIG. 9A and FIG. 10A show the positions of source coils indicated in a case where no virtual point is designated, and the shape of an insertion portion displayed in this case;

FIG. 9B and FIG. 10B show the positions of the source coils indicated in a case where virtual points are designated, and the shape of the insertion portion displayed in this case;

FIG. 9C and FIG. 10C show the positions of the source coils indicated in a case where an interval between adjoining coils is actually determined and virtual points are actually designated, and the shape of the insertion portion displayed in this case;

FIG. 11 is a primary explanatory diagram concerning virtual point designation;

FIG. 12 is a flowchart describing the contents of a virtual point designation routine;

FIG. 13 is an explanatory diagram concerning virtual point designation described in FIG. 12;

FIG. 14 shows settings including an indication of a date and the like being varied depending on a destination of delivery;

FIG. 15 is an explanatory diagram showing the display on a monitor in which icons expressing source coils are rendered in green when the source coils incorporated in the insertion portion lie within a range of detection;

FIG. 16 shows a way of determining a display color depending on whether points interpolated using the positions of the source coils lie within the range of detection;

FIG. 17 is a flowchart describing a process that starts with magnetic field measurement and ends with scope model rendering;

FIG. 18 shows the insertion portion divided into three portions;

FIG. 20 shows designation of a cutting plane to be performed using a reference plate or the like;

FIG. 21 lists settings in details in relation to FIG. 20;

FIG. 22A to FIG. 22C are explanatory diagrams concerning the operation of automatic centering to be performed even when scope positioning is inactivated;

FIG. 23 to FIG. 35 are concerned with a second embodiment of the present invention;

FIG. 23 is a block diagram showing the configuration of a shape-of-endoscope detecting system in accordance with the second embodiment included in an endoscopic system;

FIG. 24 is a block diagram showing the configuration of the shape-of-endoscope detecting system employed in the endoscopic system shown in FIG. 23;

FIG. 25A is a block diagram showing the configurations of a receiving block and a control block;

FIG. 25B is a block diagram showing the structure of a connection sensing mechanism;

FIG. 26 is a flowchart describing a major procedure that starts with turning on of a power supply and ends with detection of a scope model;

FIG. 27 is a flowchart describing a detailed procedure of checking the action of a receiving system which is mentioned in FIG. 26;

FIG. 28 is a flowchart describing a detailed procedure of measuring an ambient noise and selecting a group of driving signals having different frequencies and containing a little noise;

FIG. 29 is a circuit diagram showing the primary configuration of a drive circuit that drives one source coil;

FIG. 31 and FIG. 32 are explanatory diagrams signifying an operation (of the present embodiment) to be exerted when discrete sides of signal lines are short-circuited in comparison with the one to be exerted before an improvement is made;

FIG. 34 and FIG. 35 are explanatory diagrams signifying an operation (of the present embodiment) to be exerted when a joint is disconnected in comparison with the one to be exerted before an improvement is made;

FIG. 36 is a block diagram showing the configuration of a shape-of-endoscope detecting system in accordance with the third embodiment;

FIG. 37 is a circuit diagram showing the configuration of a coil drive circuit;

FIG. 38 is an explanatory diagram showing waveforms of coil driving timing signals;

FIG. 39 shows waveforms of driving signals to be intermittently applied to coils divided into groups.

BEST MODE FOR CARRYING OUT THE INVENTION

Figure 1:
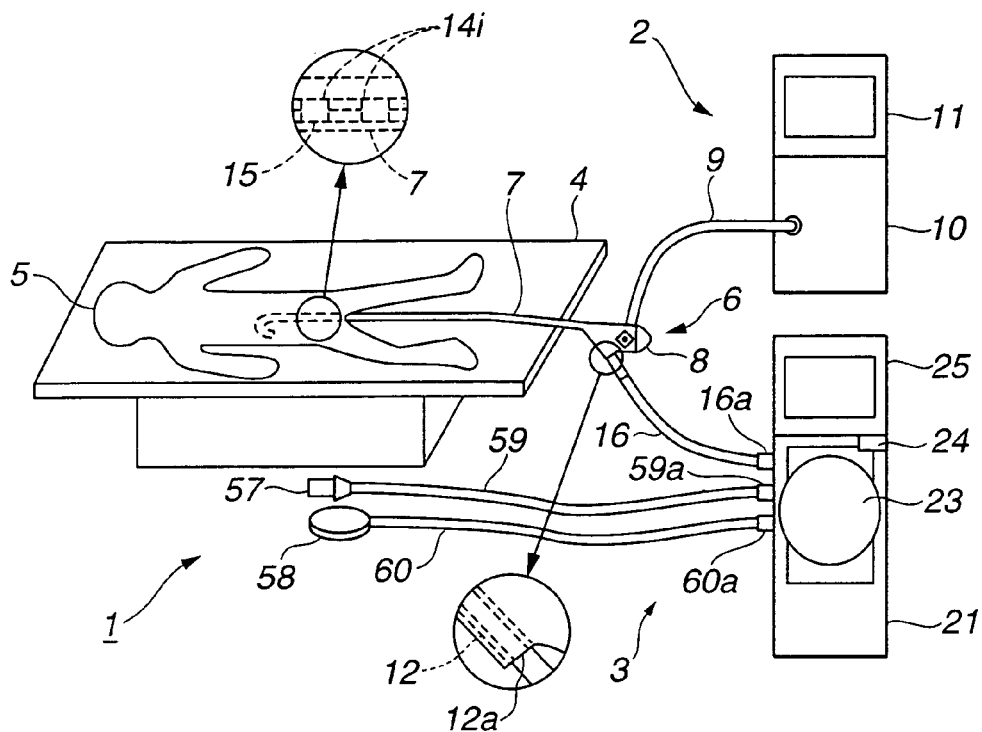

Referring to the drawings, embodiments of the present invention will be described below.

First Embodiment

Referring to FIG. 1 to FIG. 22C, a first embodiment of the present invention will be described below.

As shown in FIG. 1, an endoscopic system 1 including the first embodiment comprises an endoscope system 2 that enables endoscopic examination, and a shape-of-endoscope detecting system 3 that assists in performing endoscopic examination. The shape-of-endoscope detecting system 3 is used as an insertion aid means when an insertion portion 7 of an electronic endoscope 6 is inserted into a lumen of a patient 5 lying down on a bed 4 for the purpose of endoscopic examination.

The electronic endoscope 6 has an operation unit 8, which includes an angling knob, formed at the rear end of the elongated insertion portion 7 that has flexibility. A universal cord 9 is extended from the operation unit 8 and connected to a video imaging system (or a video processor) 10.

The electronic endoscope 6 has a light guide run through it. Illumination light emanating from a light source unit incorporated in the video processor 10 is propagated over the light guide, and emitted through an illumination window formed at the distal end of the insertion portion 7. A patient is thus illuminated. An image of an illuminated object that is a lesion is formed on an imaging device located on the image plane of an objective locked in an observation window adjoining the illumination window. The imaging device performs photoelectric conversion.

A signal resulting from photoelectric conversion is processed by a video signal processing unit incorporated in the video processor 10, whereby a standard video signal is produced. Based on the video signal, an image is displayed on an image observation monitor 11 connected to the video processor 10.

A forceps channel 12 lies through the electronic endoscope 6. A probe 15 including, for example, sixteen magnetic-field generating elements (or source coils) 14a, 14b, etc., and 14p (hereinafter, generically, 14i) is inserted through an inserting opening 12a of the forceps channel 12. Consequently, the source coils 14i are disposed in the insertion portion 7.

A connector 16a spliced to a source cable 16 extending from the rear end of the probe 15 is freely detachably attached to a detecting apparatus (main apparatus) 21 serving as a main apparatus of the shape-of-endoscope detecting system 3. The detecting apparatus 21 applies a high-frequency signal (driving signal) to the source coils 14i serving as a magnetic-field generating means over the source cable 16 serving as a high-frequency signal transmitting means. Consequently, the source coils 14i radiate electromagnetic waves accompanied by magnetic fields.

Figure 2:
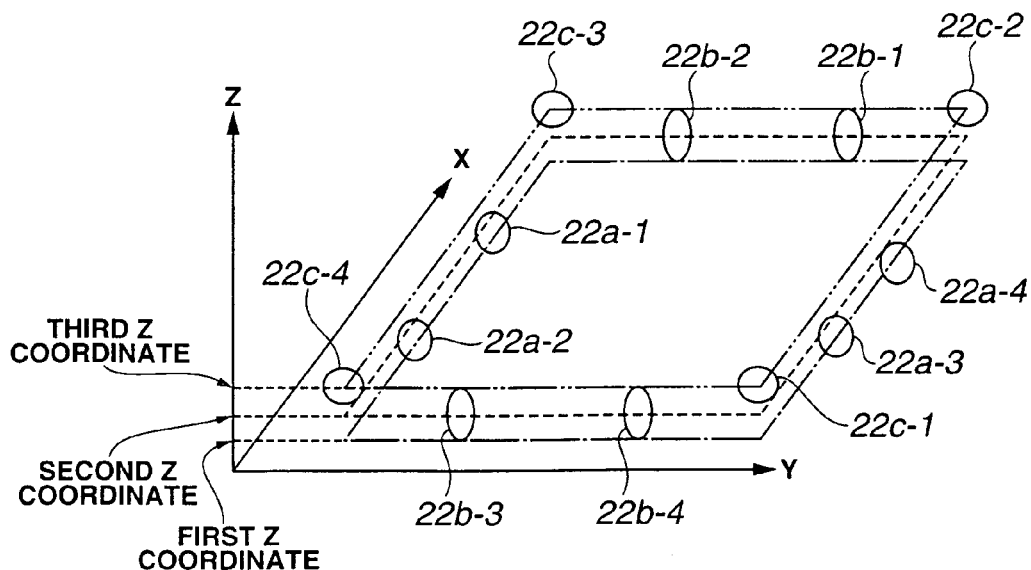

The detecting apparatus 21 located near the bed 4 on which the patient 5 lies down has a (sense) coil unit 23 that can be freely moved (raised or lowered) in vertical directions. A plurality of magnetic-field detecting elements (sense coils) is incorporated in the coil unit 23 (more particularly, as shown in FIG. 2, twelve sense coils (hereinafter, generically, 22j) are arranged in such a manner that: sense coils 22a-1, 22a-2, 22a-3, and 22a-4 are oriented in the direction of, for example, an X axis and located at a height indicated with, for example, a first Z coordinate; sense coils 22b-1, 22b-2, 22b-3, and 22b-4 are oriented in the direction of a Y axis and located at a height indicated with a second Z coordinate different from the first Z coordinate; and sense coils 22c-1, 22c-2, 22c-3, and 22c-4 are oriented in the direction of a Z axis and located at a height indicated with a third Z coordinate different from the first and second Z coordinates).

The sense coils 22j are connected to the detecting apparatus 21 over a cable that is not shown and extended from the coil unit 23. The detecting apparatus 21 has an operator panel 24 which a user uses to operate the apparatus. Moreover, the detecting apparatus 21 has a liquid crystal monitor 25 mounted as a display means, on which the shape of an endoscope is displayed, on the top thereof.

Figure 3:
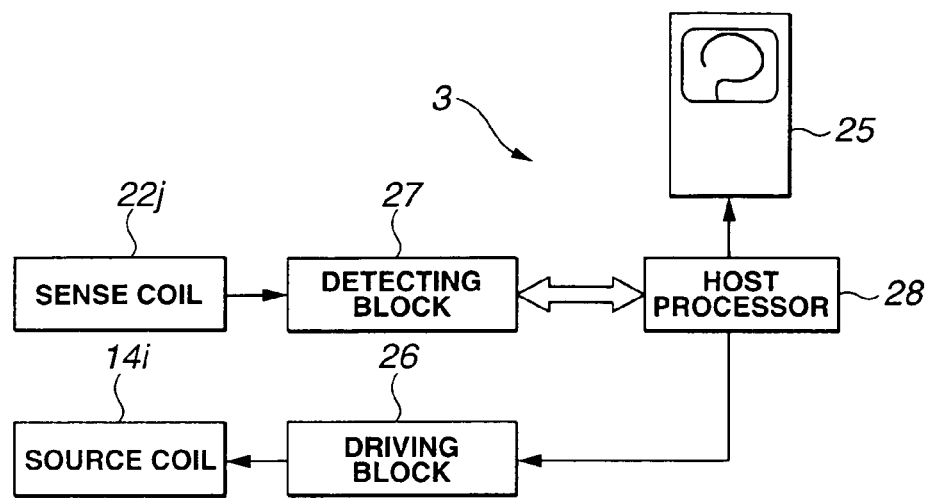
Figure 6:
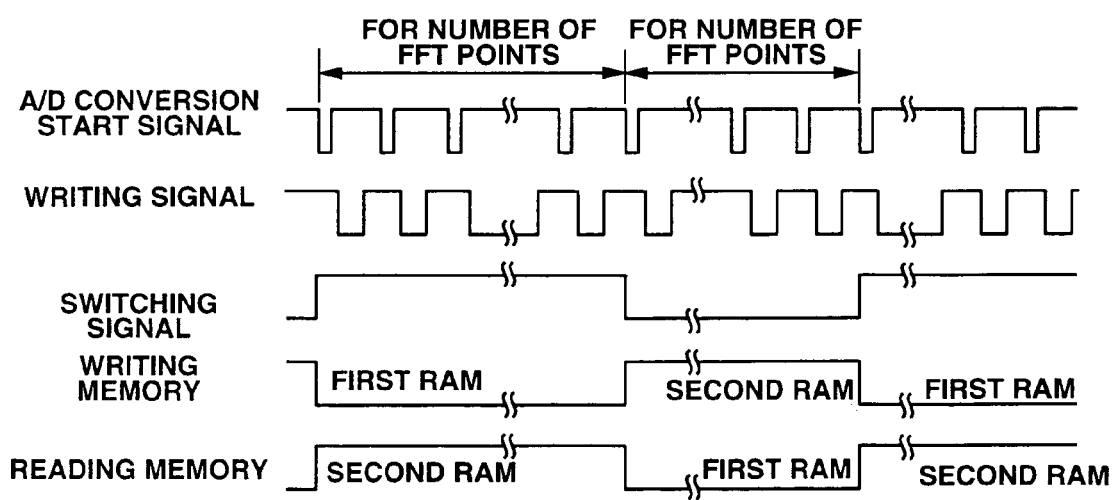

The shape-of-endoscope detecting system 3 comprises: as shown in FIG. 3, a driving block 26 that drives the source coils 14i; a detecting block 27 that detects signals received by the sense coils 22j incorporated in the coil unit 23; and a host processor 28 that processes signals detected by the detecting block 27.

As shown in FIG. 4A, the probe 15 disposed in the insertion portion 7 of the electronic endoscope 6 has, as mentioned above, the sixteen source coils 14i juxtaposed at predetermined intervals in order to induce magnetic fields. The source coils 14i are connected to a source coil drive circuit 31 that produces sixteen driving signals having different frequencies and that is included in the driving block 26.

The source coil drive circuit 31 drives the source coils 14i using the driving signals that are sine waves having different frequencies. The frequencies of the driving signals are determined based on driving frequency determination data (or driving frequency data) stored in a driving frequency determination data storage means or driving frequency determination data memory means that is not shown and that is incorporated in the source coil drive circuit 31. The driving frequency data is stored in the driving frequency data storage means (not shown) incorporated in the source coil drive circuit 31 via a parallel input/output circuit (PIO) 33 by means of a central processing unit (CPU) that calculates the shape of an endoscope and that is included in the host processor 28.

On the other hand, the twelve sense coils 22j incorporated in the coil unit 23 are connected to a sense coil signal amplification circuit 34 included in the detecting block 27.

Figure 5:
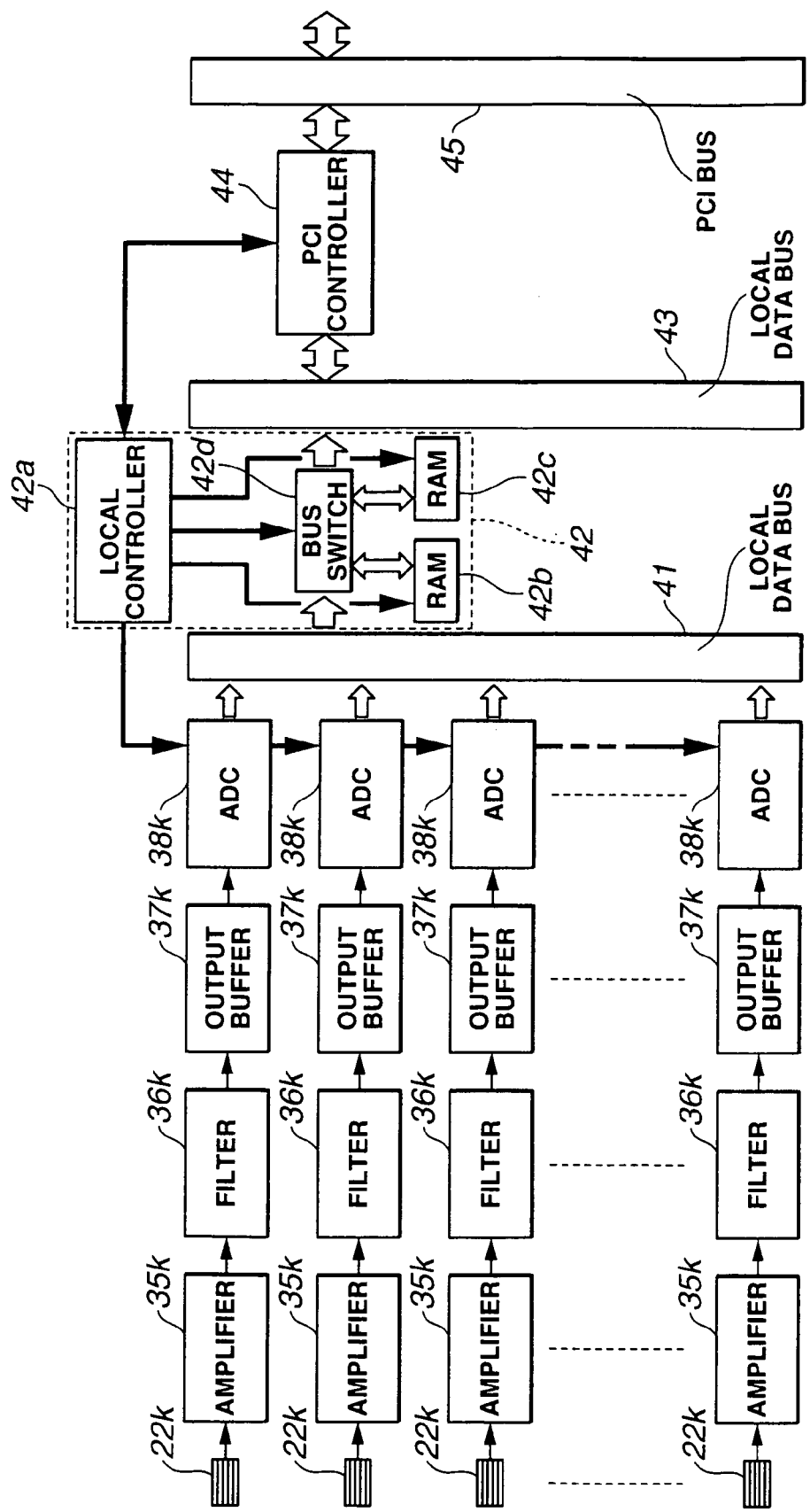

Twelve single-core coils 22k serving as the sense coils 22j are, as shown in FIG. 5, connected to amplifiers 35k included in the sense coil signal amplification circuit 34, whereby twelve processing systems are constructed. Feeble signals detected by the single-core coils 22k are amplified by the amplifiers 35k. Filters 36k remove unnecessary signal components, which belong to a band of frequencies and are generated by the group of source coils, from the amplified signals. The resultant signals are transmitted to output buffers 37k, and converted into digital signals, which can be read by the host processor 28, by means of analog-to-digital (A/D) converters 38k.

The detecting block 27 includes the sense coil signal amplification circuit 34 and the A/D converters 38k. The sense coil signal amplification circuit 34 comprises the amplifiers 35k, filters 36k, and output buffers 37k.

Referring back to FIG. 4A, the outputs of the twelve systems included in the sense coil signal amplification circuit 34 are transmitted to the twelve A/D converters 38k, and converted into digital data items that are sampled at a predetermined sampling rate according to a clock sent from a control signal generation circuit 40. The digital data is written in a two-port memory 42 over a local data bus 41 in response to a control signal sent from the control signal generation circuit 40.

Incidentally, the two-port memory 42 comprises, as shown in FIG. 5, from a functional viewpoint, a local controller 42a, a first RAM 42b, a second RAM 42c, and a bus switch 42d. According to the timing indicated in FIG. 6, the A/D converters 38k start analog-to-digital conversion in response to an A/D conversion start signal sent from the local controller 42a. In response to a switching signal sent from the local controller 42a, the bus switch 42d switches the RAM 42b and RAM 42c. The RAM 42b and RAM 42c are thus alternately used as reading and writing memories. After the power supply is turned on, data is fetched in response to a Write signal.

Referring back to FIG. 4A, the CPU 32 reads the digital data written in the two-port memory 42 over an internal bus 46 comprising a local data bus 43, a PCI controller 44, and a PCI bus 45 (see FIG. 5). Using the main memory 47, as will be described later, the CPU 32 performs frequency sampling (fast Fourier transformation (FFT)) on the digital data, and thus separates or samples pieces of magnetic-field detection information that correspond to frequency components having the same frequencies as the frequencies of the driving signals applied to the source coils 14i. The coordinates representing the spatial positions of the source coils 14i incorporated in the insertion portion 7 of the electronic endoscope 6 are calculated based on the digital data items of the separated pieces of magnetic-field detection information.

Moreover, the inserted state of the insertion portion 7 of the electronic endoscope 6 is inferred from the calculated position coordinate data items. Display data representing an image of the shape of the endoscope is produced and transmitted to a video RAM 48. A video signal generation circuit 49 reads data from the video RAM 48, converts the data into an analog video signal, and transmits the signal to the liquid crystal monitor 25. According to the analog video signal, the shape of the inserted insertion portion 7 of the electronic endoscope 6 (which shall be referred to as a scope model) is displayed on the display screen of the liquid crystal monitor 25.

The CPU 32 calculates pieces of magnetic-field information associated with the respective source coils 14i, that is, electromotive forces (amplitudes of sine wave signals) induced in the single-core coils 22k realizing the sense coils 22j as well as pieces of phase information. The phase information indicates whether the polarity of an electromotive force is positive or negative.

Moreover, according to the present embodiment, an external marker 57 and a reference plate 58 may be, as shown in FIG. 1, connected to the detecting apparatus 21. The external marker 57 is used to indicate an external position so as to help recognize the position of the insertion portion 7 inserted into a body. The reference plate 58 is attached to the abdomen of the patient 5 in order to display a scope model in a specific direction (relative to the patient 5) despite a change in the posture of the patient 5.

The external marker 57 has one source coil stored therein. A connector 59a spliced to the proximal end of a cable 59 extending from the external marker 59 is freely detachably attached to the detecting apparatus 21.

By attaching the connector 59a, the source coil incorporated in the external marker 57 is driven in the same manner as the source coils incorporated in the probe 15. The position of the source coil incorporated in the external marker 57 detected by the coil unit 23 is presented in the same manner as the scope model on the monitor 25.

Moreover, the reference plate 58 has three source coils placed on the disk plate incorporated in the disk-like body thereof. A connector 60a spliced to the proximal end of a cable 60 coupled to the three source coils is freely detachably attached to the detecting apparatus 21.

By detecting the positions of the three source coils, a plane on which the source coils are disposed is determined. Namely, based on the positions of the three source coils, a scope model is rendered so that it will express the insertion portion 7 seen from a direction perpendicular to the plane on which the source coils are disposed.

Moreover, as shown in FIG. 4A, according to the present embodiment, the detecting apparatus 21 has connector receptacles 21a, 21b, and 21c to which the connector 16a of the probe 15, the connector 59a of the external marker 57, and the connector 60a of the reference plate 58 are fitted. The connector receptacles 21a, 21b, and 21c are connected to a source coil drive circuit 31.

As shown in FIG. 4B, for example, the connector receptacle 21a has a connection sensing mechanism 80 that detects whether the connector 16a is fitted into the connector receptacle 21a.

The connector 16a includes, in addition to connection pins p1 to pn that are connected to the source coils 14a to 14p, a common pin pc and a connection sensing pin pk. The pin pk is connected to the pin pc.

The connector receptacle 21a includes pin jacks p1' to pn', pc', and pk' into which the connection pins p1 to pn, pc, and pk are fitted. The pin jack pc' is grounded.

Moreover, the pin jack pk' is connected to a power terminal Vc via a pull-up resistor R, and also connected to a connection sensing port of the CPU 32. The CPU 32 checks if the voltage level at the pin jack pk' is as high as the voltage level at the power terminal Vc or as low as the ground level, and thus judges whether the probe 15 is unconnected or connected to the detecting apparatus 21.

Namely, when the probe 15 is connected, the pin jack pk' is, as shown in FIG. 4B, connected to the grounded pin jack pc' via the conducting pins pk and pc of the connector 16a. Consequently, the voltage level at the pin jack pk' is as low as the ground level. It is judged that the probe 15 is connected. On the other hand, when the probe 15 is unconnected, the voltage level at the pin jack pk' is as high as the voltage level at the power terminal Vc. It is then judged that the probe 15 is unconnected.

Incidentally, the connector receptacles 21b and 21c have the same connection sensing mechanism. When the (endoscope including) probe 15, external marker 57, and reference plate 58 are connected, the CPU 32 displays an endoscope connection icon, an external marker connection icon, and a reference plate connection icon in a connected state indicator section 25a that is for example, the right lower corner of the monitor 25 shown in FIG. 14A as described later. If the probe 15, external marker 57, and reference plate 58 are unconnected, the icons are not displayed.

According to the present embodiment, the CPU 32 has a facility of a verifying means 32a that monitors if any of position data items concerning the source coils 14i (including, in addition to the source coils 14i incorporated in the probe 15, the source coil incorporated in the external marker 57 and the source coils incorporated in the reference plate 58) is abnormal.

The verifying means 32a verifies an abnormality as described below.

a) If the position data of each source coil 14i falls within a predetermined range, the position data is verified to be valid. If the position data falls outside the predetermined range, the position data is verified to be invalid.

b) The electromotive force detected by each of the sense coils 22j that detect magnetic fields induced by the respective source coils 14i is compared with a predetermined reference value. If the electromotive force exceeds the reference value, it is verified that the position of a source coil concerned can be detected. If the electromotive force is equal to or smaller than the reference value, it is verified that the position thereof cannot be detected.

c) If the result of sensing performed by a source coil disconnection/short-circuit sensing means that is not shown demonstrates that a disconnection or a short circuit has occurred in a certain source coil, it is verified that the source coil is abnormal. Otherwise, the source coil is verified to be normal.

Based on the results of the verifications a), b), and c), it is verified whether the position data of each source coil is abnormal. Moreover, the verifying means 32a verifies as described below whether the source coils incorporated in the probe are abnormal.

If a distance between two source coils 14i and 14i+1 calculated from the positions of the source coils is shorter or longer than a predetermined range of distances, the verifying means 32a verifies that the source coils are abnormal. If the distance between two source coils 14i and 14i+1 falls within the predetermined range, the verifying means 32a verifies that the source coils are normal.

When the three-dimensional position of a scope model or the external marker 57 is indicated, the result of verification is presented to an operator in a discernible manner with a display form varied depending on the result of verification.

For example, when the endoscope connection icon, external marker connection icon, and reference plate connection icon are displayed, the CPU 32 uses a facility of a display color selecting means 32b to control the display on the monitor 25 according to the result of verification. Consequently, an operator can easily recognize whether detection is achieved to a predetermined degree of precision or higher by checking the display color in which the icons are displayed in the connected state indicator section 25a that is the right lower corner of the monitor 25 shown in FIG. 8A.

Moreover, according to the present embodiment, the icons are displayed in the connected state indicator section 25a in different colors. In addition, the display colors in which a scope model is displayed on the display surface of the monitor 25 and the position of the external marker 57 is indicated are varied depending on whether the endoscope lies within an effective range of detection.

For example, as far as the probe 15 (that is, endoscope 6) is concerned, a scope model is displayed by interpolating data using the detected positions of the source coils 14i. For example, a scope model portion expressing a portion of the endoscope lying within the effective range of detection and a scope model portion expressing the other portion thereof lying outside the effective range of detection are displayed in different colors.

Therefore, the result of verification performed by the verifying means 32a is reflected on image data stored in, for example, the video RAM 48. In other words, when the CPU 32 stores image data, which represents a scope model or the like, in the video RAM 48, red, green, and blue image data items are stored in red, green, and blue storage areas in the video RAM 48 according to the result of verification.

For example, if the endoscope whose scope model is displayed on the monitor 25 entirely lies within the effective range of detection, red, green, and blue image data items are stored in the red, green, and blue storage areas in the video RAM 48 so that the scope model will be displayed in a predetermined color, for example, gray.

On the other hand, when part of the endoscope expressed with part of a scope model lies outside the effective range of detection, green and red image data items are stored in the green and red storage areas in the video RAM 48 so that the part of the scope model will be displayed in, for example, yellow.

The same applies to the external marker 57. Depending on whether the external marker 57 lies within the effective range of detection, the color in which the external marker is displayed is varied.

According to the present embodiment, whether the endoscope or the external marker 57 lies within the effective range of detection and is detected to a predetermined degree of precision or higher can be easily learned from the display color in which a scope model or the icon expressing the external marker 57 is displayed on the monitor 25.

Moreover, when the probe 15 is connected, although the source coils are driven, if the sense coils cannot detect any signals, it is judged that the probe 15 has failed.

FIG. 7A and FIG. 7B show the detecting apparatus 21 and the operator panel 24 included in the detecting apparatus 21. As shown in FIG. 7B, the operator panel 24 has: a menu button 51 that is used, to display a menu bar (contained in a main menu shown in FIG. 7C); a reset button 52 to be used to reset settings; view angle/select buttons 53 to be used to change a view angle by rotating a scope model using the buttons bearing up, down, right, and left arrow marks, to be used to select a facility (using the buttons bearing the up and down arrow marks), or to be used to select an item (using the buttons bearing the right and left arrow marks) (which may be, for brevity's sake, referred to as the ↑, ↓, →, and ← buttons); zoom buttons 54 bearing + and − marks and being used to enlarge or reduce a scope model or to change a date or a place (which may be referred to as the + and − buttons); a single-screen/split-screen button 55 to be used to direct display of one screen image or display of two screen images; and a scope positioning button 56 to be used to determine a position at which display of a scope model is started.

The functions of the buttons will be detailed below.

(a) Menu Button 51

The menu button 51 is used to display or not to display the menu bar at a specific position on a monitor screen (when the menu bar 50 is not displayed, the determined settings of facilities are stored in a memory). The menu button 51 is used to select any of items such as a date and a place from a determination screen image.

(b) Reset Button 52

After any of items associated with facilities is selected from the menu bar and the setting of an item is determined, the reset button 52 is used to return the setting to a previous value attained before the menu bar is displayed.

In a date/place determination screen image, the settings of the facilities associated with the items are returned to the values attained before the date/place determination screen image is displayed.

(c) View Angle/Select Buttons 53

The ←, ↑, ↓, and → buttons are used to rotate a scope model. The ↑ and ↓ buttons are used to select an item from the menu bar. The ← and → buttons are used to display or select a submenu or to determine the setting of a facility that is selected in the date/place determination screen image using the menu button 51.

(d) Zoom Button 54

The zoom button 54 is used to enlarge or reduce a scope model or to determine the settings of facilities associated with the items contained in the date/place determination screen image.

(e) Single-Screen/Split-Screen Button 55

The single-screen/split-screen button 55 is used to display two screen images representing views that are seen from different view points and oriented in different directions.

(f) Scope Positioning Button 56

After the external marker is moved to the position of the patient's anus or any other position at which an operator wants to start display, the scope positioning button 56 is used to start display at the position.

Next, referring to FIG. 8A and FIG. 8B, a facility of displaying a connected state will be described below.

According to the present embodiment, as described in FIG. 1 and FIG. 4A, the endoscope 6, reference plate 57, and external marker 58 can be connected to the detecting apparatus 21 so that they can be disconnected freely.

Depending on whether the endoscope 6, reference plate 57, or external marker 58 is connected, whether the endoscope 6, reference plate 57, or external marker 58 is connected can be readily discerned through the connected state indicator section 25a on the monitor 25.

Moreover, when the endoscope 6, reference plate 57, or external marker 58 can be connected to the detecting apparatus 21, whether it is connected normally, whether the connection degrades precision, and whether any of the endoscope 6, reference plate 57, and external marker 58 is abnormal or has failed are indicated using different display colors. Thus, a user can recognize a connected state from the display color.

When the external marker 57, reference plate 58, and endoscope 6 are connected to the detecting apparatus 21, the external marker connection icon, reference plate connection icon, and endoscope connection icon are, as shown in FIG. 8A, displayed in the connected state indicator section 25a.

FIG. 8B lists and describes the shapes of the external marker connection icon, reference plate connection icon, and endoscope connection icon which are displayed in the connected state indicator section 25a. When the external marker, reference plate, or endoscope is connected normally, a display color in which an icon expressing it is displayed is green. When the connection degrades precision, the display color is yellow. When the external marker, reference plate, or endoscope is abnormal or has failed, the display color is red. A user can recognize the connected state from the display color.

Incidentally, the display color is varied depending on whether the degree of precision is of the level permitting use. Alternatively, the icons to be displayed in the connected state indicator section 25a may not be flickered normally. When precision is degraded, the icon concerned may be flickered. Thus, a display form may be changed.

Moreover, the present invention is not limited to the mode of varying the display form in which pieces of visual information representing the external marker, reference plate, and endoscope are displayed on the monitor 25. Alternatively, a notification form in which a sound or voice is radiated in order to notify whether the precision with which the external marker, reference plate, or endoscope can act is of the level permitting its use may be varied. Moreover, the way of notifying whether the external marker, reference plate, or endoscope is connected to the detecting apparatus 21 is not limited to a visual notification form. Alternatively, an acoustic notification form in which a sound is employed may be employed. For example, although the external marker, reference plate, or endoscope normally acts with high precision, if the precision is degraded, the fact may be notified with a sound. (For example, if the external marker, reference plate, or endoscope can act with precision of the level permitting its use, no sound is radiated. If the precision is degraded, a sound or voice is radiated. Namely, whether precision is degraded may be indicated or notified with the presence or absence of a sound or voice or a change in the sound or voice.)

Moreover, according to the present embodiment, data is interpolated using pieces of position information representing the detected positions of the source coils $14i$ in order to calculate the shape of the insertion portion 7. In this case, a virtual source coil may be disposed at an intermediate point between adjoining ones of the source coils $14i$. In addition to the positions of the source coils $14i$ actually disposed in the insertion portion 7, the positions of the virtual source coils may be used to calculate the shape of the insertion portion. In this case, even if the insertion portion is bent at a small curvature, the shape of the insertion portion can be calculated more highly precisely.

Therefore, the CPU 32 shown in FIG. 4A employs a facility of a virtual point designating means that adds virtual elements.

The operation to be exerted by the virtual point designating means $32c$ will be outlined in conjunction with FIG. 9A to FIG. 10C. According to the present embodiment, the source coils $14i$ are disposed at intervals of a length L of, for example, 100 mm.

Figure 9C:
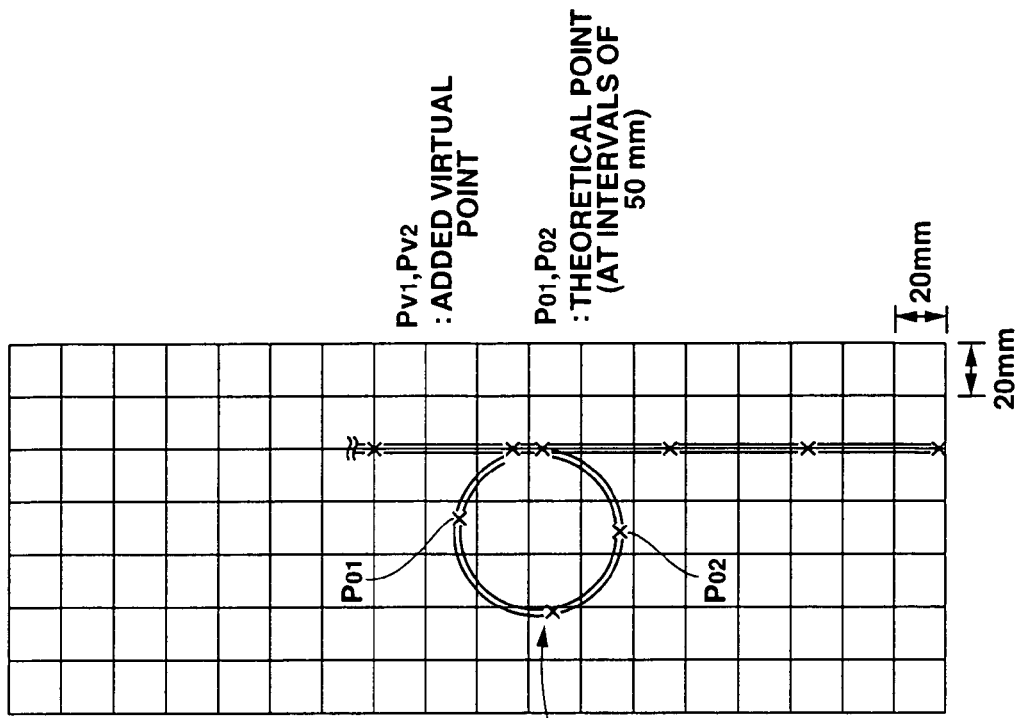
Figure 9B:
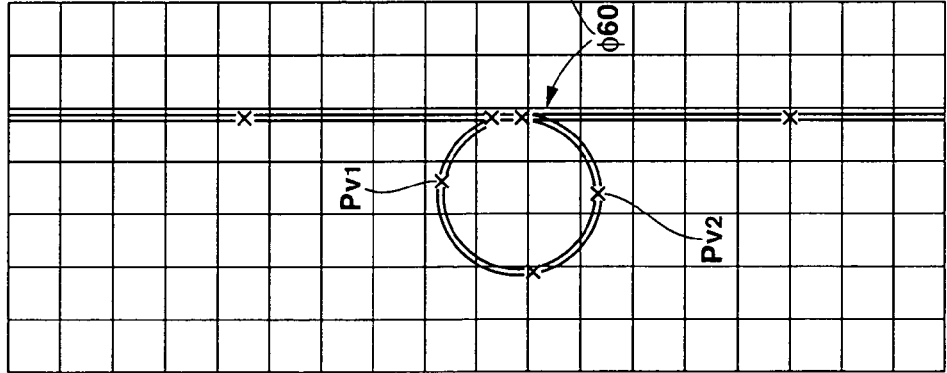
Figure 9A:
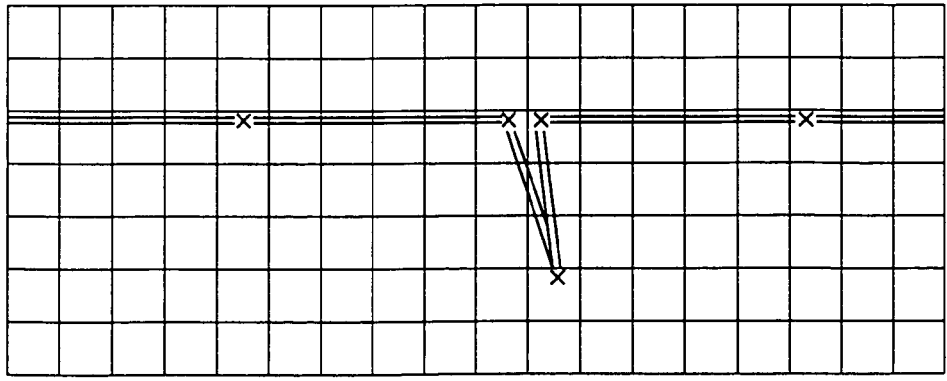

Assume that the insertion portion 7 is bent to form a loop having, for example, 60 mm, and the positions of the source coils $14i$ incorporated in the insertion portion are indicated with crosses in FIG. 9A. In this case, if interpolation is performed normally, the shape of the insertion portion is not detected as a loop but is displayed as shown in FIG. 10A.

Assume that the insertion portion 7 is bent to form a loop having a diameter of, for example, 60 mm, and the positions of the source coils incorporated in the insertion portion are indicated with crosses in FIG. 9A. In this case, if interpolation is performed normally, the shape of the insertion portion is not detected as a loop but is displayed as shown in FIG. 10A.

In contrast, assume that a virtual source coil is, as shown in FIG. 9B, disposed between adjoining ones of the source coils $14i$ incorporated in the looped portion of the insertion portion 7 (the positions of the virtual source coils are indicated with Pv1 and Pv2). This state approximates or is equivalent to a state in which a larger number of source coils is disposed in the looped portion. If interpolation is performed in order to calculate the shape of the insertion portion 7 in the same manner as that in the case shown in FIG. 9A, the looped shape of the insertion portion 7 is identified. Consequently, a scope model shaped like a loop as shown in FIG. 10B can be displayed.

FIG. 9C shows the positions of source coils adopted when the length between adjoining coils is set to 50 mm and the insertion portion is looped. In this case, if interpolation is performed in order to calculate the shape of the insertion portion, the calculated shape is displayed as shown in FIG. 10C.

Namely, when virtual point designation $32c$ is performed as it is in the present embodiment, the shape of the insertion portion can be detected and displayed with higher precision as if another source coil were additionally disposed at an intermediate point between adjoining ones of the actual source coils $41i$.

Figure 11:
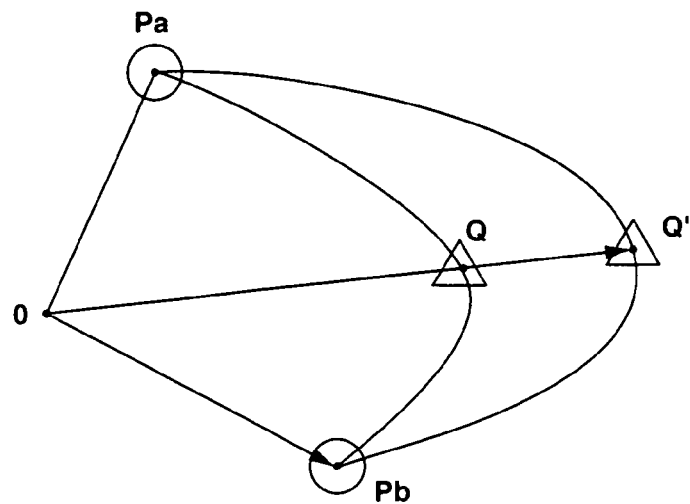

The virtual point designating means $32c$ for designating virtual points basically adopts software for designating a virtual point Q' shown in FIG. 11.

Referring to FIG. 11, Pa and Pb denote source coil detection points. An arc PaQPb shall be a shape detected through normal interpolation. If the length of the arc PaQPb is shorter than the length L between adjoining source coils (actually, 100 mm) by a predetermined length or more, a vector OQ is extended beyond point Q. A point Q u distanced from the point Q by the length L between adjoining source coils is regarded as a virtual point.

The point Q' is added to the points of the source coils actually disposed in the insertion portion 7, and an intermediate position between the positions of adjoining source coils is interpolated. In this case, even if the insertion portion is bent like a loop with a predetermined rate of deviation, the shape of the insertion portion can be displayed with high precision as described in conjunction with FIG. 9B and FIG. 10B (or FIG. 9C and FIG. 10C).

Figure 12:
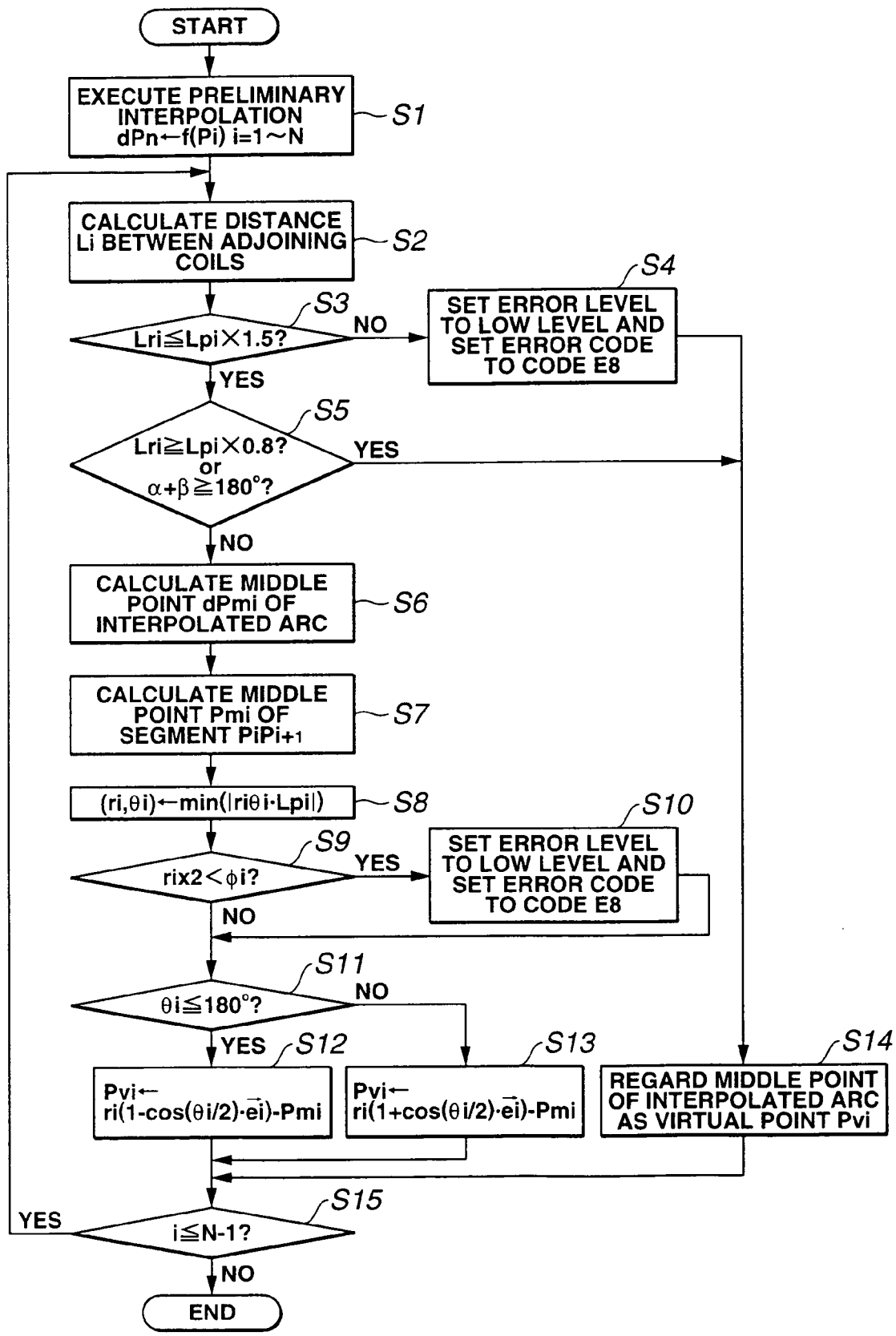

The process will be described with reference to FIG. 12 below. FIG. 12 describes a routine of virtual point designation to be executed as a software program by the virtual point determining means $32c$.

When calculation of a virtual point is started, the CPU 32 executes preliminary interpolation at step S1 in FIG. 12. Interpolation is performed using estimated coil positions Pi in order to calculate interpolated points dPn. Herein, i denotes numbers that are assigned to the source coils $41i$ actually disposed in the insertion portion 7 and that ranges from 1 to N (N denotes, for example, 12 or 16). n denotes the number of points interpolated using the positions i and i+1.

Figure 13:
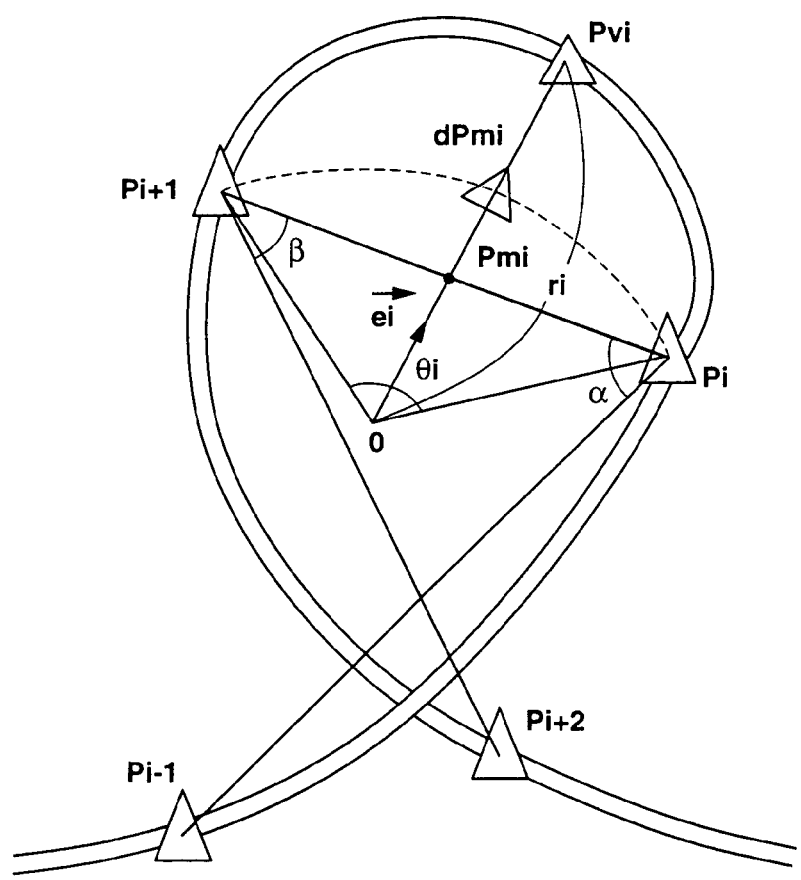

Incidentally, if a position of a source coil is thinned in error, the position is compensated with a middle point of an arc resulting from interpolation performed using the positions of preceding and succeeding source coils (hereinafter, coil positions). Consequently, interpolated points (interpolated point string) indicated with a dashed line in FIG. 13 are calculated between the coil positions Pi and Pi+1.

At the next step S2, the distance between adjoining coils (determined with the interpolated points dPn) is calculated as a distance Lri. At the next step S3, it is judged whether the distance Lri between adjoining coils is equal to or smaller than a predetermined value calculated by multiplying a predetermined value Lpi (specifically, the designed length 100 mm between adjoining coils) by a predetermined coefficient (herein 1.5). In other words, it is judged whether $Lri \leq Lpi \times 1.5$ is established.

If the judgment made at step S3 demonstrates that the condition of $Lri \leq Lpi \times 1.5$ is not met, it is judged that the calculated distance Lri between adjoining coils is too large. Error handling of step S4 is then executed, and control is passed to step S14. During the error handling, an error level is judged to be low. For example, an error code E8 is presented. In this case, the portion of a scope model rendered through interpolation is displayed in, for example, yellow.

On the other hand, if it is judged at step S3 that $Lri \leq Lpi \times 1.5$ is met, it is judged that the calculated distance Lri is equal to or larger than the smaller predetermined value. More particularly, it is judged whether $Lri \geq Lpi \times 0.8$ is met. If the condition is met, the distance Lri between adjoining coils calculated through interpolation is judged to be normal. Control is then passed to step S14.

Moreover, at step S5, assuming that the positions of source coils are, as shown in FIG. 13, Pi−1, Pi, Pi+1, and Pi+2, an angle Pi−1, Pi, Pi+1 and an angle Pi, Pi+1, Pi+2 shall be angles α and β respectively. It is then judged whether α+β is equal to or larger than 180° (that is, $\alpha+\beta \geq 180°$ is met).

If the condition is met, it is judged that at least the three coil positions lie on an arc (loop). In other words, it is judged that a shape approximating the actual shape can be calculated by merely performing normal interpolation. Control is then passed to step S14.

At step S14, a middle point in the distance Li between adjoining coils determined with the interpolated points dPn calculated through preliminary interpolation is designated as a virtual point Pvi. Control is then passed to step S15.

On the other hand, if it is judged at step S5 that Lri≧Lpix 0.8 is not met or α+β≧180° is not met, it is judged that the shape of the insertion portion cannot be calculated highly precisely through the interpolation. The interpolated points are corrected and virtual points are calculated.

First, at step S6, a middle point of an arc determined through interpolation is calculated and regarded as a point dPmi.

Specifically, a middle point dPmi of an arc that is determined through interpolation achieved using the coil positions Pi and Pi+1 and that is indicated with a dashed line in FIG. 13 is calculated.

At the next step S8, a middle point of a segment PiPi+1 is calculated and regarded as a point Pmi. An actual arc is, as shown in FIG. 13, regarded to lie on an extension of a vector drawn from the middle point Pmi of the segment PiPi+1 to the middle point dPmi of the arc (FIG. 13 shows a unit vector ei starting with an initial point O instead of a vector itself).

In order to calculate a middle point of the arc that lies on the extension of the vector ei, the distance between the middle point of the arc and the center O of the arc, that is, the radius ri of the arc, and a central angle θi that is an angle PiOPi+1 are calculated according to the least squares method so that a difference between the length of the arc PiPi+1 and a predetermined distance Lpi will be minimized. At step S8, coordinates (ri, θi) are determined.

Thereafter, at step S9, it is judged whether a double of the calculated radius ri, that is, the diameter of the arc falls below a predetermined minimal diameter φi. The minimal diameter φi is calculated by dividing a minimal radius of a loop, which is formed actually by the insertion portion 7, by a certain coefficient (for example, 1.5).

Consequently, if the condition is met at step S9, it is judged that an error has occurred. The error handling of step S10 is executed. Thereafter, control is passed to step S11 similarly to a case where the condition is not met at step S9. Specifically, the calculated radius ri is regarded to be smaller than the minimal radius measured when the insertion portion 7 is actually looped. Consequently, the radius is regarded to be little reliable, and the portion of a scope model having the radius is displayed in yellow.

When a range of detection falls outside the system of coordinates for inference, nothing is displayed.

At step S11, it is judged whether the central angle θi is equal to or smaller than 180°. It is judged whether the virtual point Pvi lies on the extension of the unit vector ei shown in FIG. 13 or lies on a side opposite to the extension of the unit vector ei.

If the central angle θi is equal to or smaller than 180°, the virtual point Pvi is determined as outlined at step S12. If the central angle θi is equal to or larger than 180°, the virtual point Pvi is determined as outlined at step S13.

Thereafter, it is judged whether the coil number i has reached N−1 adjoining the last number N. If a virtual point to be calculated remains, control is returned to step S2 and the foregoing processing is repeated.

Owing to the processing, after virtual point designation is executed, the virtual points are used together with the positions of the actual source coils 14$i$ to perform interpolation. Thus, the shape of the insertion portion is calculated, and the calculated shape of the insertion portion is adopted as a model and displayed on the display screen of the monitor 25. Thus, when the virtual points are designated, data interpolation required to calculate the shape of the insertion portion later becomes easy to do.

As shown in FIG. 9C and FIG. 10C, even when the insertion portion is bent like a loop at a small curvature, as if numerous source coils were incorporated in the insertion portion, the shape of the insertion portion can be calculated with high precision and displayed.

According to the present embodiment, software is installed in order to dispose a virtual source coil between actually adjoining source coils in such a manner that an appropriate condition will be met. The shape of the insertion portion is then detected and displayed. The present embodiment can therefore be adapted to an existing endoscopic system merely by modifying the software installed in the system according to the present embodiment.

Consequently, once a shape detection program installed in an existing endoscopic system is replaced with the one employed in the present embodiment, the shape of an insertion portion can be detected with high precision and displayed.

Moreover, the number of source coils incorporated in the probe 15 disposed in the insertion portion 7 need not be increased. Consequently, there are the merits that the probe 15 will not be complex, the number of signal lines need not be increased, and the configuration of a driving means need not be modified. In short, the shape of the insertion portion 7 can be detected with high precision despite a simple configuration and displayed.

Incidentally, the source coils 14$i$ are described to be disposed as magnetic-field generating elements, which induce magnetic fields, in the insertion portion 7. The sense coils 22$j$ serving as magnetic-field detecting elements that detect magnetic fields are described to be disposed in the external coil unit 23. Alternatively, the sense coils may be disposed in the insertion portion 7 and the source coils may be disposed in the coil unit 23. Nevertheless, when virtual points are designated among the sense coils as mentioned above, (as if numerous sense coils were disposed in the insertion portion 7), the shape of the insertion portion can be detected highly precisely.

The present embodiment includes other various facilities described below.

Figures 14, 15:
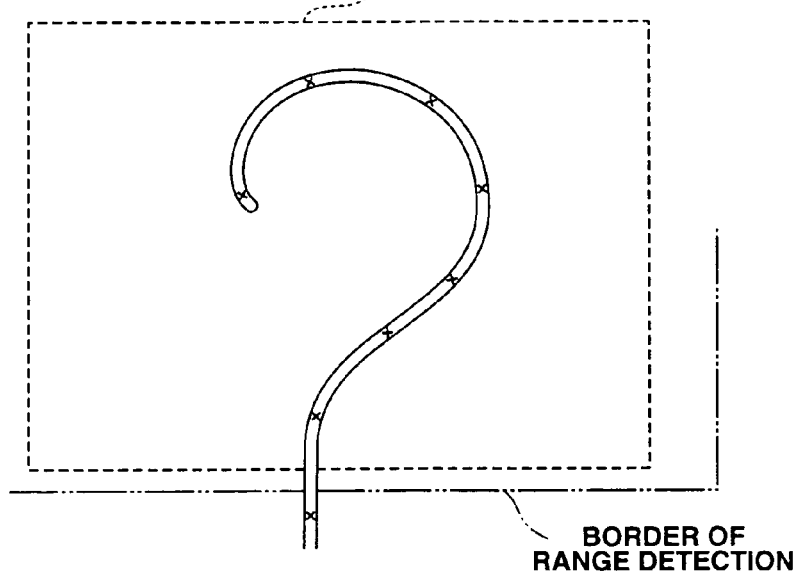

As shown in FIG. 14, the shape-of-endoscope detecting system in accordance with the present embodiment is delivered to five destinations, that is, Japan, the U.S.A, Britain, France, and Germany. Depending on the destination, settings such as an indication of a date, a font, and a symbol (icon) are varied.

The indication of a date is varied depending on the destination, so that an easy-to-see display screen image can be provided for each destination.

Moreover, according to the present embodiment, part of the source coils 14$i$ disposed as shown in FIG. 15 within a range within which an entity is visualized and the image of the entity is displayed on the monitor 25 is used to determine a display color in which an icon expressing an endoscope as shown in FIG. 8A is determined.

Before an improvement is made, if the source coils 14$i$ incorporated in the insertion portion (of the endoscope) lie outside a range of detection, the icon expressing the endoscope is displayed in yellow. The shape of a portion of the insertion portion lying within the range of detection is displayed in gray on the monitor 25. Thus, the displayed shape of the insertion and the icon are rendered in different display colors.

In the present embodiment, the difference between display colors is resolved. The display color in which an icon is displayed is determined depending on whether a portion of the source coil 14*i* to be visualized for display on the monitor 25 lies within the range of detection. Consequently, as shown in FIG. 15, the shape of the insertion portion is displayed in gray because the portion of the insertion portion concerned lies within the range of detection, and the icon is displayed in green. Thus, easy-to-understand display is achieved. Incidentally, the same display method is adopted for the external marker and reference plate.

Moreover, before an improvement is made, the display color in which the shape of the insertion portion is displayed is determined as mentioned below. Namely, when the position of a certain coil lies outside a range of detection, the position of the adjoining coil (actually lies within the range of detection) is calculated using the position information of the coil lying outside the range of detection. Therefore, a portion of an insertion portion near the position of the coil lying within the range of detection may also be displayed in yellow.

In this display, the insertion portion is displayed using a color that reliably expresses an inserted state. There is however the demerit that the border of the range of detection is hard to grasp. According to the present embodiment, a display color is determined based on interpolated points defining the border of the range of detection.

Figure 16:
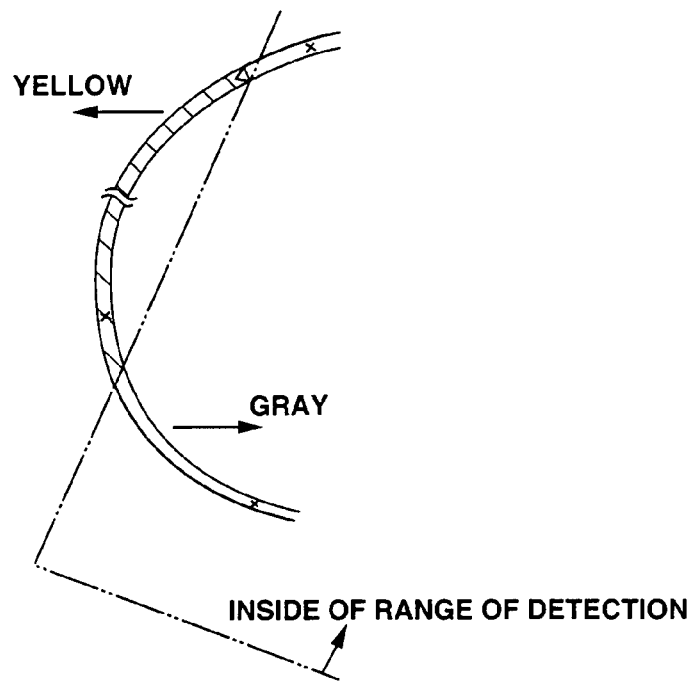

For example, assume that a scope model is, as shown in FIG. 16, calculated to express the insertion portion crossing the border of the range of detection. Herein, a portion of the scope model is defined with two of a plurality of interpolated points calculated using the coil positions indicated with crosses. The two interpolated points are indicated with triangles and express the points on the insertion portion located near the border of the range of detection. The portion of the scope model defined with the triangular interpolated points is displayed in yellow because the corresponding portion of the insertion portion lies outside the range of detection. The other portion of the scope model beyond the triangular interpolated points is displayed in gray because the corresponding portion of the insertion portion lies within the range of detection. Thus, the border of the range of detection is easily grasped owing to the display colors.

Moreover, according to the present embodiment, the timing of buffering position data is changed in order to smooth the movement of a scope model as described below.

Figure 17:
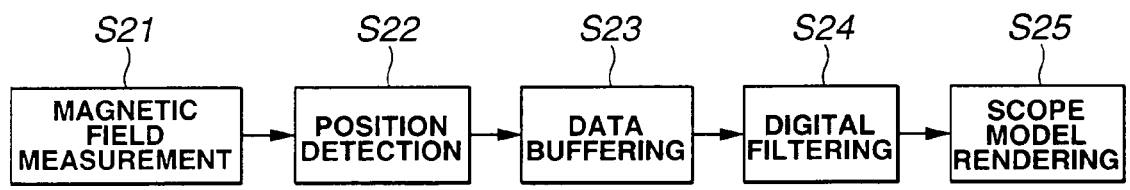

FIG. 17 describes a process of rendering a scope model that starts with measurement of magnetic fields. Namely, magnetic field measurement of step S21 is succeeded by position detection of step S22. Data buffering is executed at step S23 in order to fetch detected position data. Digital filtering is performed on buffered data at step S24. Thereafter, a scope model is rendered at step S25.

Figure 18:
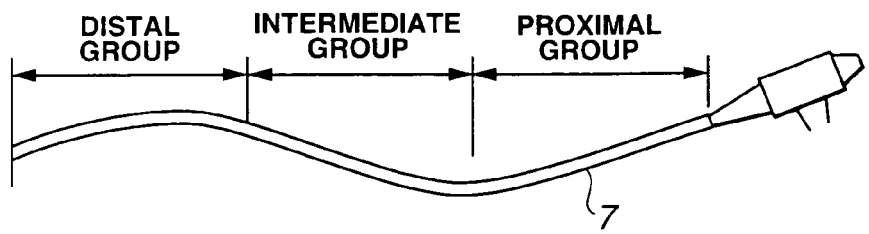
Figure 19A:
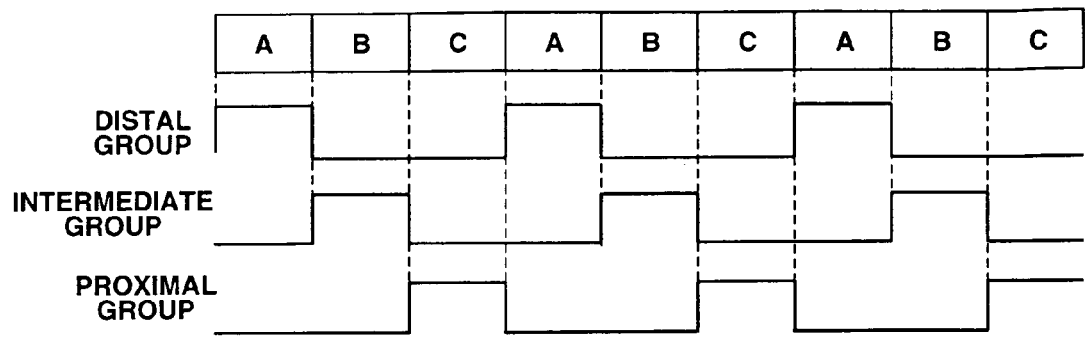
FIG. 19A and FIG. 19B are explanatory diagrams concerning buffering of data to be performed at intervals of a short time in comparison with FIG. 19C concerning buffering performed in a related art.

In this case, as shown in FIG. 18, the coils incorporated in the insertion portion 7 are divided into three groups of coils, that is, a distal group, an intermediate group, and a proximal group. As shown in FIG. 19A, the distal group, intermediate group, and proximal group are sequentially driven at timings A, B, C, A, etc.

In this case, the groups of coils are driven in a time-sharing manner in order to generate a larger number of magnetic fields within a limited frequency band.

Figure 19B:
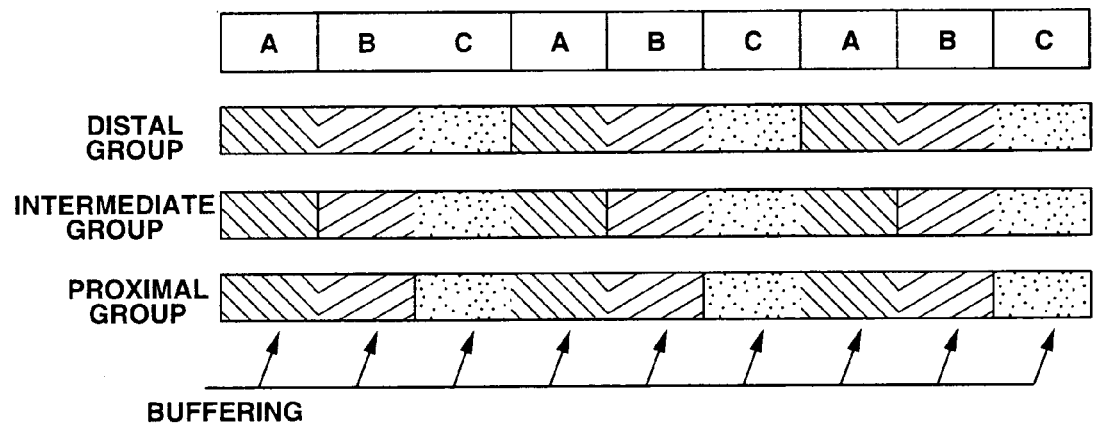

As shown in FIG. 19B, data is buffered at the timing at which data concerning one group of coils to be driven at the same time is updated.

Figure 19C:
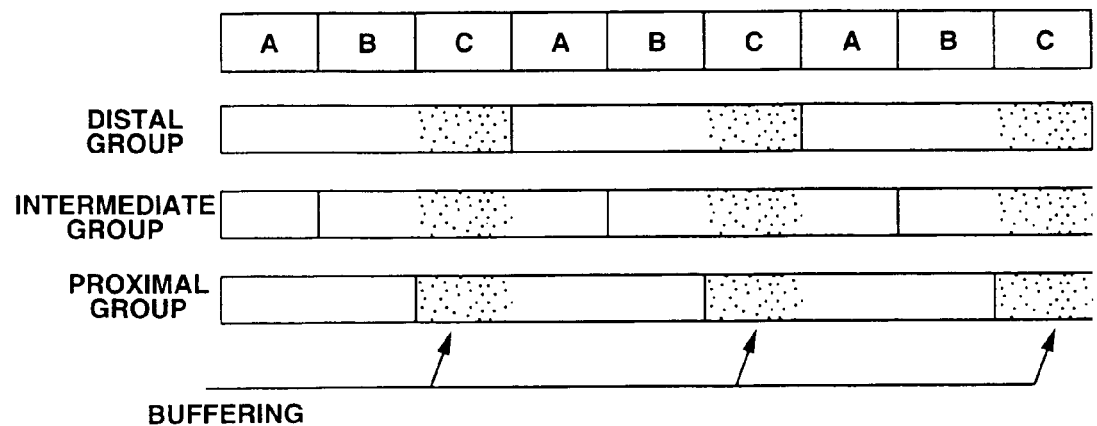

In contrast, according to a related art, data is, as shown in FIG. 19C, buffered at the timing at which data items concerning all the groups of coils are updated (that is, updated at the timing that comes at intervals of a three times longer time).

According to the present embodiment, the updating rate at which data is updated is three times higher. Output data of a digital filter in a succeeding state is updated at intervals of a one-third of the time at intervals of which it is updated conventionally. Consequently, a frame rate for a scope model is triplicated, and the scope model is rendered to move smoothly.

Next, a description will be made of a case where when the reference plate 58 is used, if scope positioning and storage is designated, the positional relationship between the scope model and the main apparatus is presented in an easy-to-understand manner. Thus, an easy-to-see display screen image (scope model) can be provided.

Figures 20, 21:
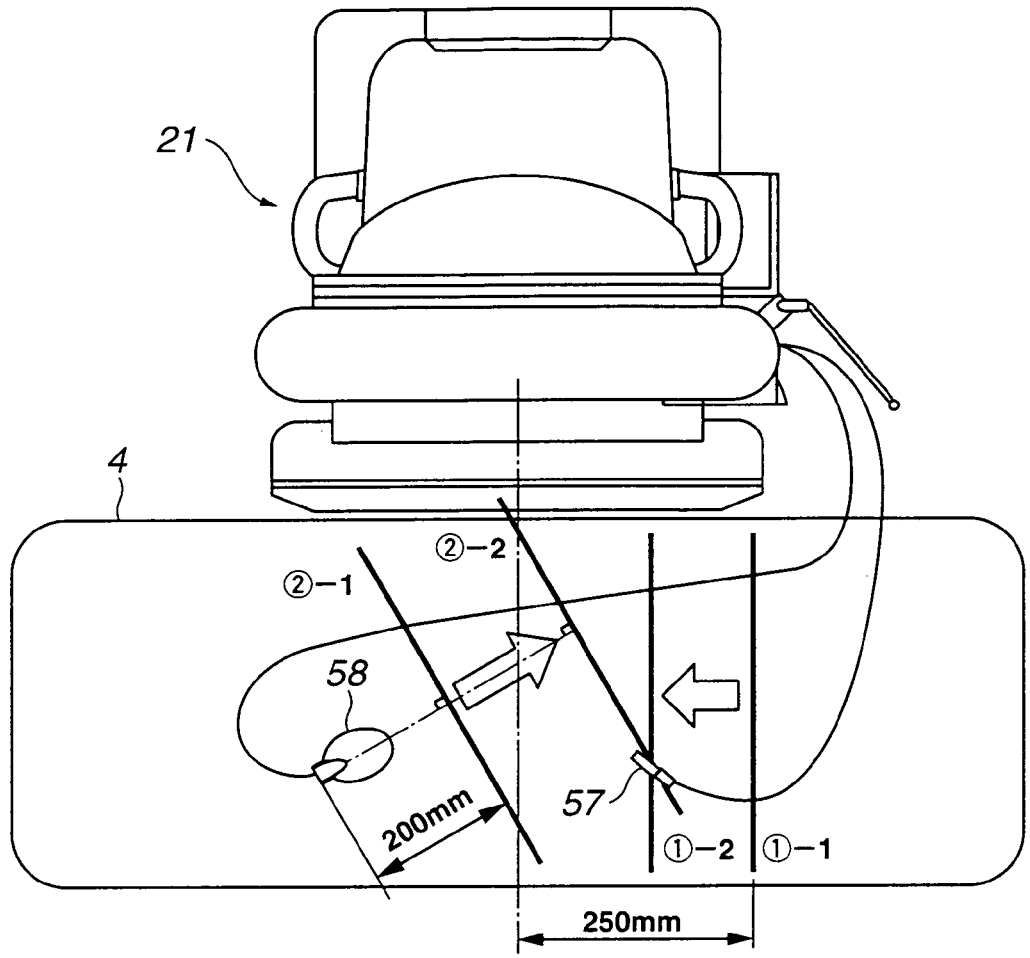

FIG. 20 is the top view of the main apparatus 21 and the bed 4 on which a patient lies down, wherein the patient's head normally comes on the left side of the drawing.

The border between the interior of a patient body (displayed on the monitor 25) and the exterior thereof is defined with a plane that is called a cutting plane. The exterior of the patient body beyond the cutting plane is not displayed.

An existing cutting plane is designated according to whether the reference plate 58 is connected. When the reference plate 58 is unconnected, a cutting plane (1)-1 shown in FIG. 20 is designated. When the reference plate 58 is connected, a cutting plane (2)-1 is designated.

Scope positioning is a facility for shifting the position of the existing cutting plane in parallel (lateral directions in FIG. 20) using the external marker 57. When the scope positioning facility is activated, the cutting plane is moved in parallel to the position (1)-2 or (2)-2.

Moreover, the cutting plane is designated as listed in the table of FIG. 21 according to the use states of the reference plate 58 and external marker 57. In the table, "valid" and "invalid" signify whether the use of the detected position of the connected reference plate 58 or external marker 57 is valid or invalid.

Assuming that the reference plate 58 is connected, a plane perpendicular to a plane defined with the reference plate 58 is regarded as a cutting plane. Conventionally, when the external marker 57 is activated, the cutting plane is designated in a different azimuth from the cutting plane (2)-1 that is designated when the reference plate 58 is connected. According to the present embodiment, (when the reference plate 58 is connected, the azimuth of the cutting plane is left unchanged.), the cutting plane is moved in parallel up to the position (2)-2 so that it will pass through the external marker 57. Thus, the capability of the reference plate 58 can be easily grasped.

Moreover, according to the present embodiment, a method of displaying a gray scale for a scope model that is adopted for a related art is modified. According to the related art, a full gray scale of shades is assigned to an image containing a scope model. For example, even if the scope model is nearly a plane, part of the scope model may be extremely bright or dark. From this viewpoint, a gray scale described below is adopted.

A portion of a scope model that need not be displayed to attract attention and that is rendered based on data of normal source coils is colored according to a gray scale. At this time, the gray scale is determined so that the shades will get darker from a point in a screen image, which is rendered to exist nearest, toward a point in the screen image which is rendered to exist deepest (in the direction of a Z axis in the system of coordinates representing a field of view). A change rate γ is calculated according to an expression below.

$$\gamma = \sin \theta/2 \times (Cmax - Cmin) + Cmin$$

$$\theta = (Z - Zmin)/(Zmax - Zmin) \times \lambda - \lambda/2$$

where Cmin denotes red, green, and blue values determining the darkest shade (256 gray-scale levels), Cmax denotes red, green, and blue values determining the brightest shade (256 gray-scale levels), Zmin denotes a z coordinate representing the point in the screen image that is rendered to exist deepest according to the gray scale, and Zmax denotes a z coordinate representing the point in the screen image that is rendered to exist nearest according to the gray scale.

According to the related art, the gray scale is determined according to an actually detected range of an endoscope. In contrast, according to the present embodiment, the gray scale is determined based on a fixed value such as a defined range of detection. Consequently, a scope model will not be displayed with shades have large differences. Instead, the scope model is displayed according to a gray scale that allows a user to easily grasp the three-dimensional shape of the insertion portion.

When a scope model is displayed on the monitor 25, an automatic centering facility efficiently prevents the scope model from coming out of a screen so that an easy-to-see display screen image can be provided. According to the present embodiment, when a user changes the horizontal-direction edge of a screen image (for example, when a user inactivates the scope positioning facility, or connects or disconnects the reference plate), the automatic centering facility is activated without fail. This is intended to prevent a scope model from coming out of the screen.

Figure 22A:
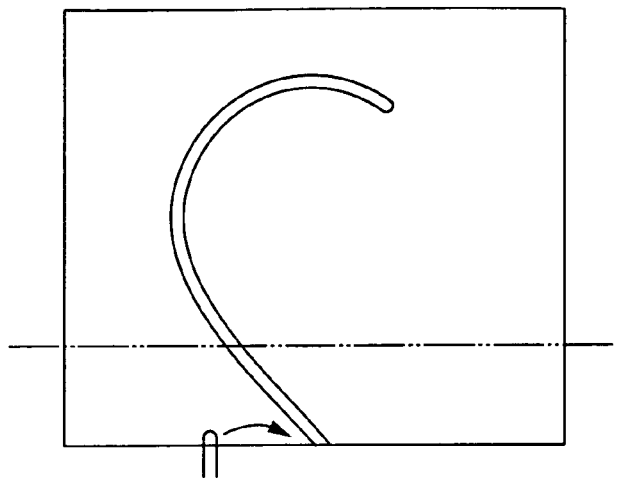

When the distal end of a scope model enters an upper display area, as shown in FIG. 22A, a normal centering facility adjusts a horizontal line on a display screen image so that the distal end of the scope model will come to the center in the horizontal direction of the display screen. Thus, the scope model is displayed.

Referring to FIG. 22A, for example, the distal end of a scope model crosses the lower horizontal edge of a screen image, which indicates a cutting plane, on the left side of the center of the lower horizontal-direction edge of the screen image. The scope model is displayed almost in the center of the screen.

In this state, assume that the cutting plane is moved to a position corresponding to a position indicated with an alternate long and two short dashes line in FIG. 22A using the external marker 57. In this state, a portion of a scope model expressing a portion of the insertion portion located above the position of the cutting plane is displayed. The point on the scope model at which the scope model crosses the horizontal edge of a screen image indicating the cutting plane does not meet the center of the lower horizontal-direction edge of the screen image. Therefore, the position of the scope model is corrected by the automatic centering facility. Consequently, the point on the scope model at which the scope model crosses the horizontal edge indicating the cutting plane is, as shown in FIG. 22B, set to the center of the lower horizontal-direction edge of the screen image.

In this state, if the use of the external marker 57 is stopped (the external marker 57 is removed or the scope positioning facility is inactivated), the automatic centering facility is activated so that the position of the scope model on the lower edge of the screen image will be set to the center in the horizontal direction. Herein, the lower edge of the screen image indicates the cutting plane designated with the external marker 57 unused. Namely, the scope model is displayed as indicated with a solid line in FIG. 22C.

Figure 22B:
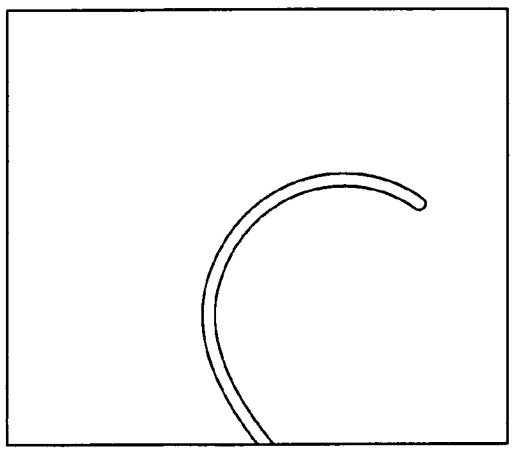
Figure 22C:
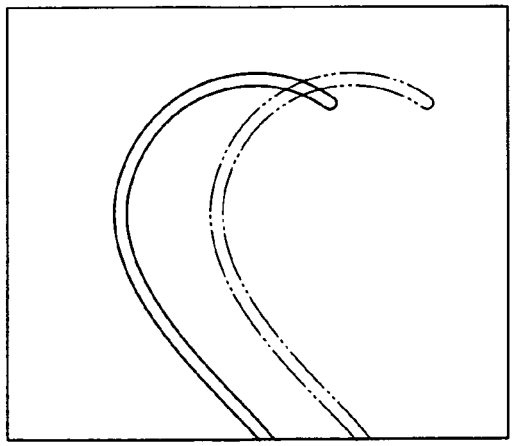

In contrast, before an improvement is made, the position of the scope model shown in FIG. 22B is, as indicated with an alternate long and two short dashes line in FIG. 22C, merely shifted to a position attained when the cutting plane has not been moved.

In short, before an improvement is made, a point on a scope model at which the scope model crosses the lower horizontal edge of a screen image does not meet the center of the lower edge.

According to the present embodiment, even in this case, the automatic centering facility is activated so that the state indicating the scope model is maintained by resetting to the center of the screen image as indicated in a solid line. Herein, a description has been made on the assumption that the automatic centering facility is activated with the start or stop of the use of the external marker 57. The automatic centering facility is also activated with the connection or removal of the reference plate.

As mentioned above, a scope model can be effectively prevented from coming out of a screen image.

In the above description, the number of sense coils $22j$ disposed in the coil unit 23 is 12. The present invention is not limited to the number of sense coils of 12. Alternatively, the number of sense coils may be, for example, 16.

As described previously, according to the present embodiment, a shape-of-endoscope detecting system has one of pluralities of magnetic-field generating elements and magnetic-field detecting elements disposed in an endoscope insertion portion. The other of the pluralities of magnetic-field generating elements and magnetic-field detecting elements is disposed outside a subject. A detecting means detects the positions of one of the pluralities of elements disposed in the endoscope insertion portion using position data concerning the other of the pluralities of elements. Thus, the shape of the endoscope insertion portion is inferred and displayed on a display means. In the shape-of-endoscope detecting system, based on an output of the detecting means, virtual elements are disposed among one of the pluralities elements whose positions are detected. A data interpolating means interpolates data using position data items of the virtual elements disposed among one of the pluralities of elements. Even if the endoscope insertion portion is bent at a small curvature, as if the number of actually disposed elements were increased, the shape of the bent insertion portion can be detected highly precisely and then displayed.

Second Embodiment

Figure 23:
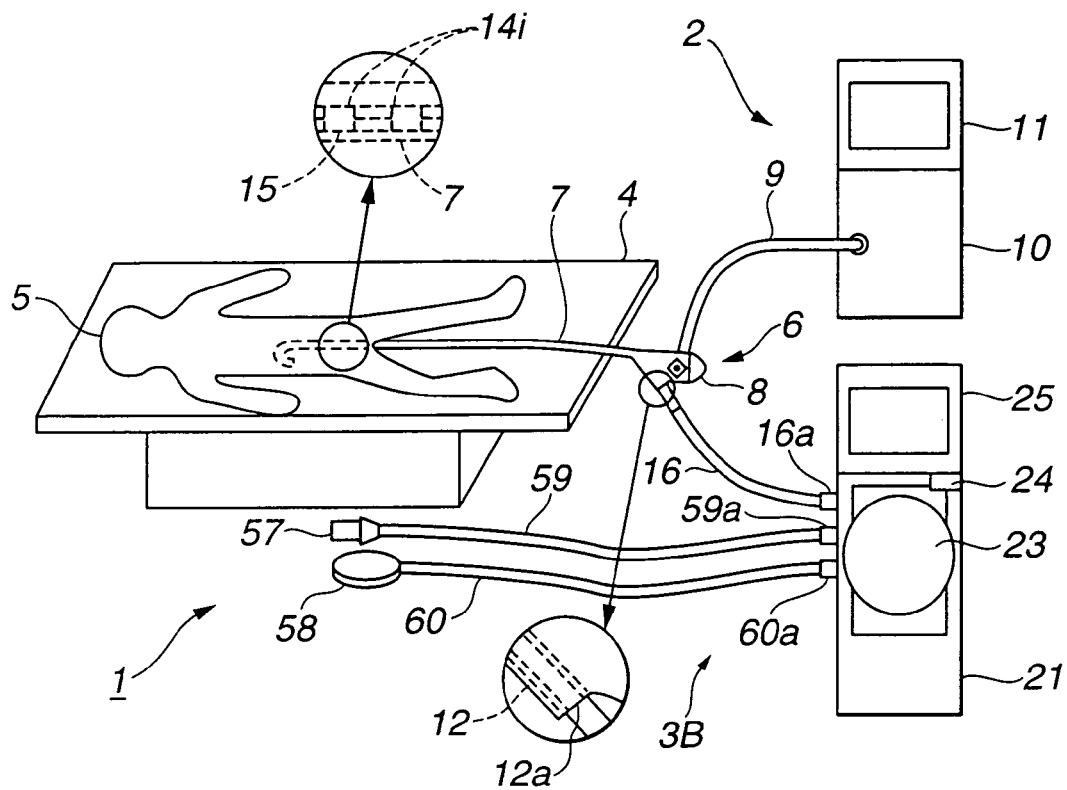

Next, a second embodiment of the present invention will be described with reference to FIG. 23 to FIG. 35. An object of the present embodiment is to provide a shape-of-endoscope detecting system capable of detecting the shape of an endoscope in an environment little affected by a noise. FIG. 23 shows the configuration of an endoscopic system 1B including the present embodiment. The endoscopic system 1B has the same configuration as the endoscopic system 1 shown in FIG. 1 except a shape-of-endoscope detecting system 3B. The same reference numerals will be assigned to identical components, and the description of the components will be omitted.

Figure 24:
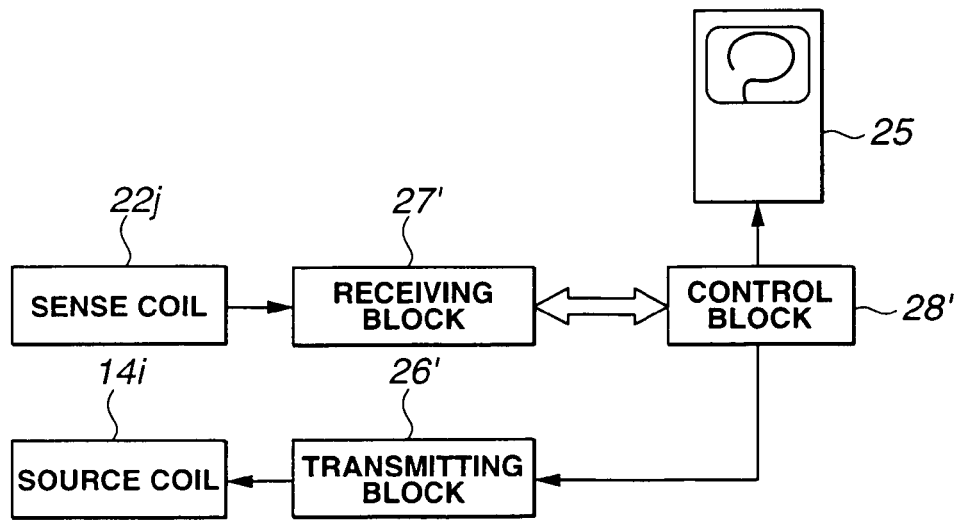

The shape-of-endoscope detecting system 3B in accordance with the present embodiment comprises: as shown in FIG. 24, a transmitting block 26' that drives the source coils $14i$; a receiving block 27' that receives signals from the sense coils 22*j* incorporated in the coil unit 23; and a control block 28' that processes the signals detected by the receiving block 27'.

The shape-of-endoscope detecting system 3B shown in FIG. 24 includes the transmitting block 26' on behalf of the driving block 26 included in the shape-of-endoscope detecting system 3 shown in FIG. 3. Moreover, the shape-of-endoscope detecting system 3B includes the receiving block 27' on behalf of the detecting block 27, and the control block 28' on behalf of the host processor 28.

As shown in FIG. 25A, the probe 15 disposed in the insertion portion 7 of the electronic endoscope 6 has, as mentioned above, the sixteen source coils 14*i*, which generate magnetic fields, arranged therein at predetermined intervals. The source coils 14*i* are connected to the source coil drive circuit 31 that produces sixteen driving signals whose frequencies are different from one another and that is included in the transmitting block 26.

The source coil drive circuit 31 drives the source coils 14*i* using the driving signals of sine waves having different frequencies. The frequencies of the driving signals are determined based on driving frequency determination data (or driving frequency data) stored in a driving frequency determination data memory means or a driving frequency determination data memory means that is not shown and that is included in the source coil drive circuit 31. The driving frequency data is stored in the driving frequency data storage means (not shown) included in the source coil drive circuit 31 via the parallel input/output (PIO) circuit 33 by means of the central processing unit (CPU) 32 that calculates the shape of the endoscope and that is included in the control block 28.

As described later, a plurality of groups of driving signals having different frequencies is predefined. Before the positions of the source coils are actually detected, an ambient noise is measured. Based on the results of the measurement, a group of driving signals having different frequencies which has caused the lowest ambient noise can be selected and designated.

On the other hand, the twelve sense coils 22*j* incorporated in the coil unit 23 are connected to the sense coil signal amplification circuit 34 included in the receiving block 27.

As shown in FIG. 5, twelve single-core coils 22*k* serving as the sense coils 22*j* are connected to the amplifiers 35*k* included in the sense coil signal amplification circuit 34. Thus, twelve processing systems are constructed. Feeble signals detected by the single-core coils 22*k* are amplified by the respective amplifiers 35*k*, and have unnecessary components thereof removed by the respective filters 36*k* that pass a plurality of frequencies generated by the group of source coils. The resultant signals are transmitted to the respective output buffers 37*k*, and converted into digital signals readable by the control block 28 by means of the respective analog-to-digital (A/D) converters 38*k*.

Incidentally, the receiving block 27 comprises the sense coil signal amplification circuit 34 and the A/D converters 38*k*. The sense coil signal amplification circuit 34 comprises the amplifiers 35*k*, filters 36*k*, and output buffers 37*k*.

Referring back to FIG. 25A, the outputs of the twelve systems included in the sense coil signal amplification circuit 34 are transferred to the twelve A/D converters 38*k*, and converted into digital data items that are sampled at a predetermined sampling rate according to a clock sent from the control signal generation circuit 40 incorporated in the control block 28'. The digital data items are written in the two-port memory 42 over the local data bus 41 in response to a control signal sent from the control signal generation circuit 40.

In the present embodiment, the connector 16*a* and connector receptacle 21*a*, the connector 59*a* and connector receptacle 21*b*, and the connector 60*a* and connector receptacle 21*c* shown in FIG. 25A are coated in two or three layers with a metal that exhibits a superb property of shielding magnetic fields (for example, a ferromagnetic metal such as a silicon steel). This is intended to reduce a leakage flux or the like so as to alleviate the adverse effect of a leakage flux on a scope model or the adverse effect of a noise on checking.

Moreover, according to the present embodiment, the transmitting block 26' shown in FIG. 24 can provide a plurality of groups of driving signals having different frequencies (for example, three groups G1, G2, and G3 as described later).

When the source coils 14*i* disposed in the insertion portion 7 are driven, a group of driving signals having different frequencies which causes the lowest ambient noise is automatically or manually selected from the three usable groups of driving signals having different frequencies. A scope model can then be calculated. This is the major constituent feature of the present embodiment.

Figure 26:
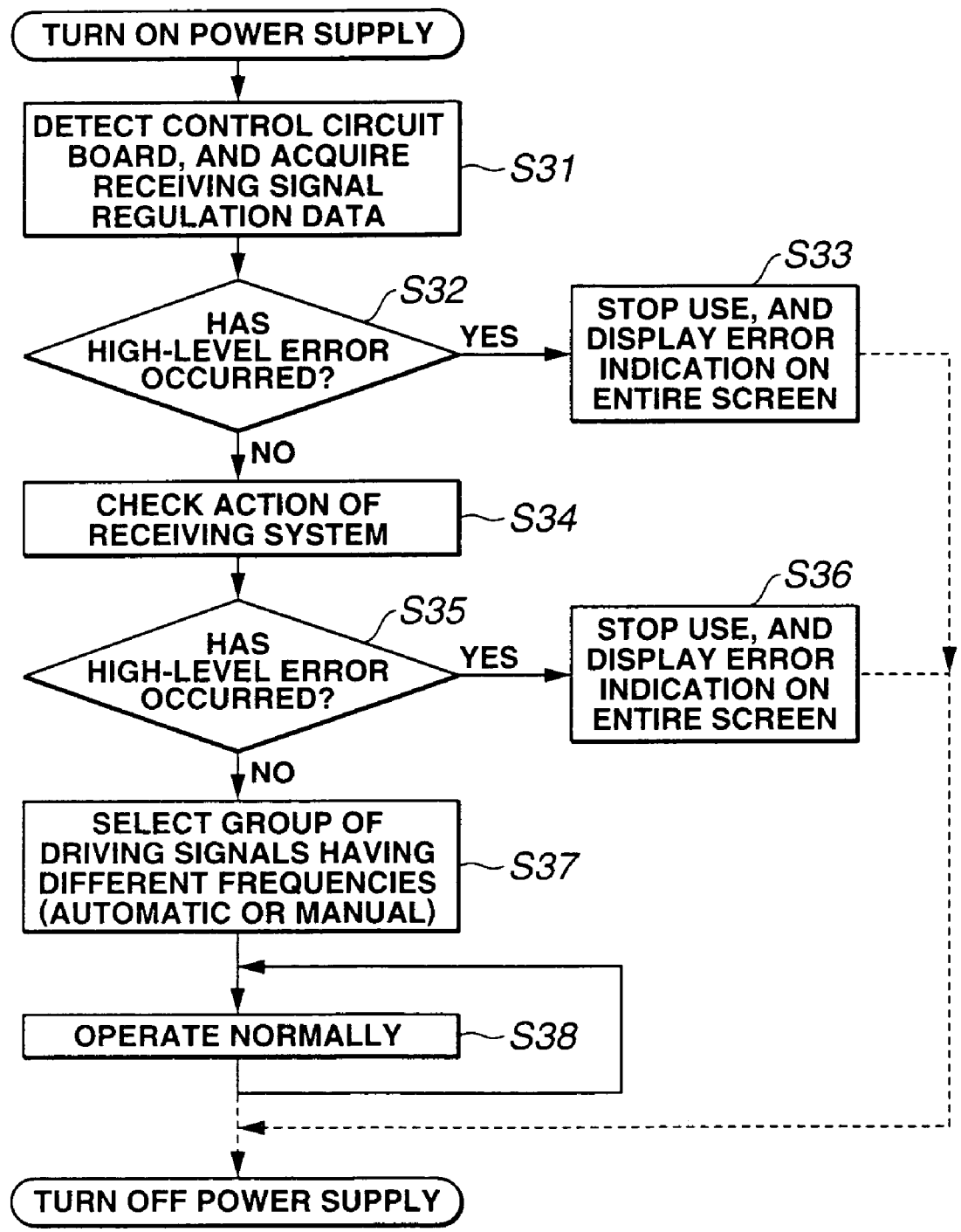

When the power supply is turned on, the CPU 32 incorporated in the detecting apparatus (main apparatus) 21 shown in FIG. 25A executes a process described in FIG. 26 according to a program that is not shown. In this case, before the positions of the source coils are detected normally, an ambient noise is measured. A driving frequency group selecting means 32*d* incorporated in the CPU 32 selects a group of driving signals having different frequencies which causes the lowest ambient noise.

As described later, when automatic selection is designated, the CPU 32 extends control according to a program so that an ambient noise will be automatically measured. Based on the results of the measurement, the CPU 32 judges which of the groups of driving signals having different frequencies causes the lowest ambient noise. The CPU 32 then controls driving (selection and designation) so that the source coils 14*i* will be actually driven with the group of driving signals having different frequencies.

Referring to FIG. 26, an operation to be exerted by the present embodiment will be described below. When the power supply is turned on, the CPU 32 incorporated in the main apparatus 21 detects a control circuit board and acquires receiving system regulation data at step S31.

In order to detect a control circuit board, mapping of a PCI device information table concerning a PCI bus mounted on the control circuit board incorporated in the main apparatus is checked. Moreover, the PCI configuration is checked, and the initial values of registers mounted on the control circuit board are checked. Thereafter, receiving system regulation data is acquired.

At the next step S32, it is judged whether a high-level error has occurred. If so, control is passed to step S33. Use is disabled. For example, an error indication is displayed over the entire screen. In this case, the power supply is turned off and maintenance is performed. According to the present embodiment, an error indication can be selected from a plurality of error indications according to a failure. A screen image to be displayed is varied depending on the contents of an error. Thus, a user can verify from the displayed screen image what kind of default or failure has occurred. This contributes to realization of a user-friendly system.

If it is found at step S33 that a high-level error has not occurred, the action of a receiving system is checked at step S34.

Figure 27:
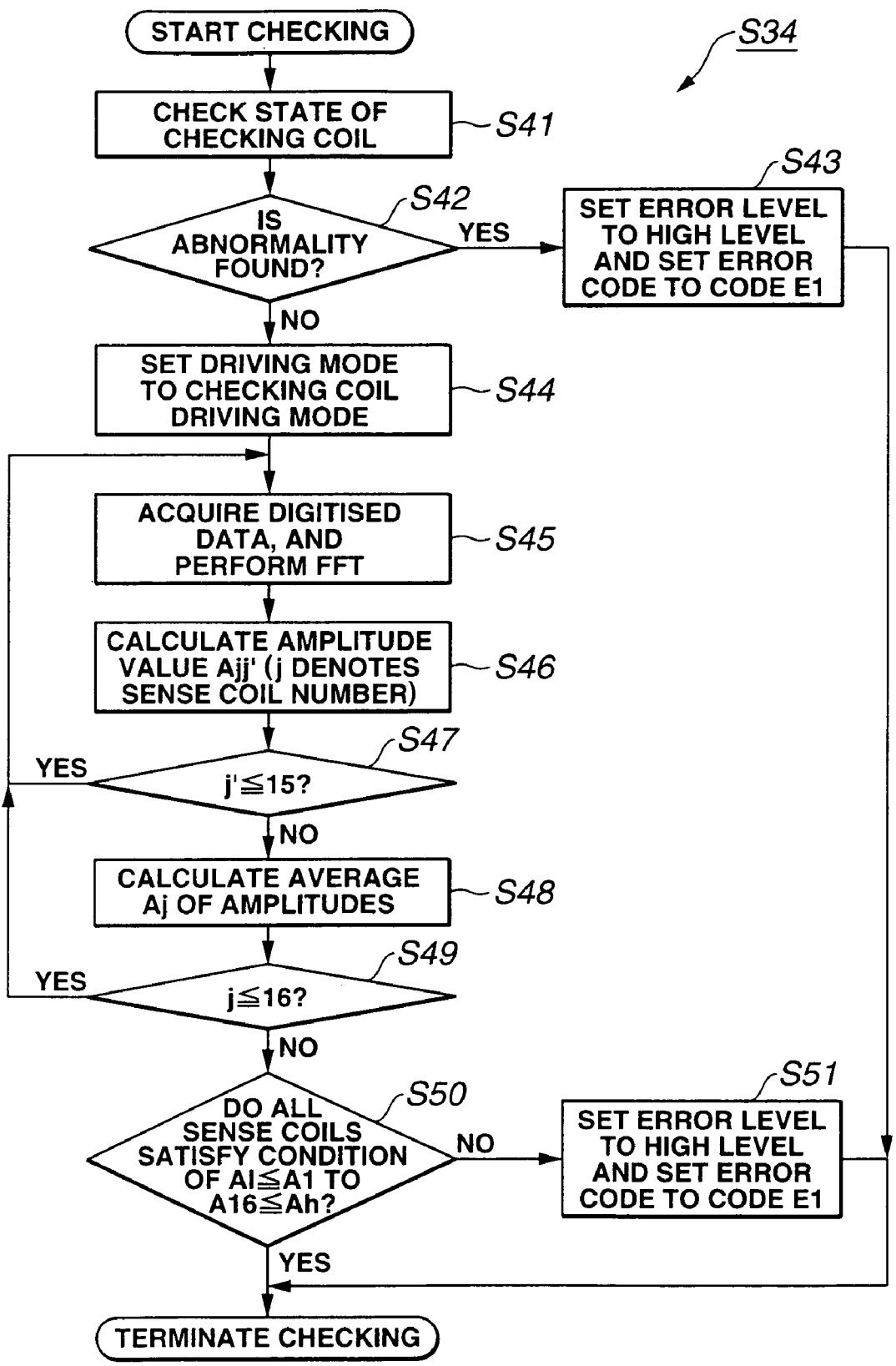

In order to check the action of the receiving system, the state of a check coil (not shown) incorporated in the main apparatus 21 is checked at step S41 described in FIG. 27. For example, the check coil is checked to see if it has failed according to the same method as the source coils are checked as described later to see if they have failed. Thus, the state of the check coil is checked.

At step S42, it is judged whether an abnormality is present. If so, control is passed to step S43. It is indicated that a high-level error has occurred, for example, an error code E1 is indicated. Checking is then terminated.

On the other hand, if no abnormality is found, the check coil driving mode is designated at step S44. The check coil is then driven.

At step S45, data items produced when the check coil is driven and received by the respective sense coils 22j incorporated in the coil unit 23 are digitized in order to inspect the action of the receiving system. Frequency analysis (fast Fourier transformation (FFT)) is then performed on the resultant data items. Consequently, amplitudes Ajj' detected by the sense coils 22j are acquired at step S46. Hereinafter, a description will be made on the assumption that the number of sense coils is sixteen.

In this case, j denotes a sense coil number, and j' denotes the number of times of measurement by which measurement is performed. At the next step S47, it is judged whether j' is equal to or smaller than 15. If j' is equal to or smaller than 15, control is returned to step S45. The same processing is repeated. If j' reaches 16, control is passed to step S48. An average Aj of amplitudes Ajj' resulting from fifteen measurements is calculated.

At the next step S49, it is judged whether j is equal to or smaller than 16. If j is equal to or smaller than 16, control is returned to step S45. The amplitudes detected at all the sense coils 22j are acquired.

When the amplitudes detected at all the sense coils 22j are acquired, it is judged at step S50 whether the amplitudes A1 to A16 detected at all the sense coils 22j fall within a range from an upper limit Ah to a lower limit Al within which the amplitudes are normal.

If the amplitudes fall within the range from the upper limit Ah to the lower limit Al, the amplitudes are judged to be normal. Checking is then terminated. On the other hand, if the condition set at step S50 is not met, control is returned to step S51. For example, an error code E1 is presented in order to indicate that a high-level error has occurred. Then, checking is terminated.

When checking the action of the receiving signal is terminated, control is passed to step S35 described in FIG. 26. At step S35, it is judged whether an error level is high. If the error level is high, control is passed to step S36. Similarly to step S33, use is disabled.

On the other hand, if the error level is not high, control is passed to step S37. Control is passed to selection of a group of driving signals having different frequencies. Thereafter, normal processing of step S38 is performed. Namely, a group of driving signals having different frequencies that causes the lowest ambient noise (designated automatically) (or a group of driving signals having different frequencies that is designated manually) is used to drive the source coils. The positions of the source coils are then detected, and a scope model is displayed.

Selecting a group of driving signals having different frequencies at step S37 will be described with reference to FIG. 28.

Figure 28:
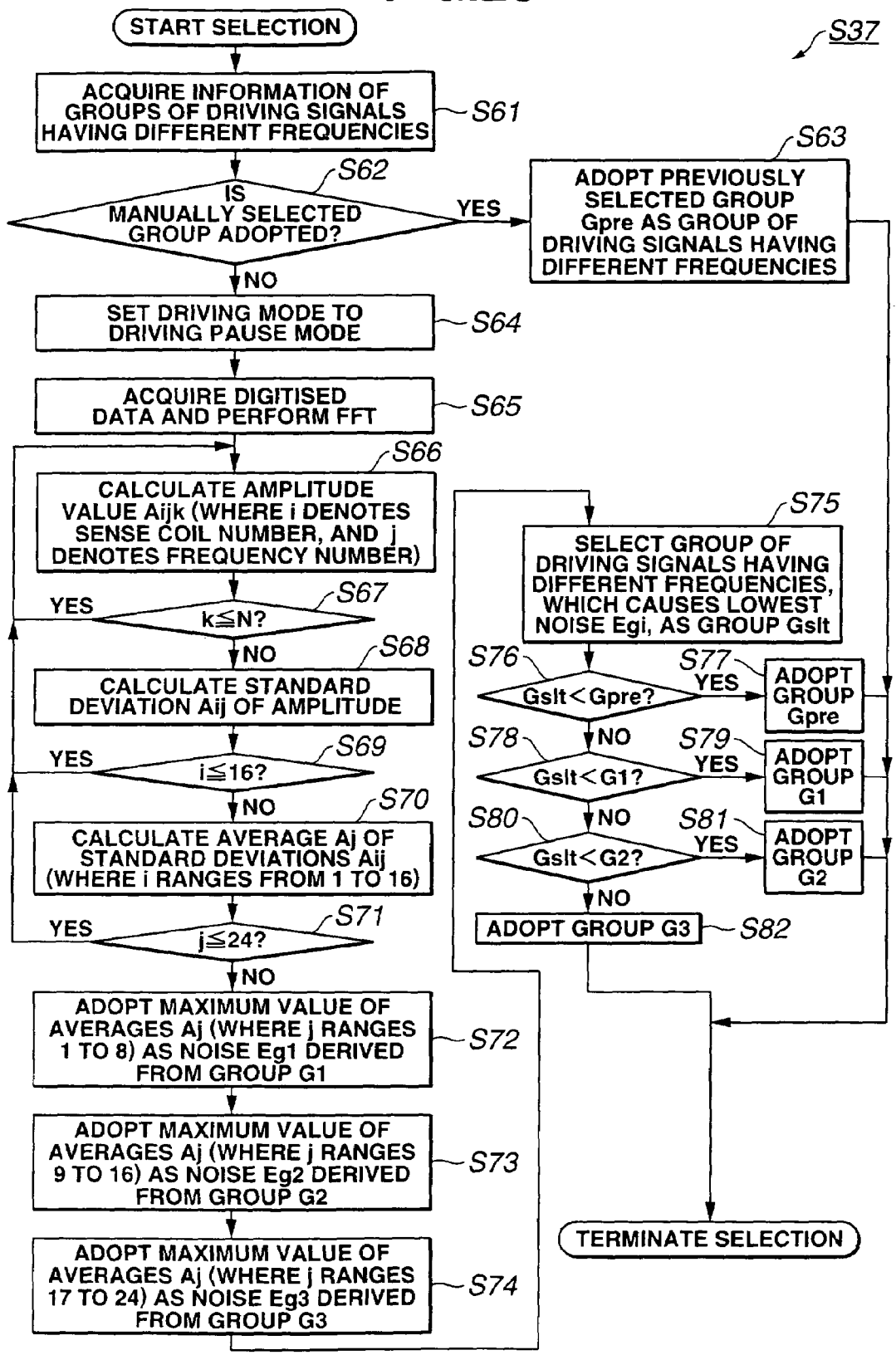

When the processing of step S37 is started, information of groups of driving signals having different frequencies is acquired at step S61 in FIG. 28.

In this case, the information of groups of driving signals having different frequencies is information concerning a currently determined setting, that is, automatic selection or manual selection. Moreover, the information contains a group Gpre of driving frequencies having different frequencies that is selected previously (that may be selected manually) (specifically, one of three groups G1, G2, and G3), and the number of times of measurement N (where N ranges from 10 to 1000 in steps of 10) by which ambient noise is measured.

At step S62, it is judged whether manual selection is designated. If manual selection is designated, control is passed to step S63. The group Gpre previously selected as a group of driving signals having different frequencies is adopted, and the process is terminated.

If a plurality of shape detecting systems is operated simultaneously, manual selection of a group of driving signals having different frequencies may work effectively. For example, a plurality of shape detecting systems is operated with automatic selection designated, the shape detecting systems may select the same group of driving signals having different frequencies. In this case, manual selection would prove useful. Therefore, the present embodiment makes it possible to designate manual selection.

On the other hand, if manual selection is not designated, automatic selection is designated. In this case, the driving mode is set to a driving pause mode (an ambient noise is then measured, and a group of driving signals having different frequencies that causes the lowest ambient noise is automatically selected (controlled)).

At step S64, a state in which the source coils 14i are not driven is established. Specifically, the state of a generator command register mounted on the control circuit board is set to a state in which no driving signal is generated.

In the driving pause state in which the source coils 14i are not driven, measuring an ambient noise is started. As described in conjunction with FIG. 25A, the connectors attached to the main apparatus 21 are magnetically shielded. Therefore, an ambient noise can be measured with a leakage flux from the main apparatus minimized.

In other words, at step S65, signals detected by the sense coils incorporated in the coil unit 23 in the driving pause state are digitized. Frequency analysis is then performed on the resultant digital signals.

At the next step S66, an amplitude Aijk detected by each sense coil and obtained through the frequency analysis is calculated. Herein, i denotes a sense coil number, j denotes a frequency number, and k denotes the number of times of measurement.

At the next step S67, if the number of times of measurement k is equal to or smaller than N, control is returned to step S65. Measurement is then repeated. For example, the present system permits employment of twenty-four driving signals having different frequencies (for driving). The twenty-four driving signals having different frequencies are used to measure amplitudes N times.

After N times of measurement are completed, standard deviations of the amplitudes (which exhibit a time-sequentially varying distribution characteristic) which each sense coil detects with applications of twenty-four driving signals having different frequencies are calculated at step S68. The standard deviations of the amplitudes are regarded as noise values Aij.

At the next step S69, it is judged whether the sense coil number is equal to or smaller than 16. If the sense coil number is equal to or smaller than 16, control is returned to step S65. The same processing is repeated. On the other hand, if the sixteen sense coils have been used to measure amplitudes, control is passed to step S70. An average of noise values Aij that are standard deviations of the amplitudes detected at all the sense coils is calculated relative to the frequency of each driving signal, and regarded as a frequency noise value Aj.

At the next step S71, it is judged whether the frequency number is equal to or smaller than 24. If the frequency number is equal to or smaller than 24, control is returned to step S65. The same processing is repeated.

On the other hand, if amplitudes have been measured by applying twenty-four driving signals having different frequencies, control is passed to step S72. The largest one of frequency noise values Aj calculated relative to frequency numbers 1 to 8 is regarded as a noise value Eg1 caused by the group G1 of driving signals having different frequencies. At the next step S73, the largest one of frequency noise values Aj calculated relative to frequency numbers 9 to 16 is regarded as a noise value Eg2 caused by the group G2 of driving signals having different frequencies. At the next step S74, the largest one of frequency noise values Aj calculated relative to frequency numbers 17 to 24 is regarded as a noise value Eg3 caused by the group G3 of driving signals having different frequencies.

At the next step S75, the noise values caused by the groups of driving signals having different frequencies are compared with one another in order to select a group Gslt that causes the smallest noise value. After the group Gslt causing the smallest noise value is selected, it is judged at step S76 whether the frequencies of the group of driving signals having different frequencies, Gslt, are higher than the frequencies of the group of driving signals having different frequencies, Gpre. If so, control is passed to step S77. The group of driving signals having different frequencies Gpre is adopted as a group of driving signals having different frequencies to be actually applied for driving. Thereafter, selection is terminated.

If the condition set at step S76 is not met, control is passed to step S78. It is then judged whether the frequencies of the group of driving signals having different frequencies, Gslt, are higher than the frequencies of the group of driving signals having different frequencies, G1. If so, control is passed to step S79. The group of driving signals having different frequencies, G1, is adopted as a group of driving signals having different frequencies that is applied for driving. Thereafter, selection is terminated.

If the condition set for step S78 is not met, control is passed to step S80. It is then judged whether the frequencies of the group of driving signals having different frequencies, Gslt, are higher than the frequencies of the group of driving signals having different frequencies, G2. If so, control is passed to step S81. The group of driving signals having different frequencies, G2, is adopted as a group of driving signals having different frequencies that is actually applied for driving. Thereafter, selection is terminated.

If the condition set for step S80 is not met, control is passed to step S82. The group of driving signals having different frequencies, Gp3, is adopted as a group of driving signals having different frequencies that is actually applied for driving. Thereafter, selection is terminated. Thereafter, the selected group of driving signals having different frequencies is used to operate the system normally.

According to the present embodiment, the source coils 14j are driven, the positions of the source coils are detected, and a scope model is calculated. Prior to this process, an ambient noise is detected in order to select a group of driving signals having different frequencies that causes the lowest noise. The selected group of driving signals having different frequencies is actually used to detect the positions of the source coils. Consequently, the positions of the source coils can be detected readily with a high signal-to-noise ratio, that is, with high precision, and a scope model can be calculated in the same manner.

Moreover, before the source coils 14i are driven in order to detect the positions thereof so as to calculate a scope model (more particularly, before an ambient noise is detected), the receiving system, or especially, the sense coils are checked to see if they act normally. If the sense coils act normally, processing required for normal operation is performed. This leads to improved reliability of the shape-of-endoscope detecting system.

Moreover, according to the present embodiment, the shape-of-endoscope detecting system has an improved checking means that when the source cable 16 extending from the rear end of the probe 15 inserted in the endoscope 6 is couple to the main apparatus 21, can sense such an event that a short-circuit occurs in the source cable 16 or imperfect contact (disconnection) occurs at a joint.

Specifically, a failure that cannot be detected previously can be detected by the sophisticated self-checking facility. Thus, a more reliable shape-of-endoscope detecting system is realized.

In order to clarify the constituent features and operation of the present embodiment, the constituent features and operation will be described in comparison with those provided before an improvement is made.

Figure 29:
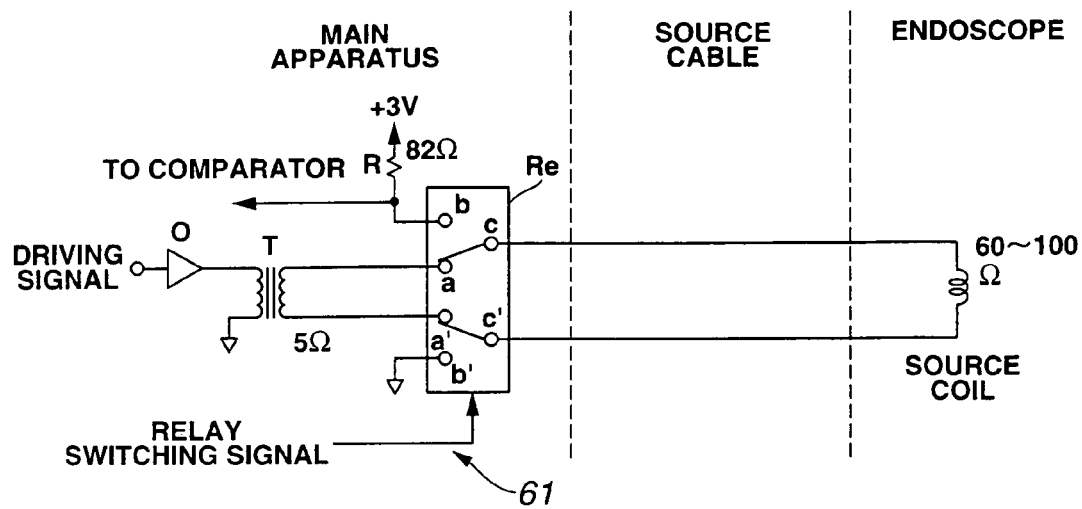

FIG. 29 shows the configuration of a drive circuit 61 designed on the assumption that the number of source coils 14i is one. A driving signal produced in the main apparatus 21 is amplified by an operational amplifier O, and then applied to the primary winding of an output transformer T. The driving signal is then applied from the isolated secondary winding to the source coil 14 (incorporated in the endoscope 6) over the source cable 16 via a relay Re.

When the source coil 14 is driven, contacts a and a' connected to the output transformer T are connected to switching contacts c and c'. Consequently, a driving signal is applied to the source coil 14 over a discrete line, and returned over a common line. Even when driving is stopped, the switching contacts are connected to the contact a and a'.

Moreover, when the source cable is checked to see if a short-circuit has occurred, the states of the relay Re are switched with a relay switching signal that indicates the timing of checking. Consequently, the switching contacts c and c' are connected to a contact b that is connected to one terminal of a checking resistor R and to a contact b' that is grounded.

The other terminal of the register R is connected to a power terminal (where a voltage of +3 V is developed). One terminal of the register R is connected to a comparator that is not shown. The voltage at the one terminal of the register R is detected and checked to see if the voltage falls within a predetermined range. Thus, occurrence of a short circuit or a break (disconnection) is checked.

The checking register R provides the dc resistivity of about 82Ω, and the source coil 14 provides the dc resistivity ranging from about 60 to 100Ω. Moreover, the dc resistivity of the secondary winding of the output transformer T is about 5Ω. Namely, the dc resistivity provided by the secondary winding of the output transformer T is much smaller than that provided by the source coil 14 or resistor R (about a one-tenth).

When the comparator is used, the comparator checks a fractional voltage of the voltage developed at the power terminal, which is produced due to the dc resistivity of the source coil serving as a load and the dc resistivity of the checking resistor R, to see if the fractional voltage ranges from about 1.2 V to about 1.6 V. This is attributable to the fact that when the shape-of-endoscope detecting system is normal (though it depends on mode), the fractional voltage ranges from about 1.2 V to about 1.6 V.

In contrast, for example, if one terminal of the source coil 14 is disconnected, the fact is learned from the voltage at the power terminal. If the terminals of the source coil 14 are short-circuited, a ground-level voltage is detected. In both the cases, it is judged from a voltage, which falls outside a normal range, that a failure has occurred.

Figure 31:
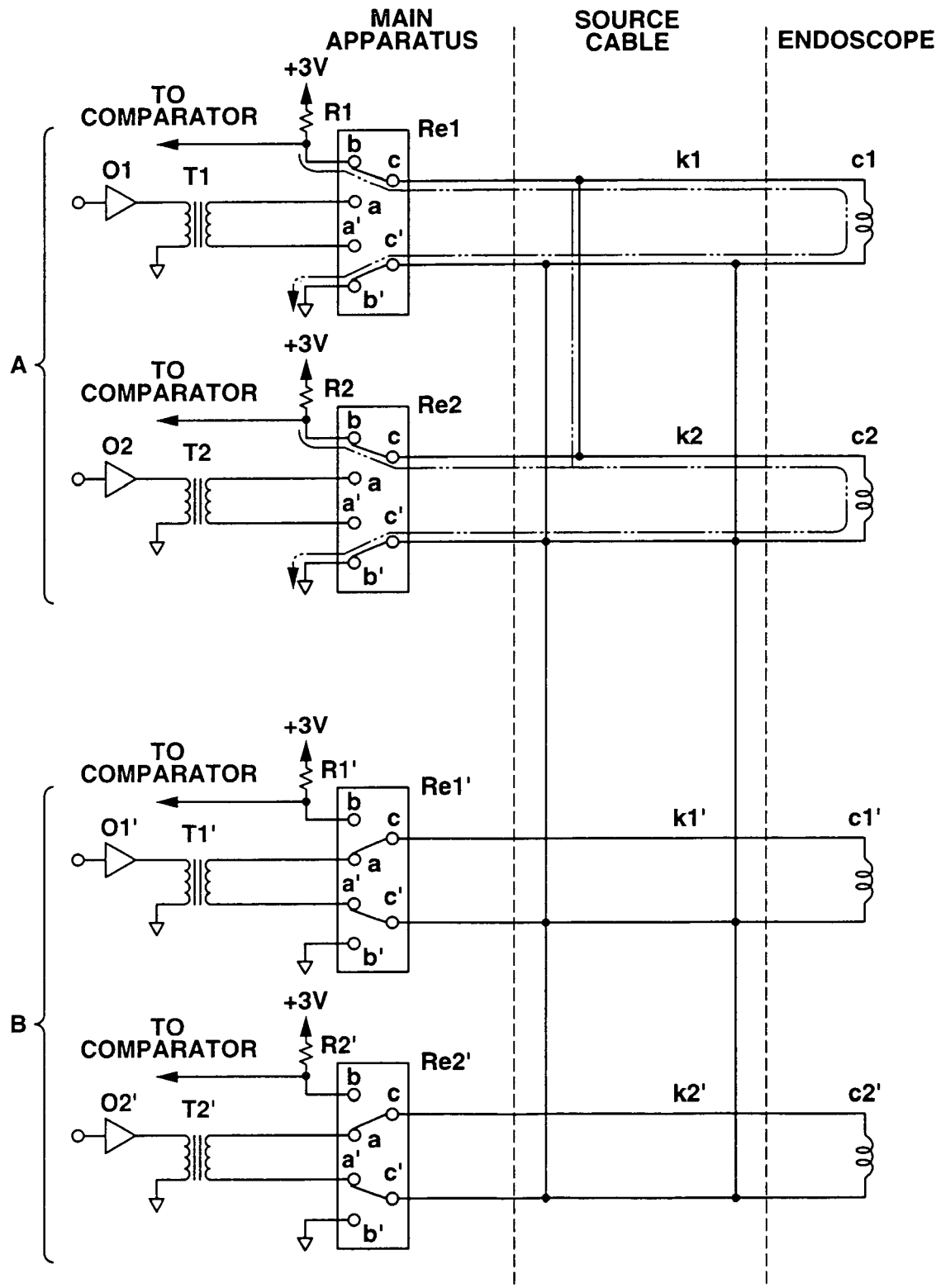
Figure 32:
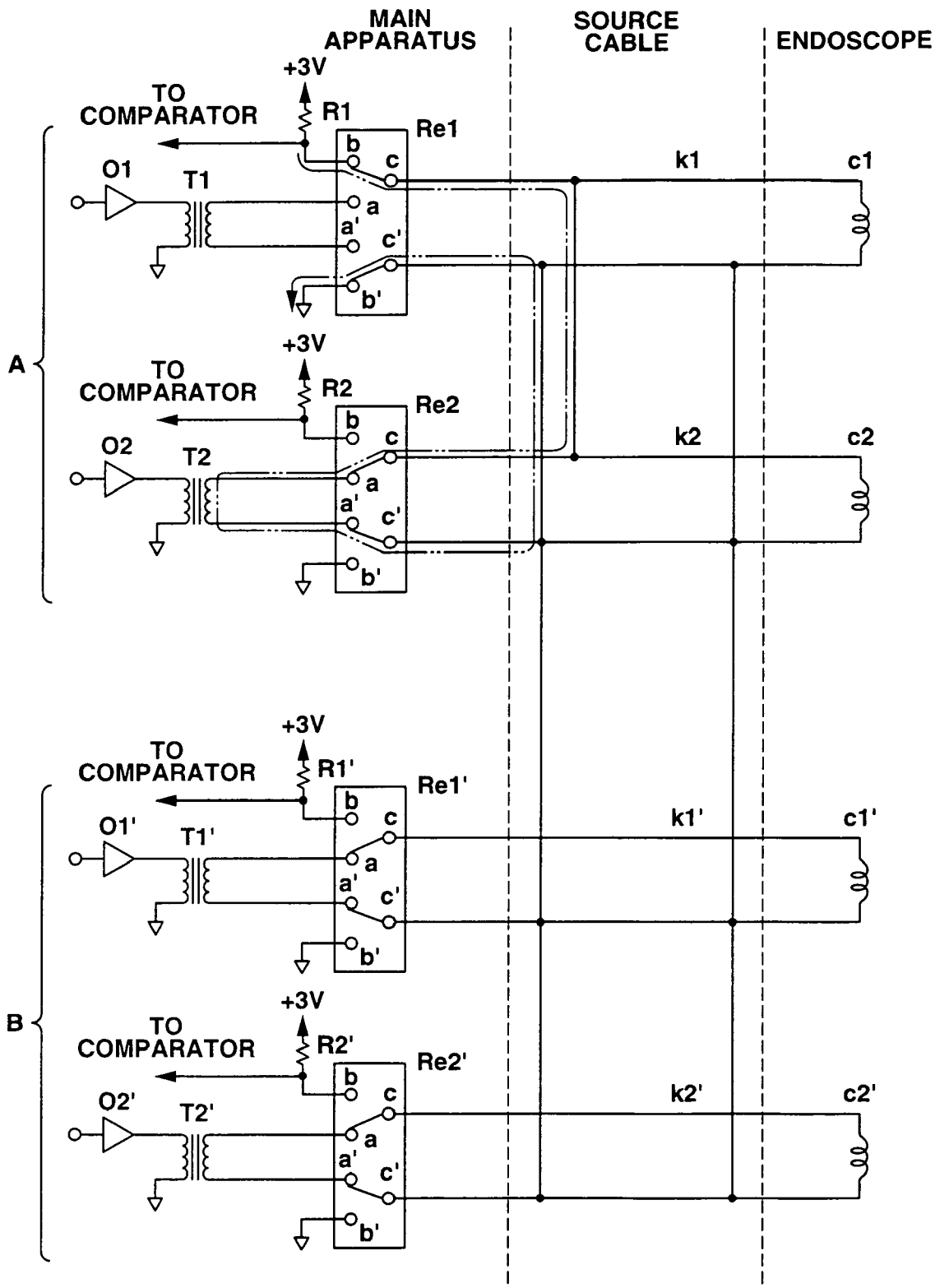

In reality, the number of drive circuits 61*i* corresponds to the number of source coils 14*i*, and the drive circuits drive or check the respective source coils 14*i* as shown in FIG. 31 and FIG. 32.

Moreover, according to the present embodiment (and before an improvement is made), since the number of source coils 14*i* is large, the source coils 14*i* are divided into a plurality of groups (hereinafter, groups A, B, and C). The groups of source coils are driven at different timings.

Figure 30A:
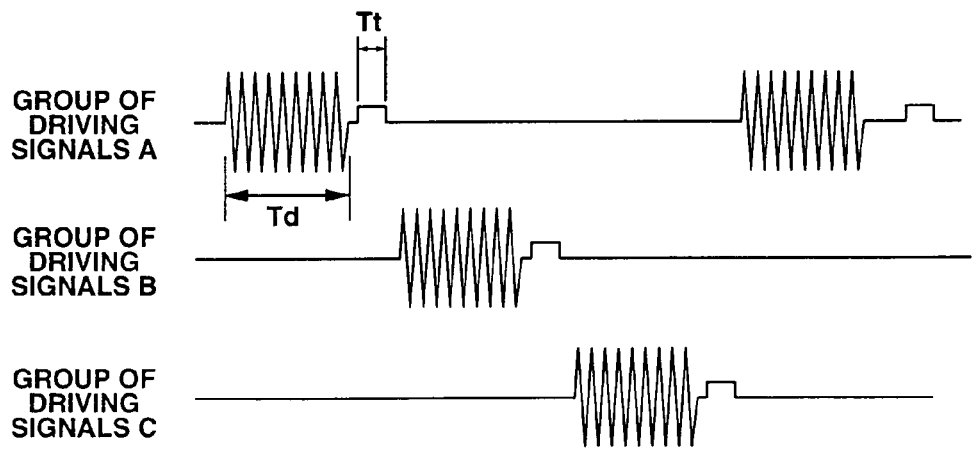
FIG. 30A shows an example of driving waves indicating different driving periods and checking periods during which different groups of source coils are driven or checked.

To be more specific, up to twenty-four source coils 14*i* can be driven, and eight source coils are driven at a time. Namely, as shown in FIG. 30A, driving periods Td during which a driving signal is applied to the group A, B, or C are varied (so that they will not coincide with one another). The source coils 14*i* belonging to the groups A, B, and C are driven during the respective driving periods Td.

Figure 30B:
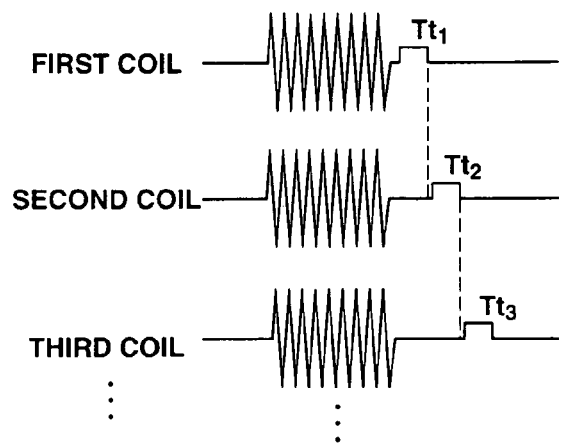
FIG. 30B indicates the different start time instants of checking periods during which source coils belonging to the same group are checked.

Moreover, the driving period Td is succeeded by a checking period Tt so that the source coils can be checked. In this case, before an improvement is made, as far as the same group of source coils is concerned, the driving periods Td and checking periods Tt during which the respective source coils are driven or checked come at the same timings. According to the present embodiment, as shown in FIG. 30B, as far as the same group of source coils, I, (where I equals A, B, or C) is concerned, the checking periods Tt1, Tt2, etc. during which the first, second, etc., and eighth respective source coils are checked are different from one another and do not coincide with one another.

FIG. 31 and FIG. 32 show the output stage of the drive circuit 61 included in the main apparatus, the source cable 16, and the source coils 14*i* disposed in the endoscope 6 in comparison with those employed before an improvement is made.

In FIG. 31 and FIG. 32, for brevity's sake, the source coils c1, c2, etc. belonging to the group A and the source coils c1', c2', etc. belonging to the group B are shown on behalf of the source coils 14*i*. Moreover, signal lines k1, k2, etc. and signal lines k1', k2', etc. that are contained in the source cable 16 shall be coupled to the source coils c1, c2, etc. and the source coils c1', c2', etc.

The operational amplifiers O1, O2, etc., output transformers T1, T2, etc., and relays Re1, Re2, etc. shall be connected to the source coils belonging to the group A. The operational amplifiers O1', O2', etc., output transformers T1', T2', etc., and relays Re1', Re2', etc. shall be connected to the source coils belonging to the group B.

Moreover, in FIG. 31 and FIG. 32, for brevity's sake, the number of groups of source coils is two of groups A and B. Moreover, the number of source coils belonging to each of the groups A and B is two. In reality, each group I includes eight source coils that can be driven.

Figure 35:
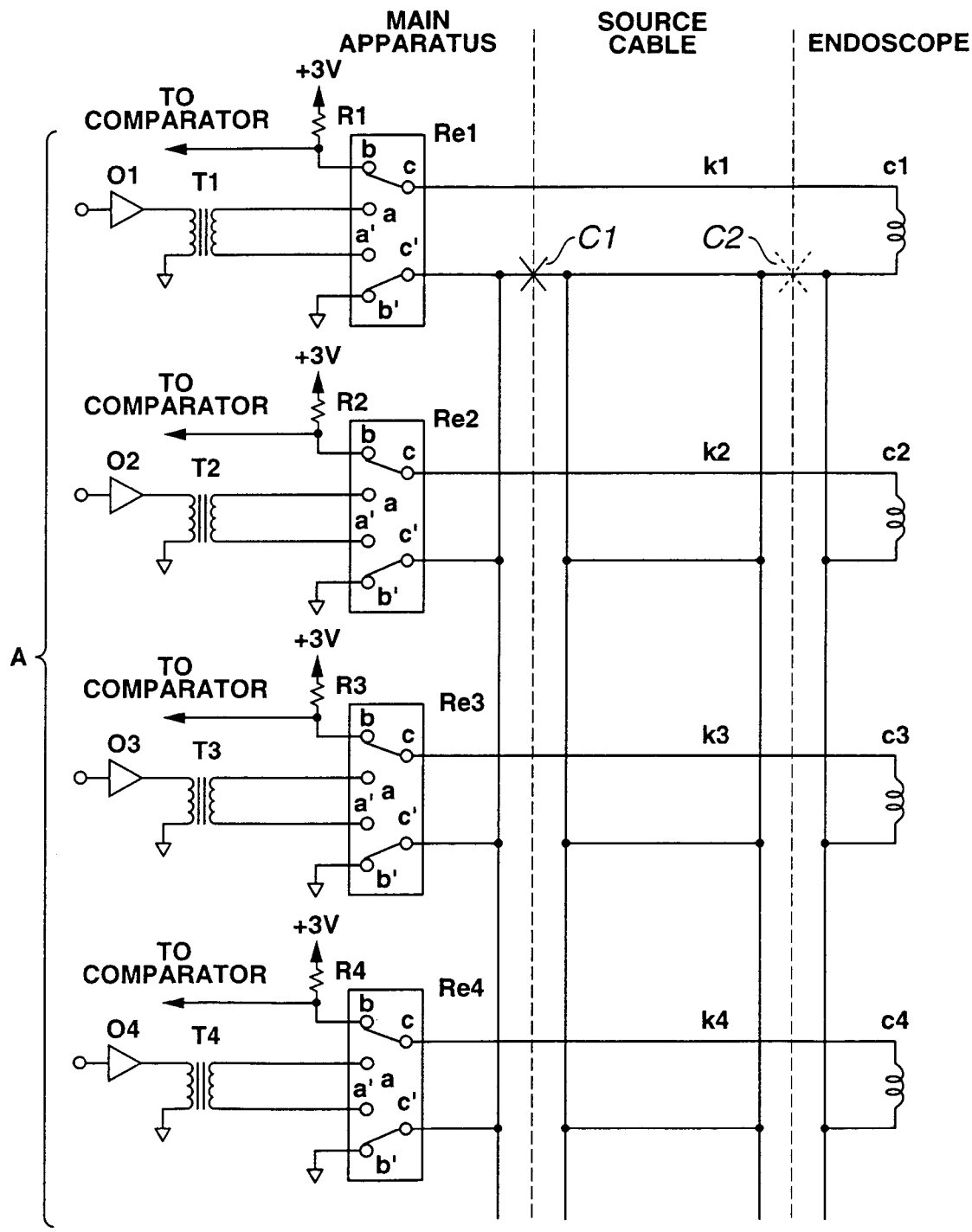

According to the present embodiment, as shown in FIG. 32, the return sides of all the signal lines k1, k2, etc. over which applied signals return are linked in common in front of the joint at which the source cable 16 is joined to the main apparatus, and are then spliced to the connector receptacle formed in the main apparatus. Moreover, the return sides of the signal lines are linked in common in front of the joint at which the source cable 16 is joined to the endoscope. (Strictly speaking, a structure shown in FIG. 35 is adopted. Namely, the signal lines k1, k2, etc., and k1', k2', etc. are formed with complex coaxial cables. The shielded sides (that is, return sides) of the signal lines coupled to the source coils belonging to each group are joined together at a point.)

Owing to the above structure, the number of contact pins included in a connector to be mated with a connector receptacle at each joint can be halved. Therefore, the connector is not large in size. The connector can be designed to be compact and lightweight so that it can be attached to the main apparatus easily.

FIG. 31 shows the same components as FIG. 32 employed before an improvement is made, wherein the return sides of the signal lines are linked in common (as those employed in the present embodiment) and the source coils belonging to the same group are checked at the same checking timing as they are in a related art.

As described in conjunction with FIG. 30A, before an improvement is made, the source coils belonging to the same group I are checked at the common checking timing Tt. Therefore, if any of the discrete sides of the signal lines coupled to the source coils belonging to the same group I, which are not linked in common, are short-circuited, the failure cannot be detected.

Before an improvement is made, for example, as shown in FIG. 31, if the discrete sides of the signal lines k1 and k2 coupled to the source coils c1 and c2 belonging to the group A are short-circuited, the resistors R1 and R2 (having the same resistance) are connected in parallel with each other. Moreover, the source coils c1 and c2 are connected in parallel with each other. Consequently a circuit through which a checking current flows is formed as indicated with an alternate long and two short dashes line.

In this case, a comparator detects a voltage as if to detect a voltage with only one source coil c1 included. Consequently, the failure cannot be detected.

In contrast, according to the present embodiment, as shown in FIG. 30B, the checking periods Tt during which the source coils belonging to the same group I are checked are different from one another and do not coincide with one anther. Thus, the source coils are checked as shown in FIG. 32.

During the period Tt1 during which the source coil c1 is checked, the contacts b and b' in the relay Re1 are conducting. However, in the relay Re2 used to check the source coil c2, the contacts a and a' are conducting. In other words, a closed circuit through which a checking current flows is formed as indicated with an alternate long and two short dashes line in FIG. 32.

As mentioned above, the dc resistivity of the secondary winding of the output transformer T2 (or T1) is much smaller than that given by the source coil c1 or resistor R1. In the case shown in FIG. 32, the resistor R 1 lies independently (is not connected in parallel with the resistor R2). Approximately, the state of the resistor R1 looks like a state in which a small resistance given by the secondary winding of the output transformer T2 is applied to one terminal of the resistor R1. (Strictly speaking, the state of the resistor R1 is equivalent to a state in which the source coils c1 and c2 are connected in parallel with the secondary winding of the output transformer T2.)

Namely, in this state, when a resistor whose resistance is almost zero is connected in series with one terminal of the resistor R1, a comparator detects the voltage at the one terminal of the resistor R1. A circuit through which a checking current flows is almost like the one indicated with an alternate long and two short dashes line.

In this case, the detected voltage is a nearly zero level and falls outside a normal range. Consequently, it is judged that a failure (a short circuit) has occurred.

When the discrete sides of the signal lines coupled to the source coils belonging to different groups are short-circuited, similarly to when the discrete sides of the signal lines coupled to the source coils belonging to the same group are short-circuited, it is recognized that a failure has occurred (even before an improvement is made).

Figure 33A:
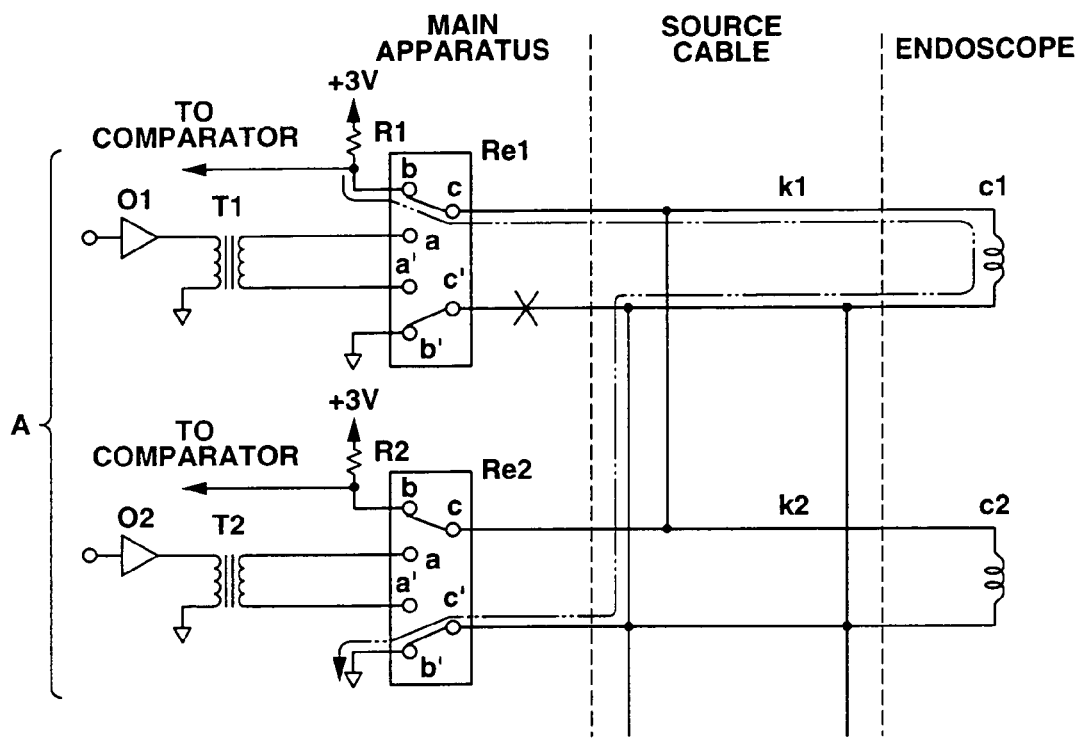
FIG. 33A and FIG. 33B are explanatory diagrams signifying an operation (of the present embodiment) to be exerted when a signal line in a main apparatus is disconnected in comparison with the one to be exerted before an improvement is made.

Before an improvement is made, when any of the common sides of the signal lines coupled to the source coils belonging to the same group shown in FIG. 31 is disconnected (the discrete sides are not short-circuited), the state shown in FIG. 33A ensues. In FIG. 33A, the disconnected position is indicated with a cross.

Even in this case, a checking current circuit is formed as indicated with an alternate long and two short dashes line. Namely, although a disconnection has occurred, an equivalent circuit devoid of a disconnection is formed. Therefore, the disconnection cannot be detected.

Figure 33B:
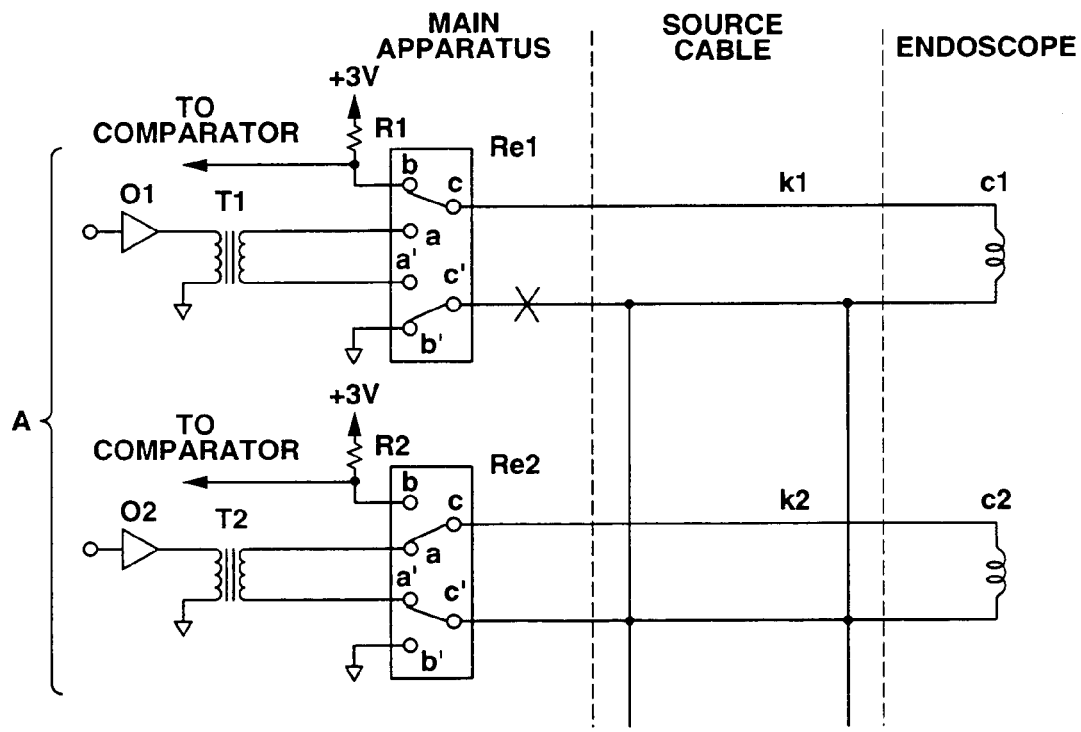

In contrast, according to the present embodiment, the checking period during which the states of the relay Re1 are switched is different from the checking period during which the states of the relay Re2 are switched. The states of the contacts included in the relay Re1 and relay Re2 become as shown in FIG. 33B. In this case, when the contacts b and b' in the relay Re1 are conducting, the contacts a and a' in the relay Re2 are conducting. Consequently, a circuit through which a current flows to a ground is not formed (that is, a closed circuit is not formed). A comparator therefore detects the voltage at the power terminal and judges that a failure (a disconnection) has occurred.

Figure 34:
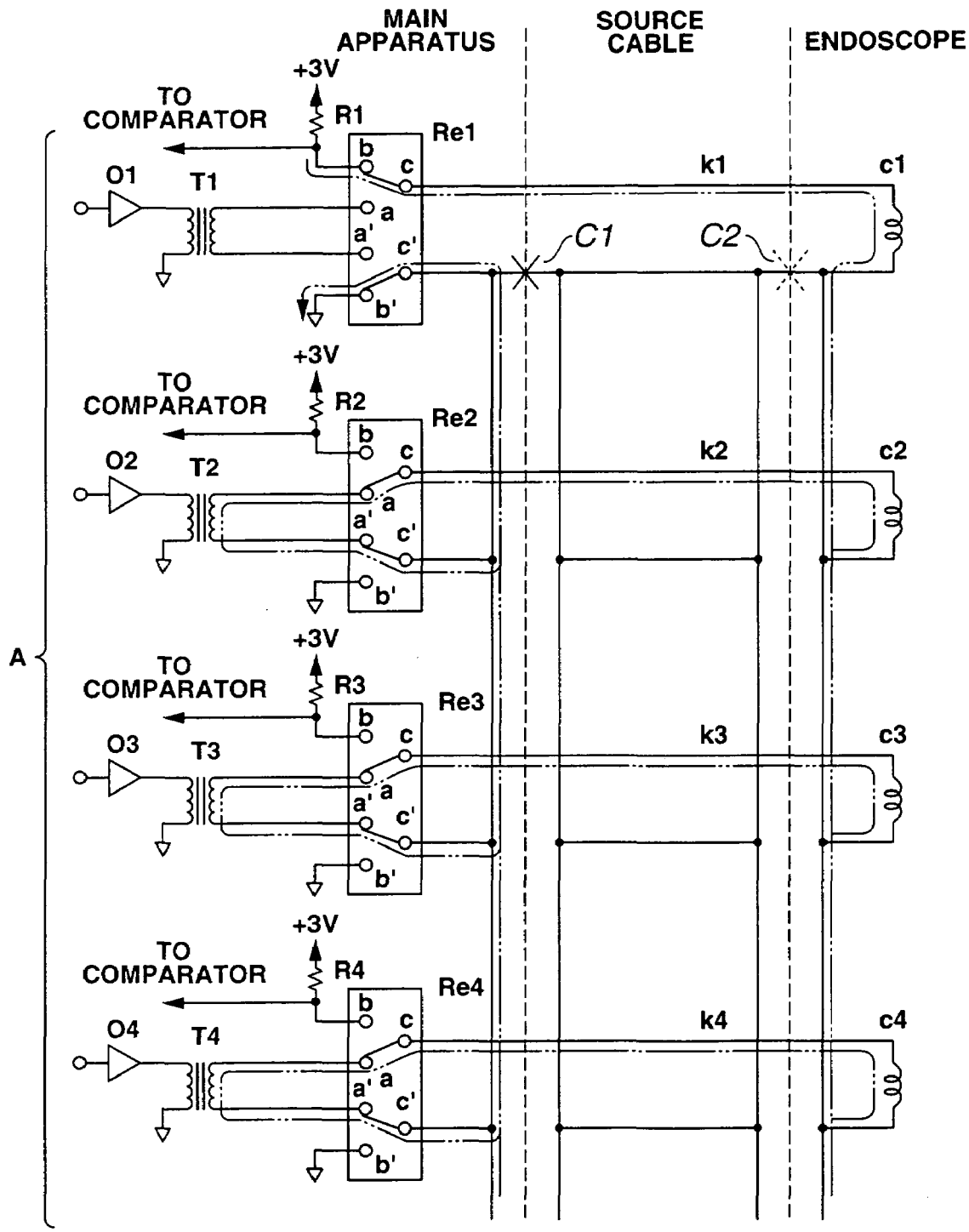

As shown in FIG. 34, the joint C1 at which the main apparatus and source cable are joined or the joint C2 at which the source cable 16 and a source coil are joined may be disconnected or may be imperfectly brought into contact with each other. Both the cases are detected basically in the same manner. A description will therefore be made on the assumption that the joint C1 is disconnected.

In this case, when the checking periods Tt are determined to be different from one another as shown in FIG. 30B, a circuit is formed as indicated with an alternate long and two short dashes line. Namely, the formed circuit includes: a path along which a current flows from the resistor R1 through the source coil c1 and then flows to a ground through the source coil c2 and output transformer T2; and a path along which a current branches out at the position of the source coil c2 and flows into a ground through the source coil c3 and the secondary winding of the output transformer T3.

Consequently, the above circuitry is approximately equivalent to the circuitry in which the seven source coils c2 to c7 that are connected in parallel with one another are connected in series with the source coil c1. A resistance given by the seven source coils c2 to c7 connected in parallel with one another is so small that the shape-of-endoscope detecting system may be judged to be normal.

The present embodiment provides (not only the mode in which the source coils are checked during the checking periods whose timings are different from one another but also) the mode in which all the checking periods are set to the same checking period and the source coils are checked during the checking period. For example, first, twenty-four source coils are checked during the checking period indicated in FIG. 30B. Thereafter, the source coils belong to the different groups are also checked during the same checking period.

FIG. 35 shows the connected state attained during the checking period. A closed circuit through which a checking current flows is not formed. Consequently, the voltage same as the power terminal is detected, and a failure is detected.

As mentioned above, each group of source coils is checked once. In other words, the three groups of source coils are each checked once.

According to the present embodiment, before the source coils disposed in the insertion portion 7 of the endoscope 6 are driven for actual use, an ambient noise is measured relative to a plurality of groups of driving signals having different frequencies that is used for driving. Based on the results of the measurement, a group of driving signals having different frequencies that causes the lowest ambient noise is adopted for driving the source coils. Consequently, the positions of the source coils can therefore be detected highly precisely while being little affected by an ambient noise, and a scope model can be displayed.

In the above description, the source coils that generate magnetic fields are disposed in the insertion portion 7, and the sense coils that detect magnetic fields are incorporated in the external coil unit 23. Alternatively, the places in which source coils and sense coils are located may be switched. Specifically, the sense coils may be incorporated in the insertion portion 7, and the source coils may be incorporated in the coil unit 23.

In the above description, the probe in which the source coils are incorporated is inserted in a forceps channel running through an endoscope, whereby the source coils are disposed in the endoscope insertion portion. Alternatively, the source coils may be directly incorporated in the endoscope insertion portion.

As described above, according to the present embodiment, there is provided a shape-of-endoscope detecting system that has one of pluralities of magnetic-field generating elements and magnetic-field detecting elements disposed in an endoscope insertion portion that is inserted into a subject. The other of the pluralities of magnetic-field generating elements and magnetic-field detecting elements is disposed outside the subject. The positions of one of the pluralities of elements disposed in the endoscope insertion portion are detected using the positions of the other of the pluralities of elements as a reference by means of a detecting means. The shape of the endoscope insertion portion is thus inferred and displayed on a display means. The shape-of-endoscope detecting system comprises:

a noise detecting means that can select ac driving signals having different frequencies and being used to drive the plurality of magnetic-field generating elements, and that detects a frequency component of a noise in a driving pause state in which the plurality of magnetic-field generating elements is not driven; and a driving control means that drives the plurality of magnetic-field generating elements using the ac driving signals that have different frequencies and that little contain the frequency component of a noise detected by the noise detecting means.

Consequently, the plurality of magnetic-field generating elements can be driven using the driving signals that have different frequencies and that are little affected by a noise. Eventually, the shape of the inserted insertion portion can be detected with a high signal-to-noise ratio.

Third Embodiment

Next, a third embodiment of the present invention will be described with reference to FIG. 36 to FIG. 39. An object of the present embodiment is to provide a shape-of-endoscope detecting system that can detect the positions of coils irrespective of the number of coils capable of being driven, and can calculate the shape of an endoscope insertion portion.

To be more specific, when source coils (or simply, coils) that generate magnetic fields are driven in a shape-of-endoscope detecting system in accordance with a related art, all the coils are driven simultaneously using a continuous wave whose frequency is slightly varied for each coil. In this case, the different frequencies are assigned to the respective coils. With an increase in the number of coils, the number of frequency channels to be assigned to the coils increases.

An actually usable frequency band is limited. If the number of channels is too large, the frequency band of each channel becomes narrow. Consequently, when the frequency components of a received signal are separated from one another, a frequency separation facility that separates the frequency components works ineffectively. This leads to the degraded precision in position detection. Therefore, the number of coils capable of being driven is restricted.

According to the present embodiment to be described below, the shape of an endoscope insertion portion can be calculated irrespective of the number of coils capable of being driven.

Figure 36:
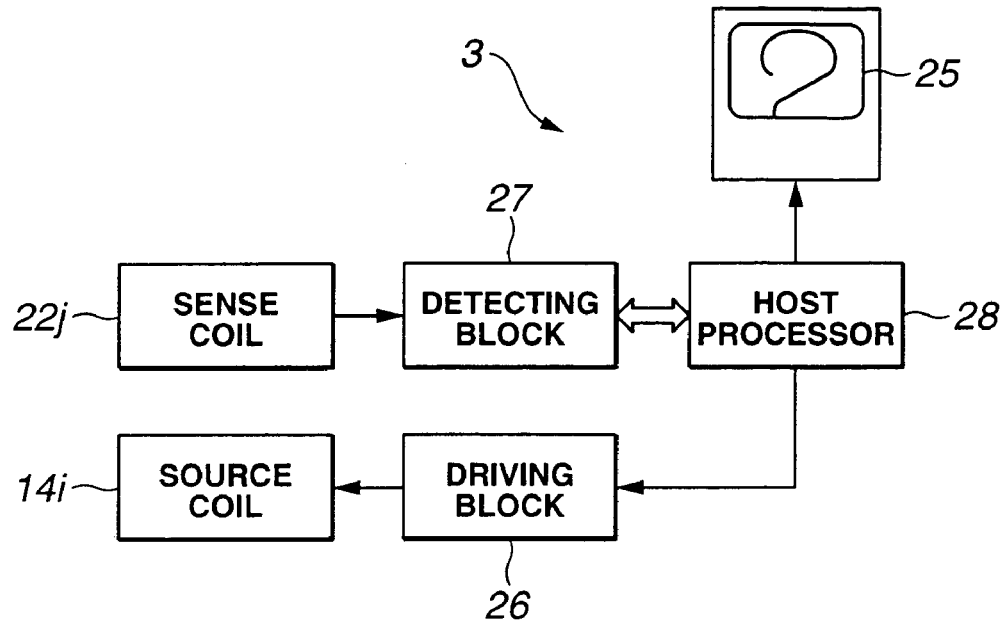
FIG. 36 to FIG. 39 are concerned with a third embodiment of the present invention.

An endoscopic system 1 including the present embodiment has the same configuration as the one shown in FIG. 1. A shape-of-endoscope detecting system 3 in accordance with the present embodiment comprises: as shown in FIG. 36, a driving block 26 that drives source coils 14$i$; a detecting block 27 that detects signals received by sense coils 22$j$ incorporated in a coil unit 23; and a host processor 28 that processes signals detected by the detecting block 27.

As shown in FIG. 4A, a probe 15 disposed in an insertion portion 7 of an electronic endoscope 6 has a plurality of source coils 14$i$, which generates magnetic fields, arranged at predetermined intervals. The source coils 14$i$ are connected to a source coil drive circuit (or simply a coil drive circuit) 31 included in the driving block 26.

The coil drive circuit 31 intermittently drives ten source coils, which belong to each of three groups into which the source coils 14$i$ are divided, using driving signals of sine waves having different frequencies. The frequencies of the driving signals are determined based on frequency determination data transferred to an oscillating frequency determination unit that determines frequencies at which oscillators included in the coil drive circuit 31 should oscillate. The frequency determination data is transferred from a central processing unit (CPU) 32, which calculates the shape of an endoscope and is included in the host processor 28, to the coil drive circuit 31 via a parallel input/output (PIO) circuit 33, whereby the frequencies of the driving signals are determined.

On the other hand, twelve sense coils 22$j$ incorporated in the coil unit 23 are connected to a sense coil signal amplification circuit 34 included in the detecting block 27. The sense coil signal amplification circuit 34 has the same configuration as the one shown in FIG. 5.

Figure 37:
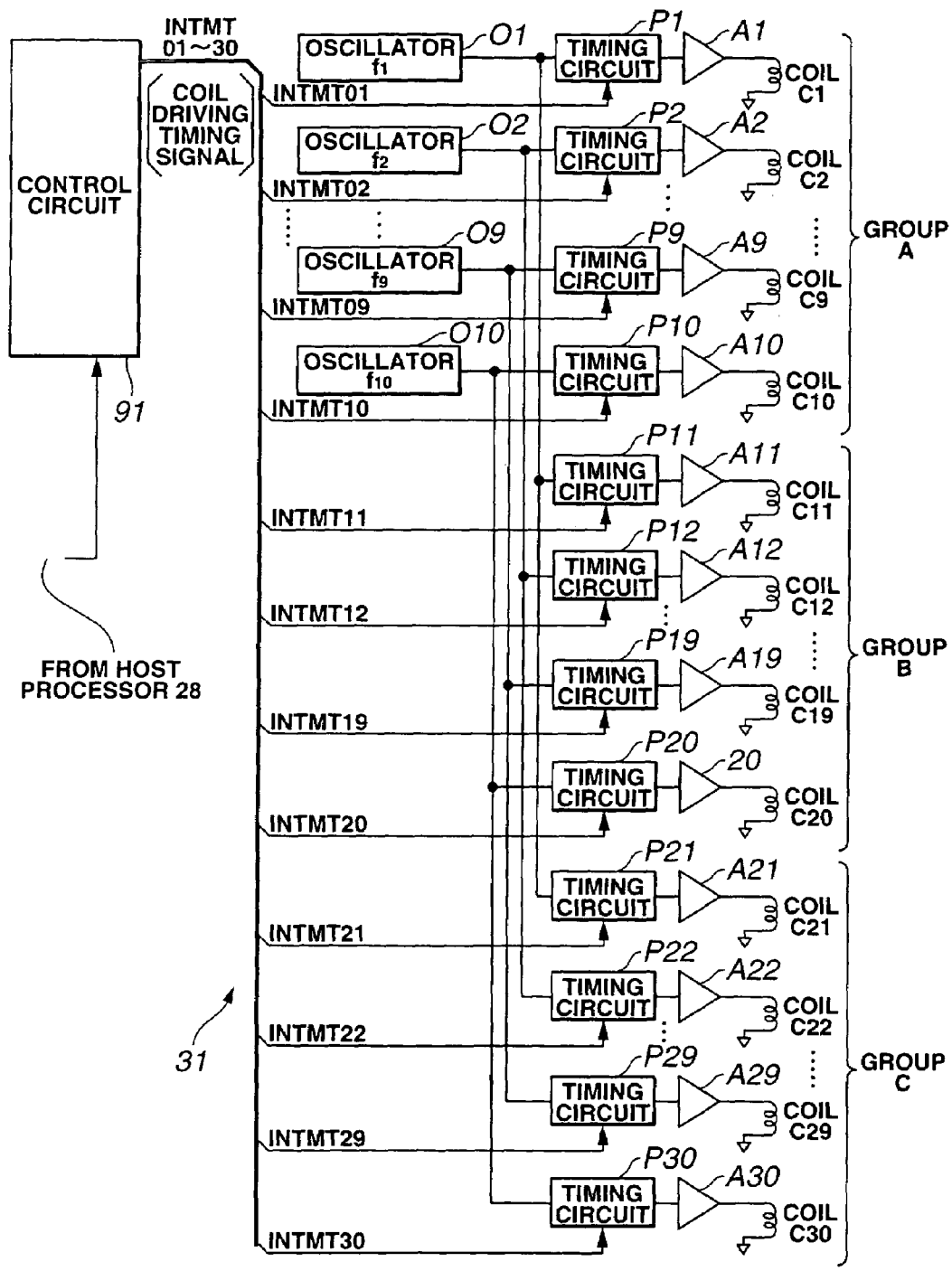

Referring to FIG. 37, the configuration of the coil drive circuit 31 employed in the present embodiment will be described below. Incidentally, for brevity's sake, the source coils are referred to, simply, as coils. For a better understanding, the i-th coil is referred to as a coil ci.

According to the present embodiment, for example, thirty coils C1 to C30 are divided into three groups A, B, and C including coils C1 to C10, coils C11 to C20, and coils C21 to C30 respectively. The ten coils belonging to each of the groups A, B, and C are driven simultaneously, and the coils belonging to the different groups are driven intermittently.

In this case, all the thirty coils C1 to C30 may be disposed in the insertion portion 7, or the thirty coils C1 to C30 may include coils disposed in the insertion portion 7 and coils employed in auxiliaries such as an external marker 57 and reference plate 58.

When the coils C1 to C10 belonging to the group A are driven, the driving of the groups B and C of coils C11 to C20 and coils C21 to C30 respectively is suspended.

Moreover, when the coils C11 to C20 belonging to the group B are driven, the driving of the groups A and C of coils C1 to C10 and coils C21 to C30 respectively is suspended.

Moreover, when the coils C21 to C30 belonging to the group C are driven, the driving of the groups A and B of coils C11 to C20 and coils C11 to C20 respectively is suspended.

The host processor 28 transmits a control signal to a control circuit 91 so that the driving will be controlled as mentioned above. The control circuit 91 controls the timing of switching timing circuits (switching circuits) P1 to P30 included in the coil drive circuit 31 according to timing signals INITMT01 to INITMT30, and produces driving waves as described below.

Specifically, ten oscillators O1 to O10 control switching of the states of the timing circuits P1 to P10, P11 to P20, and P21 to P30 respectively in response to the coil driving timing signals INTMT01 to INTMT30 sent from the control circuit 51. Herein, the timing circuits P1 to P10, P11 to P20, and P21 to P30 respectively are connected to the input terminals of amplifiers A1 to A10, A11 to A20, and A21 to A30 respectively whose output terminals are connected to the groups A, B, and C of coils C1 to C 10, coils C11 to C20, and coils C21 to 30 respectively.

To be more specific, for example, an oscillating signal produced by the oscillator O1 is transferred to the timing circuits P1, P11, and P21 that serve as selector switches to be used to drive the coils C1, C11, and C21 belonging to the groups A, B, and C respectively. In response to the coil driving timing signals INTMT01, INTMT11, and INTMT21 sent from the control circuit 51, the states of each of the timing circuits P1, P11, and P21 are switched from a non-conducting state to a conducting state.

Moreover, an oscillating signal produced by the oscillator O2 is transferred to each of the timing circuits P2, P12, and P22 that serve as selector switches to be used to drive the coils C2, C12, and C22 belonging to the groups A, B, and C respectively. In response to the coil driving timing signals INTMT02, INTMT12, and INTMT22 sent from the control circuit 91, the states of each of the timing-circuits P2, P12, and P22 are switched from the non-conducting state to the conducting state.

Likewise, oscillating signals produced by the oscillators O3, etc., and O10 are transferred to the timing circuits P3, P13, P23, etc., P10, P20, and P30 respectively.

In this case, in order to intermittently drive the coils C1 to C10, coils C11 to C20, and coils C21 to C30 belonging to the groups A, B, and C respectively, the control circuit 91 sequentially and intermittently transmits the coil driving timing signals INTMT01 to INTMT10, coil driving timing signals INTMT11 to INTMT20, and coil driving timing signals INTMT21 to INTMT30 to the timing circuits P1 to P10, timing circuits P11 to P20, and timing circuits P21 to P30 respectively so that the groups of coil driving timing signals will not temporally coincide with one another.

Figure 38:
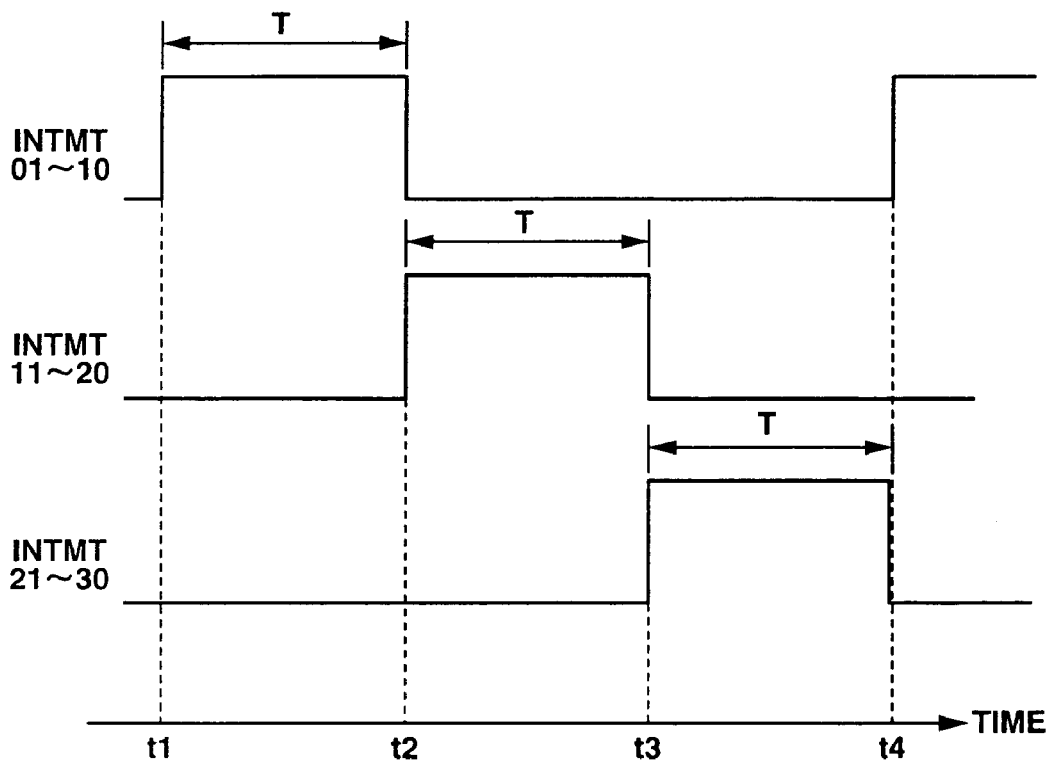

Specifically, as shown in FIG. 38, the control circuit 91 transmits the (binary-coded) coil driving timing signals INTMT01 to INTMT10 (during a period of time T starting at a time instant t1). During the period of time T starting at an immediately succeeding time instant t2, the control circuit 91 transmits the coil driving timing signals INTMT11 to INTMT20. During the period of time T starting at an immediately succeeding time instant t3, the control circuit 91 transmits the coil driving timing signals INTMT21 to INTMT30. At an immediately succeeding time instant t4, similarly to the time instant t1, the control circuit 91 starts transmitting the coil driving timing signals INTMT01 to INTMT10.

In this case, for example, immediately after the coil driving timing signals INTMT01 to INTMT10 are transmitted for the period of time T starting at the time instant t1, transmitting the next coil driving timing signals INTMT11 to INTMT20 is started at the time instant t2. In reality, the next coil driving timing signals INTMT11 to INTMT20 are transmitted at the timing that the amplitudes of the signals applied to the preceding coils C1 to C10 become small enough.

For example, when the coil driving timing signals INTMT01 to INTMT10 are transmitted, the states of each of the timing circuits P1 to P10 are switched from the non-conducting state to the conducting state. The oscillating signals produced by the oscillators O1 to O10 pass through the timing circuits P1 to P10 respectively, and are amplified by the amplifiers A1 to A10 in the stage succeeding the timing circuits. The resultant driving signals are applied to the coils C1 to C10, whereby magnetic fields are induced about the coils C1 to C10. The sense coils 22j incorporated in the coil unit 23 detect the magnetic fields.

Likewise, when the coil driving timing signals INTMT11 to INTMT20 are transmitted, the coils C11 to C20 are driven. When the coil driving timing signals INTMT21 to INTMT30 are transmitted, the coils C21 to C30 are driven.

Figure 39:
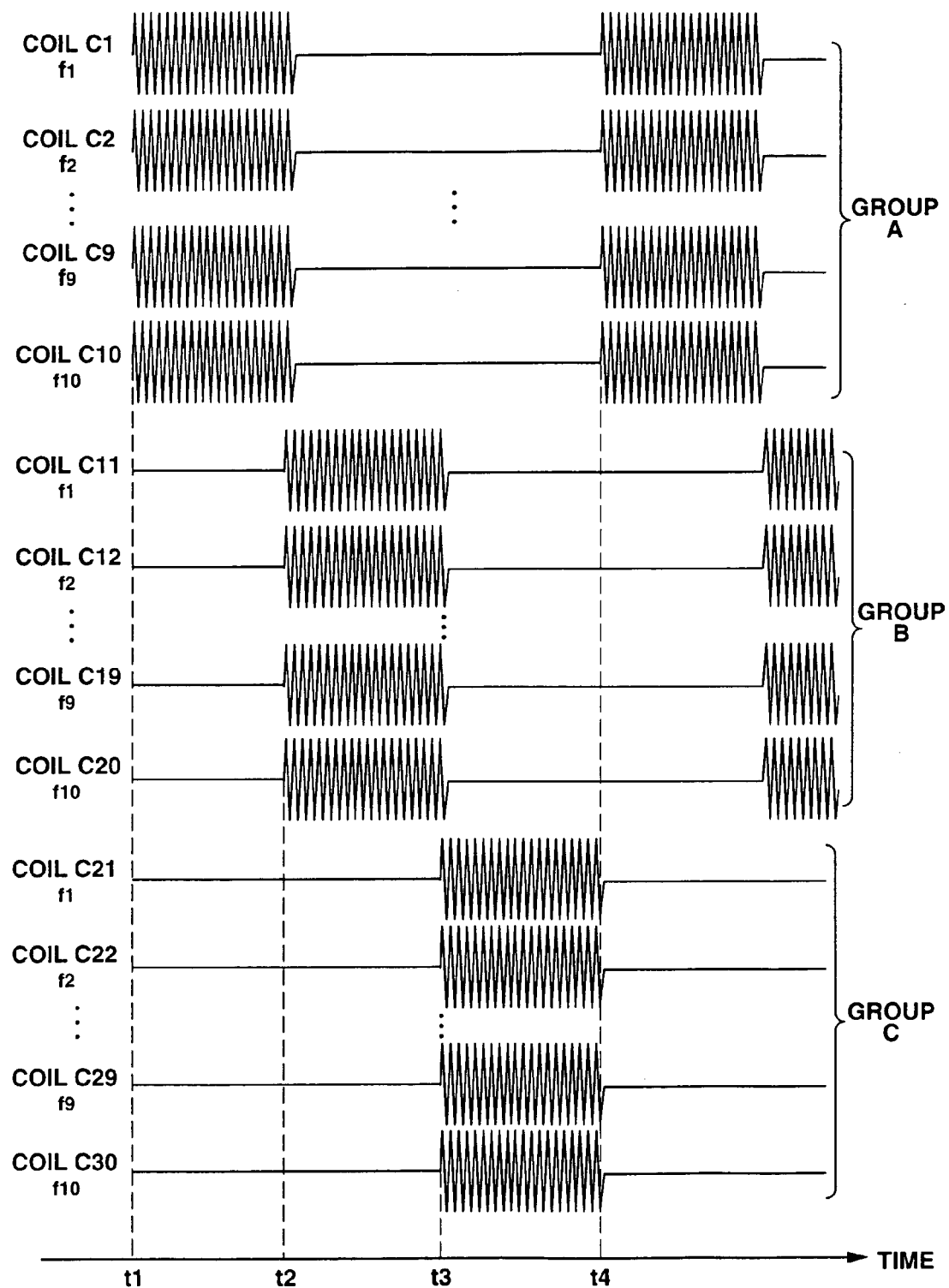

Consequently, the coils C1 to C10, coils C11 to C20, and coils C21 to C30 belonging to the groups A, B, and C respectively are intermittently driven as shown in FIG. 39.

As mentioned above, the coils C1 to C30 are divided in tens into the groups A, B, and C. Therefore, the timings of driving the respective coils belonging to the same group do not coincide with one another. The same frequency can therefore be assigned to the coils C1, C11, and C21. Compared with the related art, according to the present embodiment, a triple number of coils can be driven using the same number of channels.

The host processor 28 controls the detecting block 27 connected to the sense coils 22j synchronously with the timing of driving the source coils under the control of the control circuit 91. When the groups A, B, and C are intermittently driven, the detecting block 27 detects the positions of the coils C1 to C10, coils C11 to C20, and coils C21 to C30 respectively using the sense coils 22j.

Namely, the coils C1 to C10, coils C11 to C20, and coils C21 to C30 belonging to the groups A, B, and C are driven sequentially and cyclically. However, since the driving timings are different from one another, the host processor 28 recognizes which of the coils is associated with a signal detected by the detecting block 27. The position data of each coil can therefore be accurately calculated.

According to the present embodiment, coils to be driven are divided into a plurality of groups, and intermittently driven so that the driving periods will not coincide with one another. The number of coils capable of being driven can be increased using a small number of frequency channels.

Consequently, the number of coils being disposed in the insertion portion 7 can be increased and the coils can be arranged at intervals of a small distance. Therefore, even when the insertion portion 7 is bent, the position of the bent of the insertion portion 7 can be detected highly precisely by detecting the positions of the coils. In other words, the shape of the insertion portion 7 can be detected highly precisely.

Moreover, compared with the coils continuously driven, since the coils are intermittently driven, the current value of a driving signal flowing into each coil can be increased. Consequently, the precision in detecting the positions of the coils improves. Moreover, an effective range of detection within which the positions of the coils can be detected with practical precision can be expanded.

Moreover, when the effective range of detection need not be expanded, energy to be consumed by each coil can be minimized, and a rise in temperature due to energy consumption by coils can be suppressed.

Moreover, the number of oscillators may be a quotient calculated by dividing a conventionally needed number of oscillators by the number of groups of source coils (in the above case, a one-third of the number of oscillators). This leads to a reduction in the scale of a circuit. Eventually, a shape-of-endoscope detecting system can be designed compactly at a low cost.

Fourth Embodiment

Figure 40:
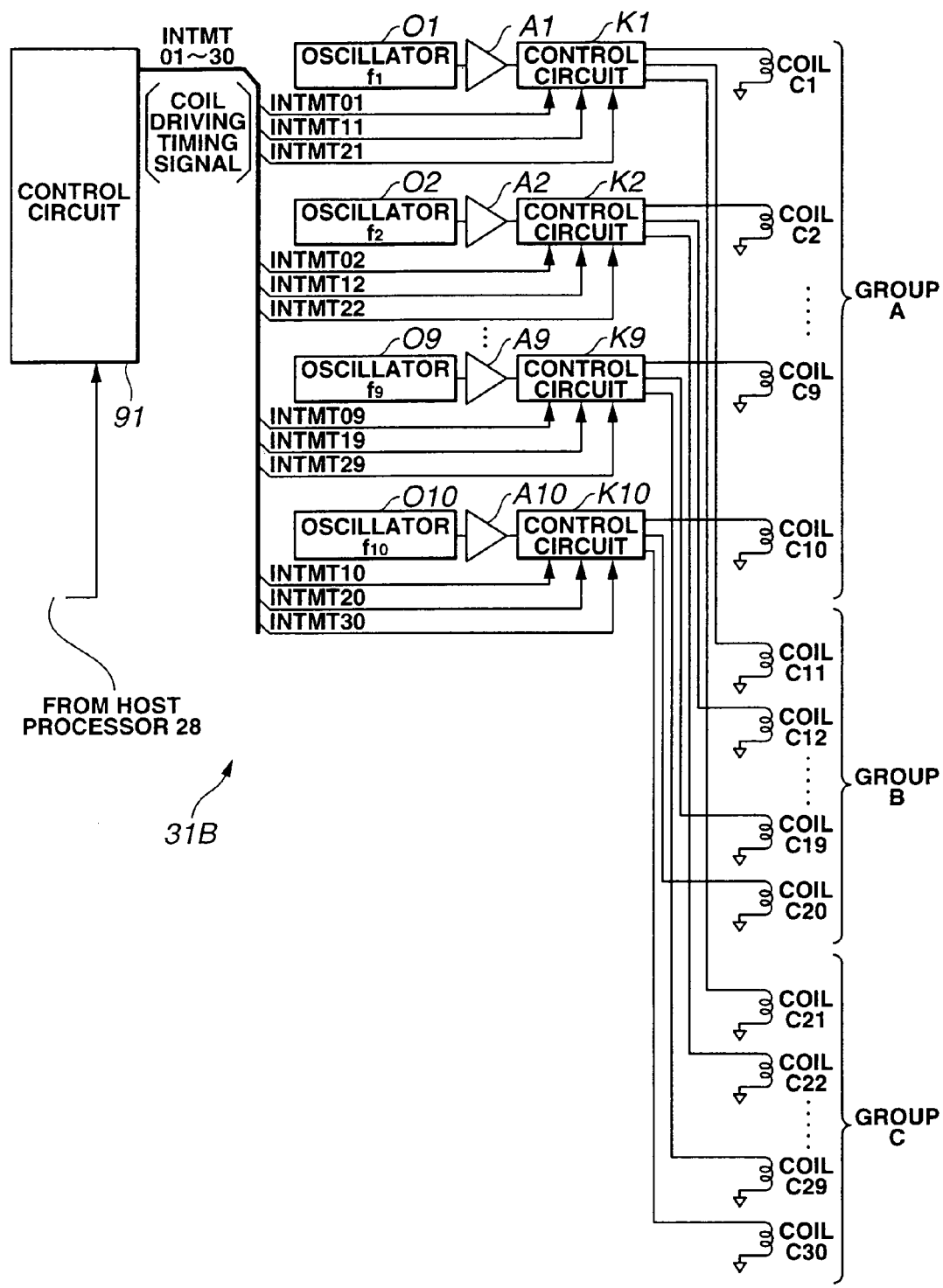
FIG. 40 is a circuit diagram showing the configuration of a coil drive circuit employed in a fourth embodiment of the present invention.

Next, a fourth embodiment of the present invention will be described with reference to FIG. 40. The present embodiment is different from the third embodiment in the configuration of the coil drive circuit 31. FIG. 40 shows a coil drive circuit 31B employed in the present embodiment.

As shown in FIG. 40, oscillating signals produced by oscillators O1 to O10 are amplified by amplifiers A1 to A10. The resultant driving signals are transmitted to coils C1 to C30 via switching circuits K1 to K10.

Coil driving timing signals INTMT01 to INTMT10, INTMT11 to INTMT20, and INTMT21 to INTMT30 sent from a control circuit 91 are applied to the switching circuits K1 to K30. In this case, the control circuit 91 transmits the coil driving timing signals INTMT01 to INTMT10, INTMT11 to INTMT20, and INTMT21 to INTMT30 according to the timings shown in FIG. 38 concerning the first embodiment.

For example, the control circuit 91 transmits the binary-coded coil driving timing signals INTMT01 to INTMT10 during a period of time T starting at a time instant t1. In this case, in response to the coil driving timing signal INTMT01, a driving signal sent from the amplifier A1 is applied to the coil C1 via the switching circuit K1. Moreover, in response to the coil driving timing signal INTMT02, a driving signal sent from the amplifier A2 is applied to the coil C2 via the switching circuit K2. Likewise, in response to the coil driving timing signal INTMT10, a driving signal sent from the amplifier A10 is applied to the coil C10 via the switching circuit K10. Namely, the coils C1 to C10 belonging to group A are simultaneously driven at different frequencies.

Likewise, when the coil driving timing signals INTMT11 to INTMT20 are transmitted, the coils C11 to C20 belonging to group B are simultaneously driven at different frequencies. When the coil driving timing signals INTMT21 to INTMT30 are transmitted, the coils C21 to C30 belonging to group C are simultaneously driven at different frequencies.

In short, the coils C1 to C30 are driven in the same manner as those included in the first embodiment.

The present embodiment provides almost the same advantages as the third embodiment. In addition, since the amplifiers A1 to A10 are located in a stage preceding the switching circuits K1 to K10, the number of amplifiers can be decreased. Consequently, the scale of a circuit can be reduced.

In the aforesaid embodiments, for example, thirty coils C1 to C30 are divided into three groups. The number of groups into which the coils are divided may be increased in order to decrease the number of frequencies employed. For example, the number of groups into which the coils are divided may be identical to the number of coils. In this case, the coils can be intermittently driven using a sole driving signal of a sole frequency.

Moreover, in the first and second embodiments, the probe 15 is inserted through a forceps port of the electronic endoscope 6 in order to thus dispose the source coils in the insertion portion 7 of the electronic endoscope 6. Alternatively, the source coils may be incorporated in advance as integral parts of the insertion portion 7 of the electronic endoscope 6. Moreover, the present invention is not limited to the electronic endoscope. A fiber-optic endoscope will do.

As described above, according to the third and fourth embodiments, there is provided a shape-of-endoscope detecting system that has a plurality of coils disposed in an endoscope insertion portion, applies driving signals to the respective coils, and detects generated magnetic fields to detect the positions of the coils, and thus detects the shape of the endoscope insertion portion.

The shape-of-endoscope detecting system includes an intermittently driving means for dividing a plurality of coils into a plurality of groups, and for intermittently driving the coils belonging to each group so that the driving timings will not coincide with one another. Consequently, the shape of the endoscope insertion portion can be detected irrespective of the number of coils.

INDUSTRIAL APPLICABILITY

As described above, as far as a shape-of-endoscope detecting system in accordance with the present invention is concerned, even when an endoscope insertion portion inserted into a subject is bent, the shape of the insertion portion can be detected more highly precisely using position information of virtually disposed elements in addition to position information of a plurality of elements that is disposed in the longitudinal direction of the endoscope insertion portion and that generates magnetic fields. The shape-of-endoscope detecting system will assist in smoothly proceed with inserting work.

The invention claimed is:

1. A shape-of-endoscope detecting system for inferring a shape of an endoscope insertion portion adapted for insertion into a subject, wherein one of a plurality of magnetic-field generating elements and a plurality of magnetic-field detecting elements is disposed in the endoscope insertion portion, and the other of the plurality of magnetic field generating elements and the plurality of magnetic field detecting elements is disposed outside the subject, the shape-of-endoscope detecting system comprising:
   a detecting means for detecting positions of the one of the plurality of magnetic-field generating elements and the plurality of magnetic-field detecting elements, disposed in the endoscope insertion portion, using positions of the other of the plurality of magnetic-field generating elements and the plurality of magnetic-field detecting elements, disposed outside the subject; and
   a data interpolating means
      for, positioning one or more virtual elements among the plurality of magnetic-field generating elements or the plurality of magnetic-field detecting elements whose positions are detected, based on the detected positions detected by the detecting means and
      for interpolating data, which represents one or more intermediate positions between the detected positions of adjoining elements of the plurality of magnetic-field generating elements or magnetic-field detecting elements whose positions are detected, using the positions of the one or more virtual elements.

2. A shape-of-endoscope detecting system according to claim 1, wherein the plurality of elements disposed in the endoscope insertion portion is the plurality of magnetic-field generating elements.

3. A shape-of-endoscope detecting system according to claim 1, further comprising an estimating means for estimating the positions of the one or more virtual elements using a distance information representing a distance between the detected positions of adjoining elements of the plurality of magnetic-field generating elements or the plurality of magnetic-field detecting elements whose positions are detected.

4. A shape-of-endoscope detecting system according to claim 1, wherein the data interpolating means positions the one or more virtual elements among the plurality of magnetic-field generating elements or the plurality of magnetic-field detecting elements whose positions are detected so as to meet a predetermined condition including disposing the one or more virtual elements with a radius of curvature larger than a minimal radius when the endoscope insertion portion is looped.

5. A shape-of-endoscope detecting system according to claim 1, wherein the data interpolation is executed by software.

6. A shape-of-endoscope detecting system according to claim 1, wherein the data interpolating means verifies whether a length of an arc calculated to link the positions of adjoining elements disposed in the endoscope insertion portion, falls within a range from an upper limit and a lower limit with the interval between the adjoining elements as a reference.

7. A shape-of-endoscope detecting system according to claim 6, wherein if the length of the arc is smaller than the lower limit, the data interpolating means disposes the virtual elements at positions off the arc.

8. A shape-of-endoscope detecting system according to claim 1, further comprising:
   a noise detecting means for selecting ac driving signals that have different frequencies and that are used to drive the plurality of magnetic-field generating elements, and for detecting a frequency component of a noise in a driving pause state in which the plurality of magnetic-field generating elements is not driven; and
   a driving control means for driving the plurality of magnetic-field generating elements using the ac driving signals that have different frequencies and that contain a little frequency component of a noise detected by the noise detecting means.

9. A shape-of-endoscope detecting system according to claim 8, wherein the plurality of elements disposed in the endoscope insertion portion is the plurality of magnetic-field generating elements.

10. A shape-of-endoscope detecting system according to claim 8, wherein the ac driving signals having different frequencies can be selected from a plurality of groups of driving signals having different frequencies, and the noise detecting means detects an amplitude component of a noise whose frequency corresponds to each of the frequencies of each group of driving signals having different frequencies.

11. A shape-of-endoscope detecting system according to claim 1, wherein: a plurality of coils is disposed as the one of the plurality of elements in the endoscope insertion portion; and an intermittently driving means is included for dividing the plurality of coils into a plurality of groups, and for intermittently driving the coils belonging to each group so that the driving timings at which the respective coils are driven will not coincide with one another.

12. A shape-of-endoscope detecting system according to claim 11, wherein if each group includes a plurality of coils, the plurality of coils is driven using driving signals having different frequencies.

13. A shape-of-endoscope detecting system according to claim 11, wherein the plurality of coils is also employed in auxiliaries that are disposed outside the endoscope insertion portion.

14. A shape-of-insertion portion detecting system for inferring a shape of an insertion portion that is flexible and adapted for insertion into a subject, the shape-of-insertion portion detecting system comprising:
  position detecting elements disposed at predetermined intervals in the longitudinal direction of the insertion portion;
  a position detecting means for detecting positions of the position detecting
  a data interpolating means
    for, positioning a virtual element between the detected positions of adjoining position detecting elements based on the output of the detecting means so that a predetermined condition will be met, and
    for interpolating data using position data representing the positions of the adjoining elements and position data representing the position of the virtual element so as to infer the shape of the insertion portion.

15. A shape-of-endoscope detecting system according to claim 14, wherein the data interpolation is executed by software.

16. A shape-of-insertion portion detecting system according to claim 14, wherein the insertion portion is an endoscope insertion portion having an illumination window, through which illumination light is emitted, and an observation window, through which a field illuminated with the illumination light is observed, formed in the distal section of the insertion portion.

17. A shape-of-endo scope detecting system for inferring a shape of an endoscope insertion portion adapted for insertion in to a subject, the shape-of-endoscope detecting system comprising:
  a detecting means for detecting positions of one of a plurality of magnetic-field generating elements and a plurality of magnetic-field detecting elements, disposed in the endoscope insertion portion, using positions of the other of the plurality of magnetic-field generating elements and the plurality of magnetic-field detecting elements, disposed outside the subject;
  a data interpolating means
    for, positioning one or more virtual elements among the plurality of magnetic-field generating elements or magnetic-field detecting elements whose positions are detected, based on the detected positions detected by the detecting means, and
    for interpolating data, which represents one or more intermediate positions between the detected positions of adjoining elements of the plurality of magnetic-field generating elements or magnetic-field detecting elements whose positions are detected, using the positions of the one or more virtual elements;
  a noise detecting means for selecting ac driving signals that have different frequencies and that are used to drive the plurality of magnetic-field generating elements, and for detecting a frequency component of a noise in a driving pause state in which the plurality of magnetic-field generating elements is not driven; and
  a driving control means for driving the plurality of magnetic-field generating elements using the ac driving signals that have different frequencies and that contain a little frequency component of a noise detected by the noise detecting means.

18. A shape-of-endoscope detecting system according to claim 17, wherein: the ac driving signals having different frequencies can be selected from a plurality of groups of driving signals having different frequencies; and the noise detecting means detects an amplitude component of a noise whose frequency corresponds to each of the frequencies of each group of driving signals having different frequencies.

19. A shape-of-endoscope detecting system for detecting the shape of an endoscope insertion portion, the shape-of-endoscope detecting system comprising:
  a plurality of coils disposed in the endoscope insertion portion;
  a driving signal applying means for applying driving signals to the plurality of coils disposed in the endoscope insertion portion;
  a detecting means for detecting the positions of the plurality of coils disposed in the endoscope insertion portion;
  a data interpolating means
    for positioning virtual elements among the plurality of coils disposed in the endoscope insertion portion based on the detected positions of the plurality of coils disposed in the endoscope insertion portion, and
    for interpolating data, which represents one or more intermediate positions between the detected positions of adjoining coils, using the positions of the one or more virtual elements; and
  an intermittently driving means that intermittently drives coils, which belong to each of a plurality of groups into which the plurality of coils is divided, so that the driving timings at which the respective coils are driven will not coincide with one another.

20. A shape-of-endo scope detecting system according to claim 19, wherein if each group includes a plurality of coils, the plurality of coils is driven using driving signals having different frequencies.

* * * * *